(12) United States Patent
Harshbarger et al.

(10) Patent No.: US 9,486,332 B2
(45) Date of Patent: Nov. 8, 2016

(54) MULTI-MODAL NEURAL INTERFACING FOR PROSTHETIC DEVICES

(75) Inventors: Stuart D. Harshbarger, Woodbine, MD (US); James D. Beaty, Columbia, MD (US); R. Jacob Vogelstein, Bethesda, MD (US); Nitish V. Thakor, Clarksville, MD (US)

(73) Assignee: The Johns Hopkins University, Baltimore, MD (US)

( * ) Notice: Subject to any disclaimer, the term of this patent is extended or adjusted under 35 U.S.C. 154(b) by 58 days.

(21) Appl. No.: 14/110,508

(22) PCT Filed: Apr. 15, 2011

(86) PCT No.: PCT/US2011/032603
§ 371 (c)(1),
(2), (4) Date: Oct. 8, 2013

(87) PCT Pub. No.: WO2012/141714
PCT Pub. Date: Oct. 18, 2012

(65) Prior Publication Data
US 2014/0031952 A1    Jan. 30, 2014

(51) Int. Cl.
*A61F 2/72* (2006.01)
*A61F 2/68* (2006.01)
*A61F 2/54* (2006.01)
*A61F 2/50* (2006.01)

(52) U.S. Cl.
CPC .. *A61F 2/72* (2013.01); *A61F 2/54* (2013.01); *A61F 2002/5058* (2013.01); *A61F 2002/5059* (2013.01); *A61F 2002/5061* (2013.01); *A61F 2002/5063* (2013.01)

(58) Field of Classification Search
CPC .................................. A61F 2/68; A61F 2/72
See application file for complete search history.

(56) References Cited

U.S. PATENT DOCUMENTS

| | | | |
|---|---|---|---|
| 5,299,118 | A | 3/1994 | Martens et al. |
| 5,470,081 | A | 11/1995 | Sato et al. |
| 5,692,517 | A | 12/1997 | Junker |
| 5,840,040 | A | 11/1998 | Altschuler et al. |
| 6,344,062 | B1 | 2/2002 | Abboudi et al. |
| 6,859,663 | B2 | 2/2005 | Kajitani et al. |
| 6,952,687 | B2 | 10/2005 | Andersen et al. |
| 6,988,056 | B2 | 1/2006 | Cook |

(Continued)

FOREIGN PATENT DOCUMENTS

| | | |
|---|---|---|
| WO | 02/49534 | 6/2002 |
| WO | 2007/058950 | 5/2007 |

(Continued)

OTHER PUBLICATIONS

Kauhanen et al., "EEG-Based Brain-Computer Interface for Tetraplegics," Computational Intelligence and Neuroscience, vol. 2007, Aug. 2, 2007, 11 pages.

(Continued)

*Primary Examiner* — Bruce E Snow
(74) *Attorney, Agent, or Firm* — Todd R. Farnsworth

(57) ABSTRACT

Methods and systems to interface between physiological devices and a prosthetic device, including to receive a plurality of types of physiological activity signals from a user, decode a user movement intent from each of the plurality of signals types, and fuse the movement intents into a joint decision to control moveable elements of the prosthetic device.

12 Claims, 59 Drawing Sheets

(56) References Cited

U.S. PATENT DOCUMENTS

| | | |
|---|---|---|
| 7,260,436 B2 | 8/2007 | Kilgore et al. |
| 7,286,871 B2 | 10/2007 | Cohen |
| 7,299,089 B2 | 11/2007 | Wolf et al. |
| 7,330,754 B2 | 2/2008 | Jensen |
| 7,406,105 B2 | 7/2008 | DelMain et al. |
| 2002/0077534 A1 | 6/2002 | DuRousseau |
| 2002/0182574 A1 | 12/2002 | Freer |
| 2004/0204769 A1 | 10/2004 | Richmond et al. |
| 2004/0267320 A1 | 12/2004 | Taylor et al. |
| 2005/0090756 A1 | 4/2005 | Wolf et al. |
| 2006/0116738 A1 | 6/2006 | Wolf et al. |
| 2006/0217816 A1 | 9/2006 | Pesaran et al. |
| 2007/0032738 A1 | 2/2007 | Flaherty et al. |
| 2007/0123350 A1 | 5/2007 | Soderlund |
| 2008/0058668 A1 | 3/2008 | Momen et al. |
| 2008/0140154 A1 | 6/2008 | Loeb et al. |

FOREIGN PATENT DOCUMENTS

| | | |
|---|---|---|
| WO | 2008/122044 | 10/2008 |
| WO | 2008/151291 | 12/2008 |

OTHER PUBLICATIONS

Krauledat et al., "Towards Zero Training for Brain-Computer Interfacing," vol. 3, Issue 8, Aug. 2008, 12 pages.

Babiloni, F. et al., Multimodal Integration of EEG and MEG Data: A Simulation Study with Variable Signal-to-Noise Ratio and Number of Sensors, Human Brain Mapping, vol. 22(1) Dec. 1, 2003, pp. 52-64.

Gevins, A. et al., "Neurocognitive Networks of the Human Brain," Annals of the New York Academy of Sciences, vol. 620, Apr. 1991, pp. 22-44.

Moosman et al., "Joint Independent Component Analysis for Simultaneous EEG-fMRI: Principle and Simulation," International Journal of Psychophysiology, vol. 67(3), Jul. 12, 2007, pp. 212-221.

MULTI-MODAL NEURAL INTERFACING FOR PROSTHETIC DEVICES

STATEMENT OF GOVERNMENTAL INTEREST

This invention was made with U.S. Government support under the Naval Sea Systems Command under contract number N66001-06-C-8005. The U.S. Government has certain rights in the invention.

BACKGROUND

1. Technical Field

Disclosed herein are methods and systems to interface between physiological devices and a prosthetic system, including to receive a plurality of types of physiological activity signals from a user, decode a user movement intent from each of the plurality of signals types, and fuse the movement intents into a joint decision to control moveable elements of the prosthetic device.

2. Related Art

Various types of sensors have been developed to monitor various physiological features.

Systems have been developed to control prosthetic devices in response to electrical signals output from a physiological sensor, referred to herein as single-mode prosthetic device control.

User movement intent may, however, be expressed in multiple ways through a variety of physiological means, which may be detectable with different types of sensors that output different types of electrical signals.

Reliability of a user movement intent decoded from any given sensor or signal type may vary with respect to one or more of a variety of factors, such as a particular pre-movement state, a particular desired movement, environment factors, and mental state.

Theoretically, more accurate estimate of user movement intent should be determinable by combining information from multiple sensor types. Interrelations amongst various physiological means are, however, notoriously difficult to ascertain.

What are needed are methods and system to determine user movement intents from each of a plurality of types of physiological sensors and/or signal types, and to fuse the movement intents to provide a more informed estimate of user intended movement.

SUMMARY

Disclosed herein are methods and systems to multi-modally interface between physiological sensors and a prosthetic device, including to receive a plurality of types of physiological activity signals from a prosthetic device user, decode a user movement intent from each of the plurality of signals types, and fuse the movement intents into a joint decision to control moveable elements of the prosthetic device.

A multi-modal neural interface system (NI) may be configured to receive a plurality of types of physiological activity signals from a prosthetic device user, decode a user movement intent from each of the plurality of signals types, and fuse the movement intents into a joint decision to control moveable elements of the prosthetic device.

The NI may include a plurality of classifier modules, each associated with a corresponding one of the signal types to determine a user movement state from signals of the signal type.

The NI may include a plurality of decode modules, each associated with a corresponding one of the signal types to decode a movement intent from signals of the signal type and from one or more of the user movement states; and The NI may include a fusion module to fuse movement intents from a plurality of the decode modules into the joint movement decision.

The plurality of signal types include one or more of, a local filed potential (LFP) signal,
a unit activity (spike) signal,
an epidural electrocorticography grid (ECoG) signal,
an electromyography (EMG) signal,
an electroencephalography (EEG) signal, and
an electronystagmography (ENG) signal.

The plurality of signal types may be received from a plurality of types of physiological sensors, which may include one or more types of neurological sensors.

The NI may include a plurality of groups of classifier modules, each group associated with a corresponding group of control (GOC) of the prosthetic device. The NI may further include a plurality of groups of decode modules, each group associated with a corresponding one of the GOC. The NI may further include a plurality of fusion modules, each associated with a corresponding one of the GOCs to fuse the movement intents from decode modules of the GOC into a joint decision of the GOC. The NI may further include a motion estimator to generate a movement action from joint movement decisions of a plurality of the GOCs.

The prosthetic device may include, for example, a prosthetic arm and hand, and the groups of control may include an upper arm group, a wrist group, a hand and finger group, and an endpoint group.

The NI may be configured to receive and incorporate sensory feedback from the prosthetic device into the joint movement decision. Sensory feedback may include one or more of velocity, speed, force, direction, position, and temperature information.

The NI may include a plurality of modular and configurable components, including a base configuration to process signals from one or more relatively non-invasive physiological sensors, and one or more selectively enabled modules to process signals from one or more relatively invasive physiological sensors.

A decode module may be configured to compute an unnormalized log posterior probability (ULPP) value for each of a plurality of classes of movement in accordance with Bayesian classifiers. The decode module may be further configured to determine a movement intent from the ULPP values, and output the movement intent and/or the ULPP values. Where the decode module is configured to output ULLP values, the fusion module may be configured to generate the joint movement decision based at least in part of the ULPP values.

Methods and systems disclosed herein are not limited to the summary above.

BRIEF DESCRIPTION OF THE DRAWINGS/FIGURES

Figure 1:
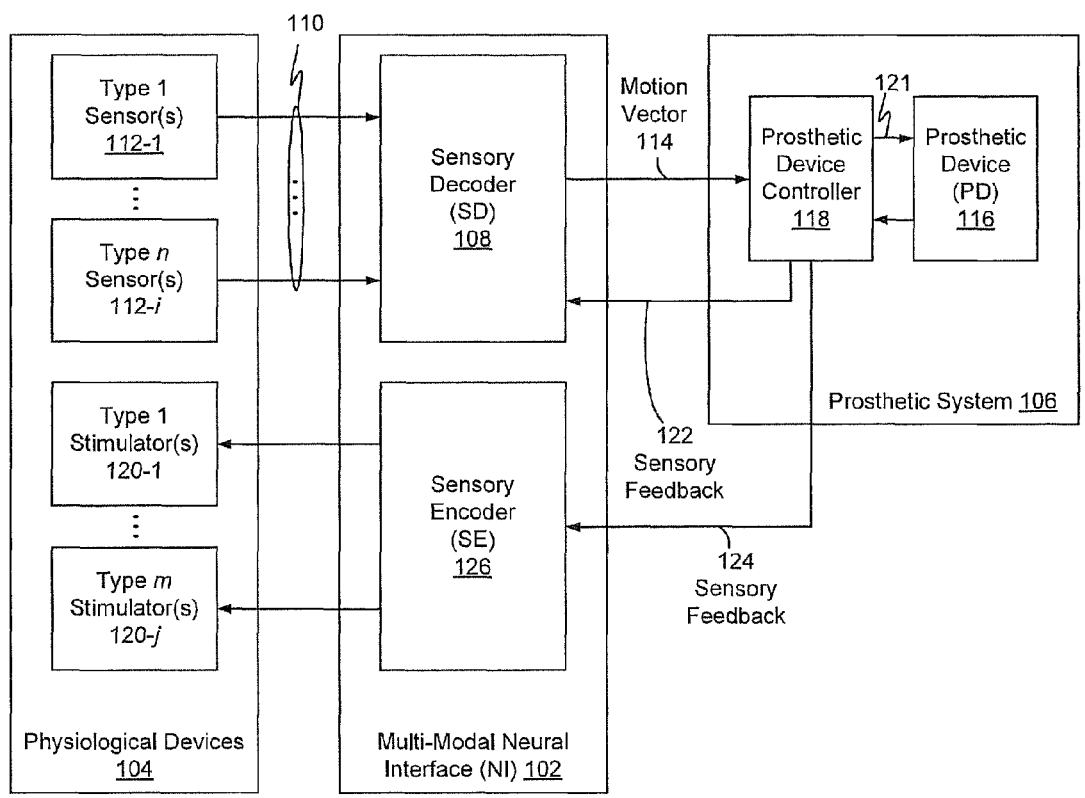
FIG. 1 is a block diagram of a neural interface system (NI) to interface between physiological devices and a prosthetic system.

In the drawings, the leftmost digit(s) of a reference number identifies the drawing in which the reference number first appears.

DETAILED DESCRIPTION

1. Neural Interfacing, Including Sensory Decoding and Sensory Encoding

FIG. 1 is a block diagram of a multi-modal neural interface system (NI) 102 to interface between physiological devices 104 and a prosthetic system 106.

Physiological devices 104 may include a plurality of types of sensors 112-1 through **112-*i*, and/or one or more stimulators 120-1 through 120-*j***, which may include, without limitation, implantable neurological devices, implantable muscular devices, and/or surface-based muscular devices. Example devices are disclosed further below.

Sensors 112 may output neural motor control data as electrical signals 110. Signals 110 may include digitized neural data, which may represent or correspond to physiological and/or neurological signals.

Where physiological devices 104 include a plurality of types of sensors 112, NI 102 may include a sensory decoder (SD) 108, also referred to herein as a motor decode system, to decode neural motor control data from the multiple types of sensors 112. Decoded neural motor control data may include movement intent information, also referred to herein as movement decisions, corresponding to each of multiple sensors and/or multiple sensor types 112. NI may be further configured to computationally fuse the motion intent information to generate a joint action decision 114. Joint movement decision 114 may represent an estimate of a user's desired movement, and may be based on a plurality of sensor and/or signal types. Joint action decision 114 may be embodied as a vector, referred to herein as a joint movement decision vector.

SD 108 may include a plurality of motion decoders, each associated with a corresponding type of sensor 112. SD 108 may further include a fusion module to combine motion intent determinations associated with multiple motion decoders.

Prosthetic system 106 may include a PD controller 118 to convert joint decision motion vector 114 to one or more motor control signals 121, to control a prosthetic device (PD) 116. PD 116 may include one or more a prosthetic limb and/or appendage.

Prosthetic system 106 may be configured to provide feedback information to NI 102, which may include one or more of sensory feedback 122 and sensory feedback 124.

Prosthetic system 106 may, for example, include sensors to sense one or more of position, speed, velocity, acceleration, and direction associated with PD 116, and PD controller 118 may be configured to provide corresponding information to SD 108 as sensory feedback 122. SD 108 may be configured to utilize sensory feedback 122 to generate and/or revise motion vector 114.

Alternatively, or additionally, prosthetic system 106 may include one or more environmental sensors, which may include one or more of temperature and/or pressure sensors, and prosthetic system 106 may be configured to provide corresponding information to NI 102 as sensory feedback 124. Sensory feedback 122 and sensory feedback 124 may be identical to one another, exclusive of one another, or may include some overlapping data.

NI 102 may include a sensory encoder (SE) 126 to convert sensory feedback 124 to stimulate one or more stimulators 120.

NI 102 may be implemented to include one or both of SD 108 and SE 126.

Sensors 112 and/or stimulators 120 may include one or more relatively non-invasive devices and/or one or more relatively invasive devices. Example devices are presented below. Methods and systems disclosed herein are not, however, limited to the example devices disclosed herein.

Signals 110 may include a plurality of types of signals corresponding to types of sensors 12. Signals 110 may include, for example, one or more of single-unit activity spikes/indications, multi-unit activity spikes/indications, a local field potential (LPF), an epidural electrocorticography grid (ECoG), and electromyography (EMG) signals.

SD 108 may include corresponding spike, LPF, ECoG, and EMG decoders, and may include a fusion unit to computationally fuse outputs of multiple decoders. The fusion unit may be configured to resolve conflicting decoded motor control movement data and/or decisions generated therefrom. An example is provided below with respect to FIG. 2.

Figure 2:
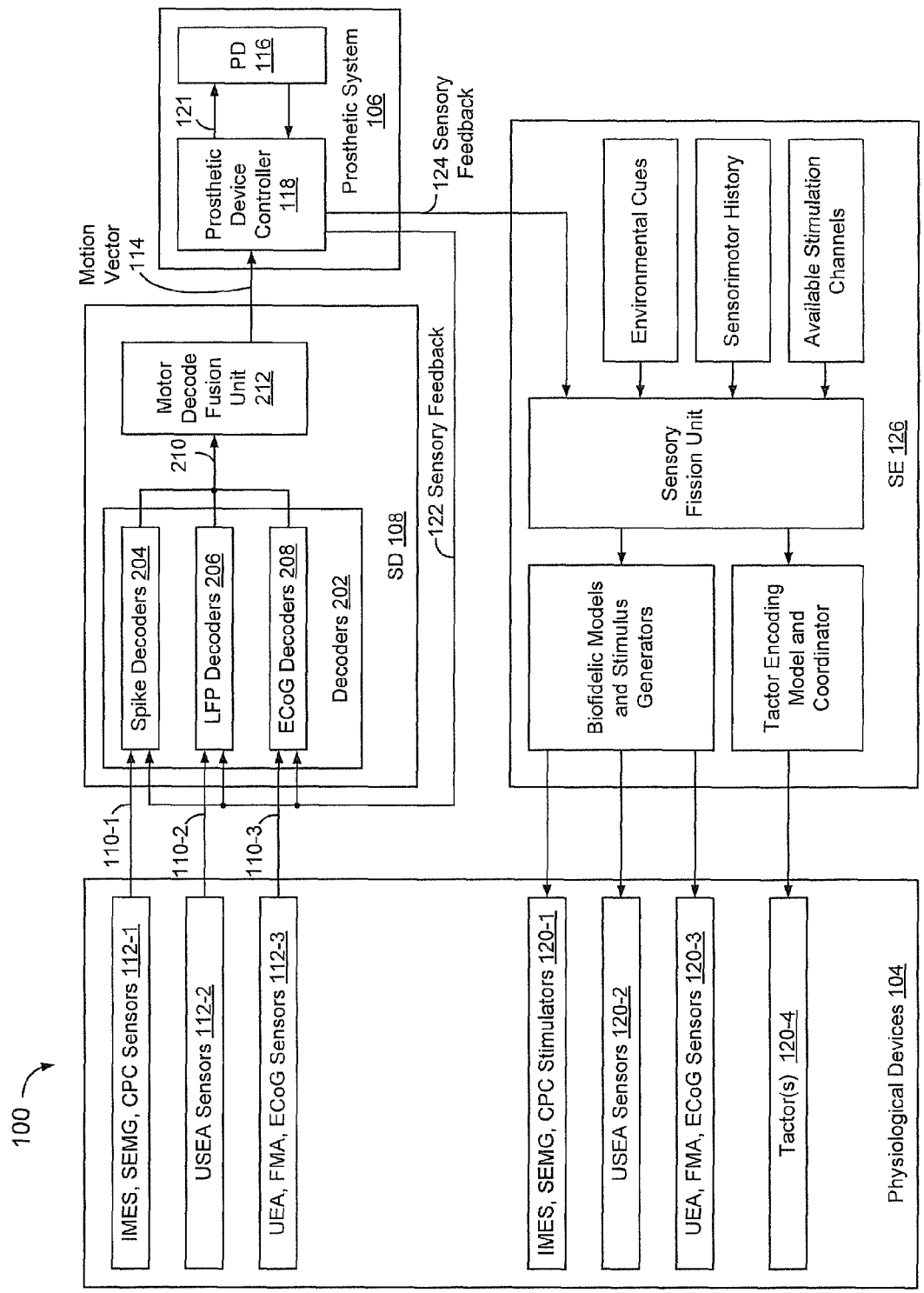
FIG. 2 is a block diagram of the NI of FIG. 1, including a plurality of spike decoders, LFP decoders, and ECoG decoders.

FIG. 2 is a block diagram of NI 102, physiological devices 104, and prosthetic system 106, wherein SD 108 includes a plurality of decoders 202, illustrated here as spike decoders 204, LFP decoders 206, and ECoG decoders 208. Decoders 202 output data 210, which may include one or more of decoded motor control data and movement decisions generated from decoded motor control data. Decoded movement decisions are also referred to herein as movement intents.

SD 108 further includes a fusion unit 212 to resolve potential differences and/or conflicts between decoded motor control data and/or decisions output from decoders 202. Fusion unit 212 may include a data fusion module to computationally fuse decode motor control data, and/or a decision fusion module to computationally fuse movement decisions.

PD 116 may include a plurality of controllable elements, each having one or more corresponding degrees of controllable motion. Each element may be associated with one of a plurality of groups. Each group may include one or more elements. For example, and without limitation, PD 116 may correspond to a prosthetic arm, which may include an upper arm group, a wrist group, a hand/finger group, and an endpoint group.

Decoders 204, 206, and 208, may each include a set of feature extractor and/or classifier modules for each group of elements of PD 116, and fusion unit 212 may include a fusion module for each group of elements of PD 116. An example is provided below with respect to FIG. 3.

Figure 3:
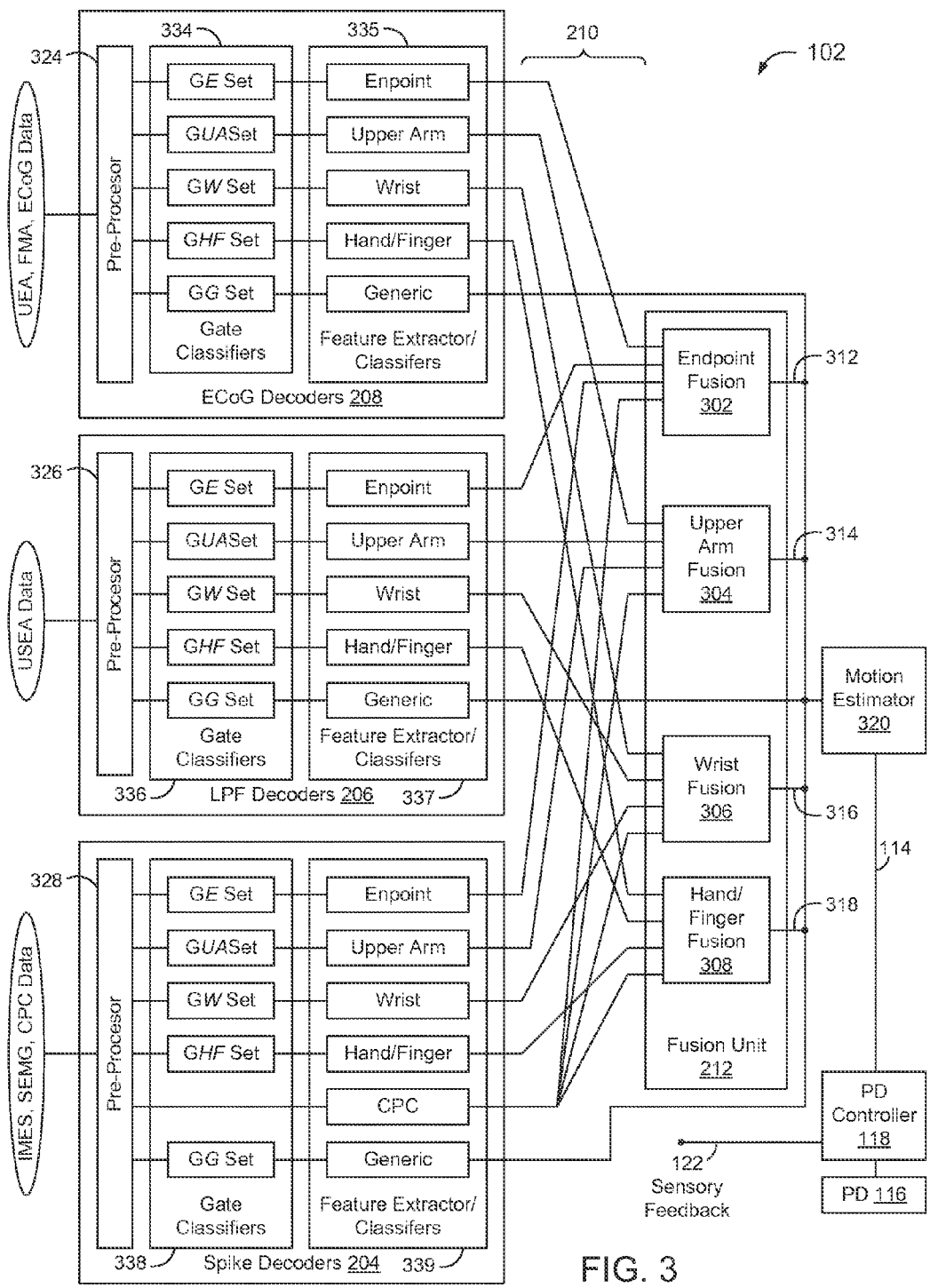
FIG. 3 is a block diagram of the NI of FIG. 2, configured with respect to a plurality of groups of control (GOC), illustrated here as an upper arm group, a wrist group, a hand/finger group, an endpoint group, and a generic group.

FIG. 3 is a block diagram of NI 102 configured with respect to a plurality of groups of control (GOC), illustrated here as an upper arm group, a wrist group, a hand/finger group, an endpoint group, and a generic group.

In the example of FIG. 3, NI 102 includes a gate classifier modules and feature extractor/classifiers modules, each associated with a corresponding signal type GOC.

Fusion unit 212 may include multiple fusion modules, illustrated here as an endpoint fusion module 302, an upper arm fusion module 304, a wrist fusion module 306, and a hand/finger fusion module 308, to output corresponding vectors 312, 314, 316, and 318.

Where outputs 210 of the endpoint, upper arm, wrist, and hand/finger feature extractor/classifier modules 335, 337, and 339 include decoded motor control data, fusion modules 302, 304, 306, and 306 may include data fusion modules.

Where outputs 210 of the endpoint, upper arm, wrist, and hand/finger feature extractor/classifier modules 335, 337, and 339 include movement decisions, fusion modules 302, 304, 306, and 306 may include decision fusion modules.

SD 108 may include a motion estimator 320 to generate joint motion vector 114 from vectors 312, 314, 316, and 318.

NI 102 may include pre-processors 324, 326, and 328, and gate classifiers 334, 336, and 338, e.g. gate classifier modules. Pre-processing and gate classification are described below, in FIG. 25.

Additional example implementations are provided in sections below. Features disclosed with respect to an example herein are not limited to the example. Rather, one or more features disclosed with respect to an example herein may be combined with one or more features of other examples disclosed herein.

2. Example 1

(a) Neural Interface

A neural interface (NI) may provide bidirectional communications between a prosthetic limb (PL) and a user's nervous system (NS). Output channels, denoted NS→PL, may be used to determine the user's desired movements for the PL based on observed neural activity. Input channels, denoted PL→NS, may be used to provide the user with sensory feedback from the PL by stimulating neural afferents. Such feed-forward and feedback pathways of a NI may be implemented to provide a user with closed loop control over the PL.

Figure 4:
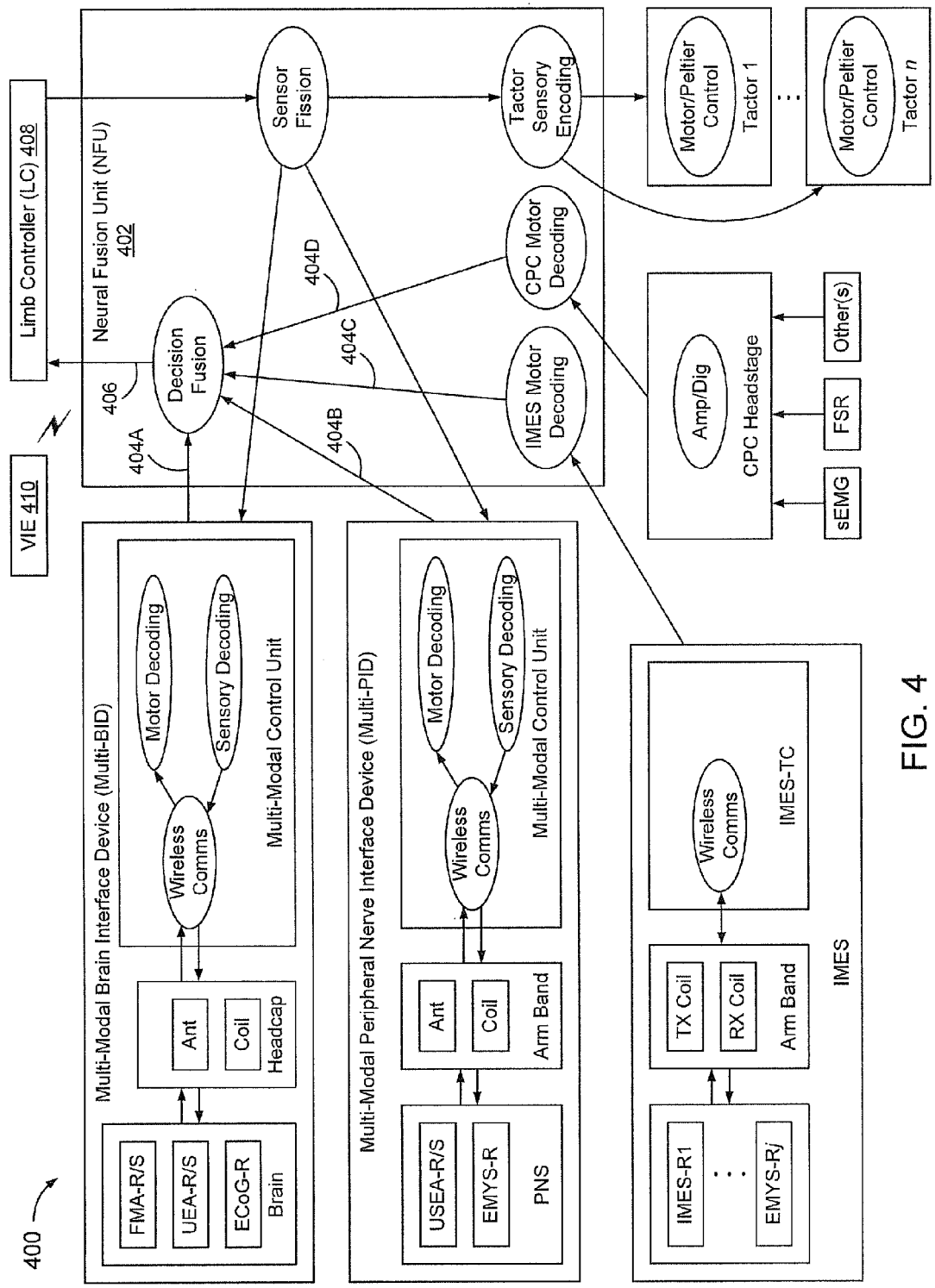
FIG. 4 is a block diagram of another NI.

FIG. 4 is a block diagram of an example neural interface system (NI) 400.

NI 400 may be implemented modularly, such as to facilitate isolation of potential FDA Class II devices from potential FDA Class III devices, and/or to accommodate users with different injury types.

NI 400 may include a neural fusion unit (NFU) 402 to serve as a central communications and processing hub of NI 400. NFU 402 may be provided with multiple NI configurations.

NI 400 may include one or more attachments to NFU 402, which may provide additional functionality to communicate with a user's nervous system through one or more neural interface devices.

Depending on a user's injury level, comfort with implanted systems, and willingness to undergo invasive surgeries, the user may elect to use one or more of a variety of neural interface devices.

Example neural interface devices include:
conventional prosthetic controls (CPC, non-invasive), including surface electromyography recording electrodes (SEMG-R);
tactile sensory stimulators (Tactors, non-invasive);
implantable myoelectric sensors for EMG recording (IMES-R, minimally-invasive);
Utah Slanted Electrode Arrays for peripheral nerve recordings (USEA-R, moderately-invasive);
Utah slanted electrode arrays for peripheral nerve stimulation (USEA-S, moderately-invasive);
epidural electrocorticography grids for cortical recording (ECoG-R, highly-invasive);
Utah electrode arrays for cortical recording (UEA-R, highly-invasive);
Utah electrode arrays for cortical stimulation (UEA-S, highly-invasive);
floating microelectrode arrays for cortical recording (FMA-R, highly-invasive); and
floating microelectrode arrays for cortical stimulation (FMA-S, highly-invasive).

Data flow through NI 400 is described below with respect to a feed-forward or monitoring pathway, and a feedback or sensory pathway.

In the example of FIG. 4, the feed-forward pathway includes four feed-forward channels, one for each of:
non-invasive conventional prosthetic controls;
minimally-invasive EMG recording devices (IMES-R);
moderately-invasive peripheral nerve recording devices (USEA-R); and
highly-invasive cortical recording devices (FMA-R, UEA-R, and ECoG-R).

Each feed-forward channel may monitor one or more types of neuromotor activity and may transmit information to a local processing module, referred to herein as a multi-modal control unit (MCU). MCUs decode data to determine which, if any, PL movements are intended or desired by the user. Output from the MCUs, or local decoders, may include movement decisions 404, which may be combined within NFU 402 to generate an output command to the PL, referred to herein as an action 406.

The feedback pathway operates in a similar fashion to the feed-forward pathway, in reverse. Specifically, sensory data from the prosthetic limb is aggregated within NFU 402, which separates the information for presentation through available feedback channels. In the example of FIG. 4, NI 400 includes three feedback channels, one for each of:
non-invasive tactile stimulation devices (Tactors);
moderately-invasive peripheral nerve stimulation devices (USEA-S); and
highly-invasive cortical stimulation devices (UEA-S and FMA-S).

Within each feedback channel, percepts to be delivered to the user may be locally encoded into patterns of stimulation to elicit appropriate sensations. A pattern may be specific to a neural stimulation device.

Invasive implantable neural recording and stimulation devices may be configured to operate wirelessly, including to receive power and data over a first radiofrequency (RF) link and to transmit data over a second RF link.

A MCU, which may be implemented as a modular attachment to NFU 402, may implement the wireless functionality, and may provide local motor decoding and sensory encoding functions for cortical devices and peripheral nerve devices.

A user with cortical or peripheral nerve implants may be provided with multiple implanted devices, such as a recording device and a stimulating device, and each MCU may be configured to accommodate multiple implants.

A collection of one or more cortical implants, an associated MCU, and a headcap device that physically resides on a user's head above the implants and that houses the external antennas, is referred to as a multi-modal brain interface device (multi-BID).

Similarly, a collection of one or more peripheral nerve implants, an associated MCU, and an armband device that may physically reside on the user's residual limb around the implants and that houses external antennas, is referred to as a multi-modal peripheral interface device (multi-PID).

A multi-BID and a multi-PID are logical groupings of NI components that perform a function. In other words, there may not be a monolithic multi-BID or multi-PID entity. For engineering convenience, multiple wireless implantable devices that communicate with a MCU may share a common wireless interface and communication protocol.

In FIG. 4, data may be transmitted to and received from a limb controller (LC) 408 via a communication bus. Data may be communicated over a wireless link to a VIE 410.

NI 400 may include recording epimysial electrodes (EMYS-R).

NI 400 may include conventional prosthetic controls, such as surface electromyography recording electrodes, force-sensitive resistors, and/or joysticks.

Feed-forward and feedback channels supporting non-invasive and minimally-invasive neural recording and stimulation devices may operate substantially similar to moderately-invasive and highly-invasive channels. Comparable functionality of a MCU for non-invasive devices, such as CPC and tactors may be divided amongst NFU 402, a CPC headstage, and a set of tactor controllers.

Comparable functionality of a MCU for minimally-invasive devices, such as MES-R, may be spread amongst NFU 402 and an IMES telemetry controller (IMES-TC). Local motor decoding and sensory encoding functions may be executed by NFU 402.

Lower-level device controls, such as amplification and digitization for the CPC, wireless communication for the IMES-R, and motor control for the tactors, may be executed on a elatively small dedicated CPC Headstage, IMES-TC, and tactor controller modules coupled to or attached to NFU 402.

NI 400 may include one or more of:
neural fusion unit hardware/software (HW/SW);
multi-modal control unit HW/SW;
headcap mechanical hardware (MHW);
armband MHW;
CPC headstage HW/SW;
tactor controller HW/SW;
non-invasive neural interfaces, such as a conventional prosthetic controller (CPC), which may include SEMG-R, and/or a tactor MHW;
a minimally-invasive neural interface, such as a IMES, which may include a IMES-R and/or IMES-TC);
a moderately-invasive neural interface, such as USEA-R and/or USEA-S; and
a highly-invasive neural interface, such as ECoG-R, UEA-R, UEA-S, FMA-R, and/or FMA-S.

Figure 5:
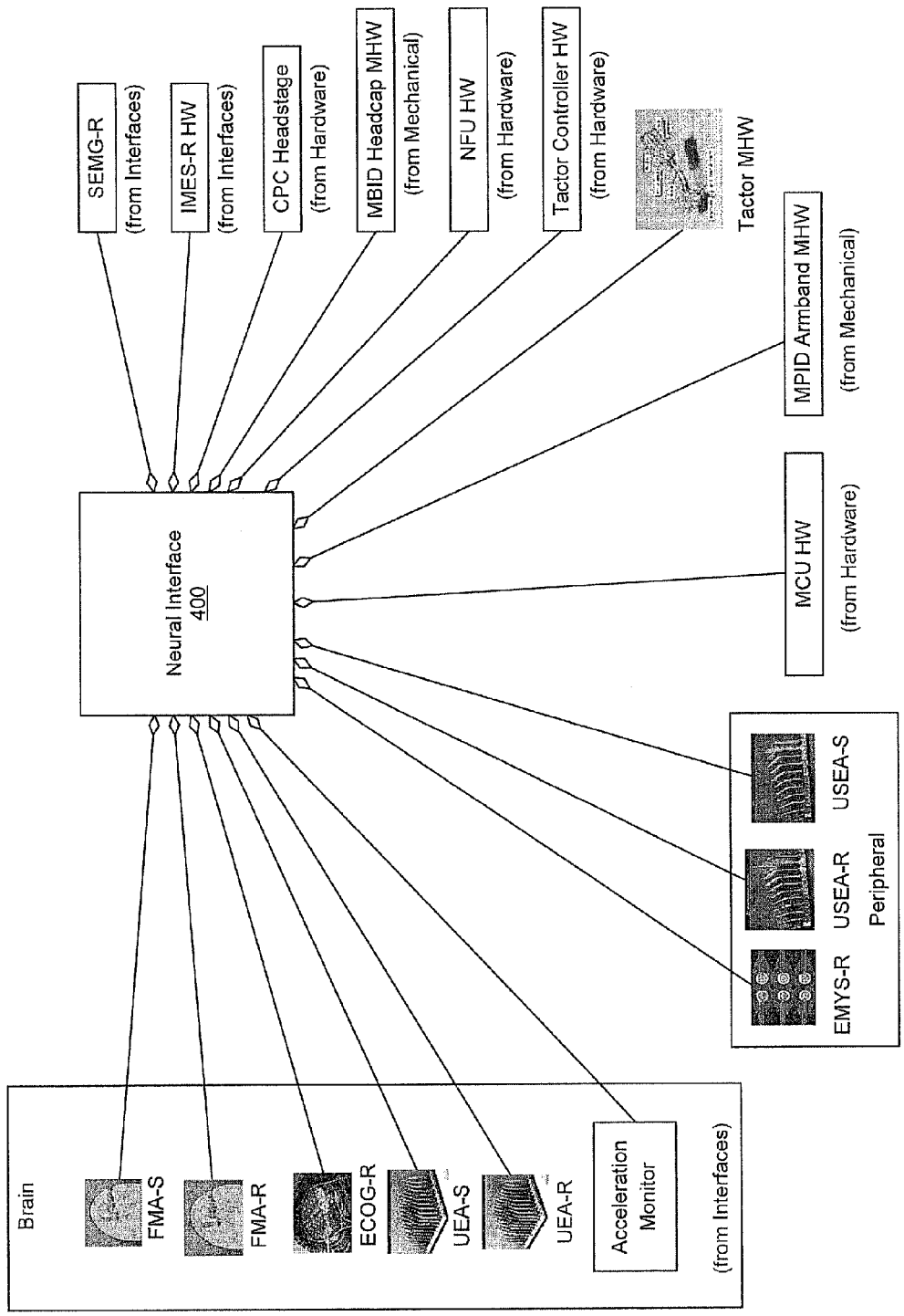
FIG. 5 is a graphic depiction of the NI of FIG. 4, and example components thereof.

FIG. 5 is a graphic depiction of NI 400 and example components. As illustrated in FIG. 5, NI 400 may include an epimysial grid (EMYS-R) and an acceleration monitor.

Example NI subsystems are further described below.

(b) Sensory Decoding

As described above with respect to SD 108 in FIG. 1, a NI may include a motor decode system to host a set of motor decoding modules or algorithms to convert neural activity into limb commands. An example motor decode system is disclosed below with reference to FIG. 6.

Figure 6:
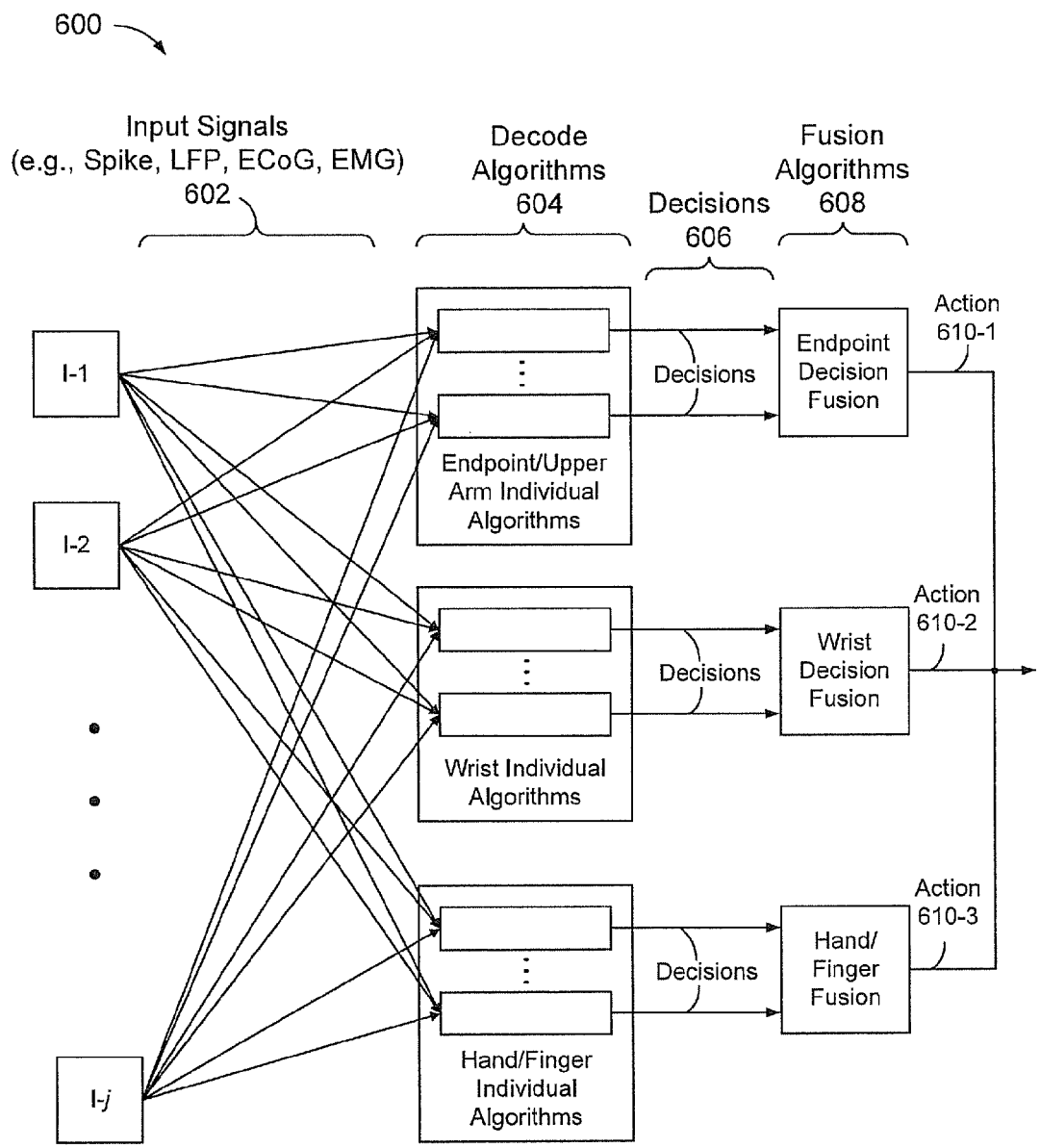
FIG. 6 is a block diagram of a motor decode system to decide single or multi-unit activity ("spikes"), local field potentials (LFP), ECoG signals, and EMG signals.

FIG. 6 is a block diagram of a motor decode system 600 to receive digitized neural data 602, which may include one or more of single or multi-unit activity ("spikes"), local field potentials (LFP), ECoG signals, or EMG signals.

Motor decode system 600 routes input signals 602 to appropriate decode algorithms 604. Decode algorithms 604 produce decisions 606 representing a user-intended or desired movement for one or more PL degrees of control (DOC) in one or more groups of control (GOC). In the example of FIG. 6, motor decode system 600 provides three GOCs, including an endpoint/upper arm group, a wrist group, and a hand/finger group. Multiple decode algorithms 604 may output different decisions 606 for the same GOC.

Motor decode system 600 may include a second layer of processing containing fusion algorithms 608 to combine multiple decisions 606 and to generate a single output action 610, which represents a best estimate of the user's intended or desired movement with respect to the corresponding GOC. Actions 610 may be used to command movements of a prosthetic limb.

One or more algorithms may not be suitable to accept all inputs, and mapping of inputs to algorithms may be configurable.

Where a NI is implemented in a modular fashion, motor decoding algorithms may also be implemented in a modular fashion. For example, a NFU may host fusion algorithms to accommodate decisions provided by one or more individual algorithms, depending on which neural recording devices and signal types are available for an individual user. The individual algorithms may be hosted on the NFU, such as for surface EMG and IMES-R decoding, and/or a MCU, such as for cortical activity or peripheral nerve decoding. Partitioning of functionality may permit relatively efficient use of processors and may reduce bandwidth and power requirements of a MCU-to-NFU bus.

Additional example motor decoding features are disclosed further below.

(c) Sensory Encoding

As described above with respect to SE 126 in FIG. 1, a NI may include a sensory encoder to host a set of sensory encoding modules or algorithms. An example sensory encoder is disclosed below with reference to FIG. 7.

Figure 7:
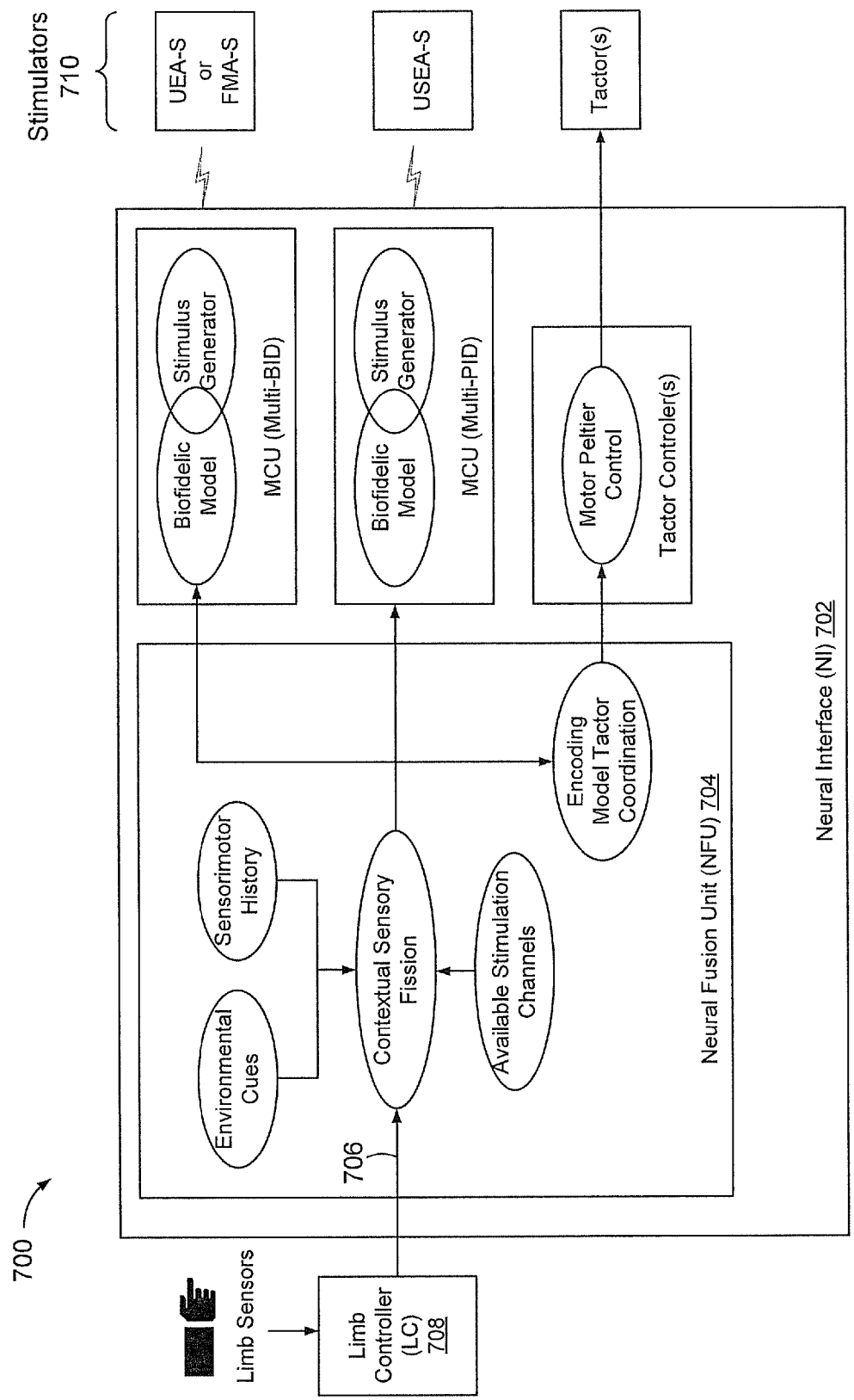
FIG. 7 is a block diagram of another NI, including a neural fusion unit (NFU) to receive sensory feedback from a limb controller, and to provide corresponding stimulation to one or more stimulators.

FIG. 7 is a block diagram of neural interface (NI) 702, including a neural fusion unit 704 to receive sensory feedback 706 from a limb controller 708, and to provide corresponding stimulation to one or more stimulators 710.

NI 702 may include a plurality of sensory encoding modules, each associated with a corresponding type of stimulator. A sensory encoding module may be configured to aggregate sensory feedback 706 from one or more sensors and/or types of sensors, and to output one or more stimulator control signals to one or more stimulators and/or types of stimulators. A sensory encoding module may be configured to perform an n to m mapping, to map sensory feedback 706 from n sensors and/or sensor types, to m different afferent pathways, where n may be greater or less than m. Such a mapping process may provide a user with feedback information in a relatively natural and intuitive fashion.

Such a mapping process may include a fusion process, referred to herein as contextual sensory fission (CSF). A CSF process may be implemented with one or more algorithms, and may operate within a neural fusion unit (NFU) of a NI. A CSF system may be configured to develop a set of sensory states that characterize a current function of a PL at a relatively high level (e.g. object has been grasped, object is slipping, or hand is exploring environment). The CSF system may be further configured to assign generation of individual sensory percepts to one or more available feedback channels, to encoding the individual sensory percepts in a format or language of one or more types of stimulators 710, which may include one r more of tactors, USEA-S, FMA-S, and/or UEA-S.

(d) Neural Interface Devices

Example neural interface devices are disclosed below.

(i) Conventional Prosthetic Controls (CPC)

Conventional prosthetic controls may include non-invasive recording devices such as SEMG-R, joysticks, force-sensitive resistors, electromechanical switches, and/or other conventional controls. A set of these may be selected for a particular user depending on the user's level of injury and residual limb function. Depending on a particular socket configuration, CPC may be integrated into a socket liner or attached to other parts of the socket.

Figure 8:
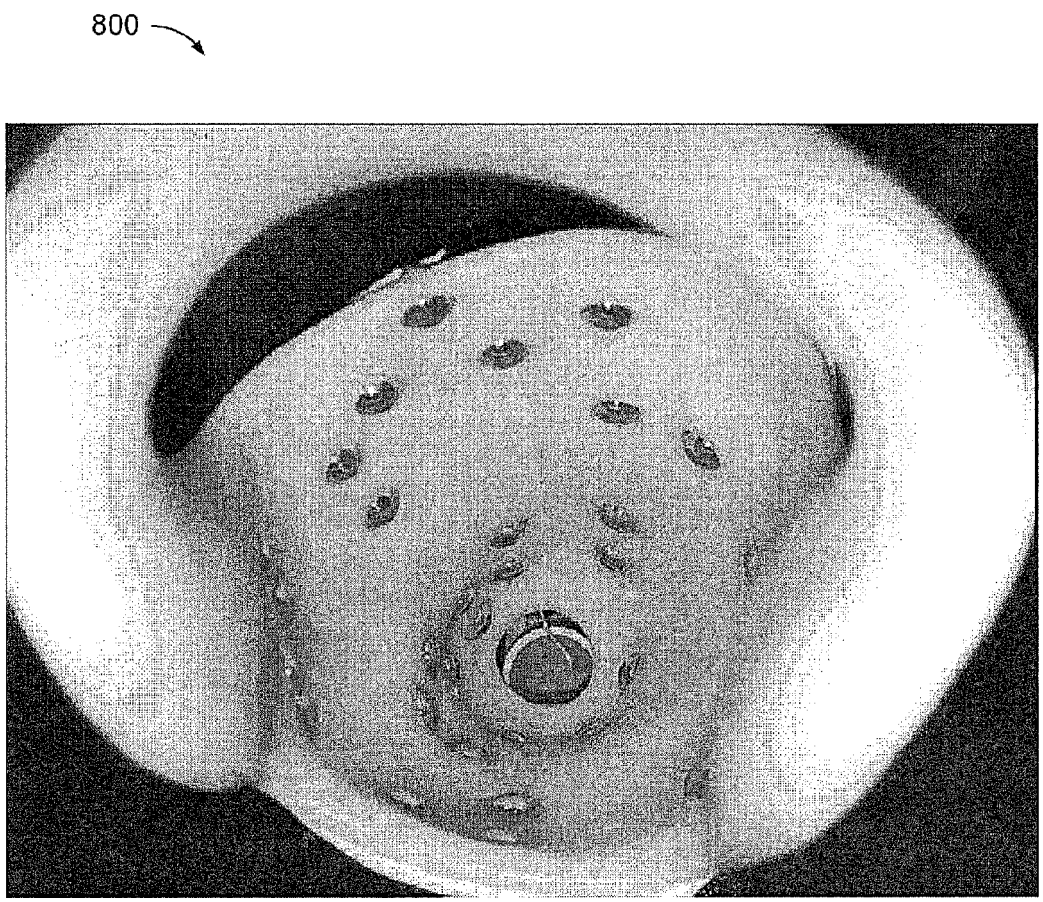
FIG. 8 is an image of a surface EMG recording dome, including electrodes integrated within a socket.

FIG. 8 is an image of a surface EMG recording dome 800, including electrodes integrated within a socket.

(ii) Tactor Subsystem

Tactors provide sensory feedback to users through non-invasive sensory stimulation. A tactor subsystem may include a tactor MHW component that includes an actuator, a tactor controller HW component that contains electronics and circuitry to control the actuator, and a tactor controller SW component to translate percepts supplied by a NFU to actuator commands.

A tactor may be configured to provide mechanical stimuli, which may include tactile, vibratory, and/or thermal stimuli.

Multiple tactor subsystems may be coordinated to deliver relatively complex sensory stimuli. Coordination may be controlled at a NFU level. Tactor subsystem components may be physically attached to the socket.

Figure 9:
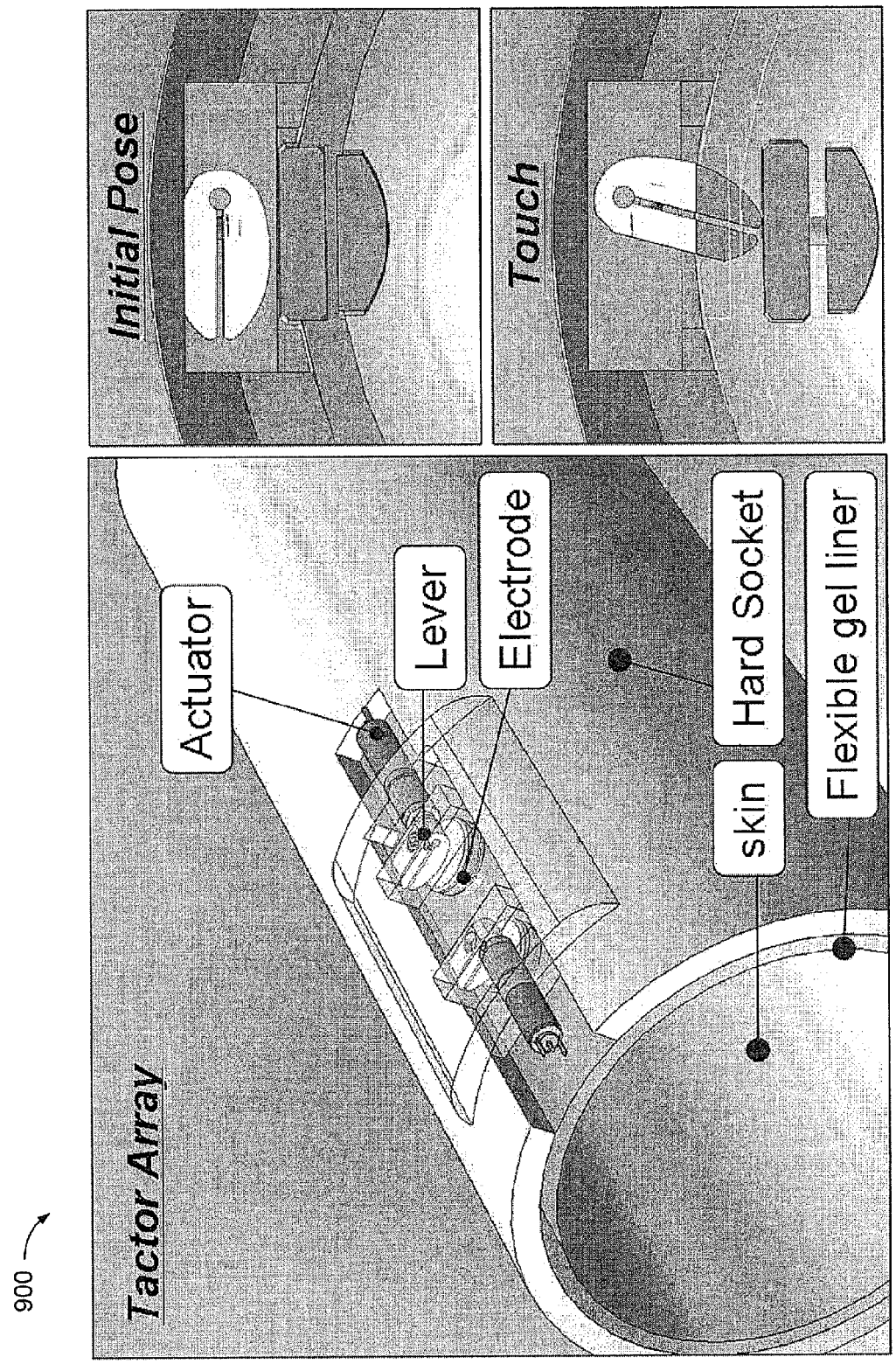
FIG. 9 is a perspective view of a socket, including a mechanical tactor integrated therein and EMG electrodes to effectuate tactor actions.

FIG. 9 is a perspective view of a socket 900, including a mechanical tactor integrated therein and EMG electrodes to effectuate tactor actions.

(iii) Implantable MyoElectric Sensor (IMES) Subsystem

Figure 10:
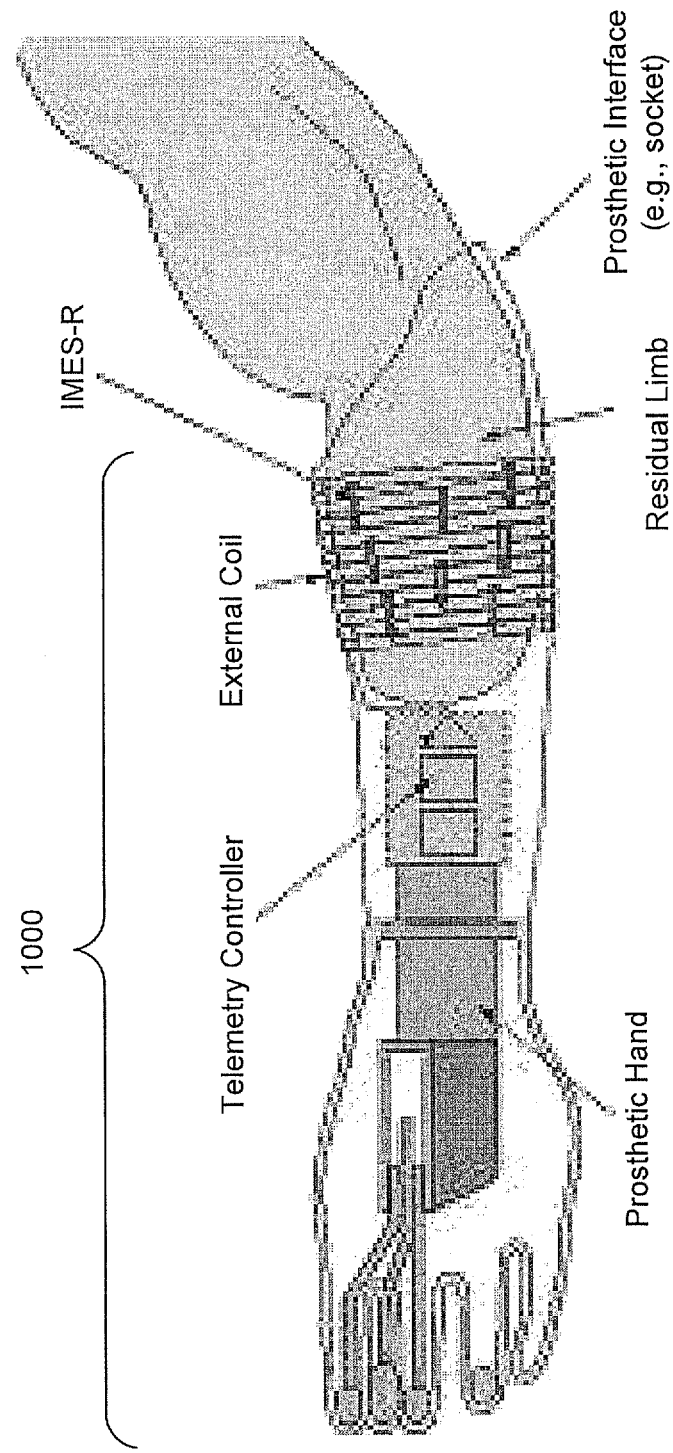
FIG. 10 is a graphic depiction of an IMES subsystem in conjunction with a prosthetic hand.

FIG. 10 is a graphic depiction of an IMES subsystem 1000 in conjunction with a prosthetic hand. IMES subsystem 1000 may be configured as a relatively minimally-invasive mechanism to record relatively high-resolution intramuscular EMG signals. IMES subsystem 000 may include one or more IMES-R wireless implantable EMG recording devices, and an MES telemetry controller (IMES-TC) to communicate with IMES recorder (IMES-R).

The IMES-TC may include an electronic components subassembly to modulate and demodulate wireless power, commands, and data, and may include a subassembly to house RF coils and antennas. The electronic components may be implemented within a printed circuit board, which may be physically housed in the socket. RF coils and antennas may be physically housed in an armband. Additional processing and control of IMES subsystem 1000 may be performed by a NFU.

(iv) Utah Slanted Electrode Array for Recording (USEA-R)

A USEA-R is a moderately-invasive wireless implantable device to record neural activity from peripheral nerves. A USEA-R may include a passive mechanical array of, for example, 100 penetrating electrodes of varying heights, and an active electronics assembly based round an application-specific integrated circuit (ASIC) microchip to harvest power from an externally-applied inductive field, record neural signals from multiple electrodes, perform signal analysis tasks, and transmit processed data off-chip using wireless telemetry. Control of a SEA-R and decoding of USEA-R data to determine a user's intended movements may be performed by a MCU.

(v) Utah Slanted Electrode Array for Stimulation (USEA-S)

A USEA-S is a moderately-invasive wireless implantable device to stimulate individual axons in peripheral nerves. A USEA-S may include a passive mechanical array of, for example, 100 penetrating electrodes of varying heights, which may be similar to an array of a USEA-R. A USEA-S may include an active electronics assembly based around an ASIC microchip to harvest power and receive stimulation commands from an externally-applied inductive field, and to generate independent constant-current stimulation pulses for the electrodes. Control of USEA-S and encoding of sensory feedback from a PL to commands compatible with the USEA-S may be performed by a MCU.

(vi) Epidural ElectroCorticoGraphy Grid (ECoG-R)

An ECoG-R is a relatively highly-invasive wireless implantable device to record electrocorticographic signals from the brain. An ECoG-R may include a passive grid of, for example, 64 epidural surface electrodes, and an active electronics assembly based around an ASIC microchip to harvest power from an externally-applied inductive field, record and digitize CoG signals from electrodes, and transmit data off-chip using wireless telemetry. Control of an ECoG-R and decoding of ECoG-R data to determine the user's intended movements may be performed by a MCU.

(vii) Utah Electrode Array for Recording (UEA-R)

A UEA-R is a relatively highly-invasive wireless implantable device to record neural activity from the cortex. A UEA-R may include a passive mechanical array of, for example, 100 penetrating electrodes, and an active electronics assembly based around an ASIC microchip to harvest power from an externally-applied inductive field, record neural signals from electrodes, perform analysis tasks, and transmit processed data off-chip using wireless telemetry. Control of the UEA-R and decoding of UEA-R data to determine the user's intended movements may be performed by a MCU.

(viii) Utah Electrode Array for Stimulation (UEA-S)

A UEA-S is a relatively highly-invasive wireless implantable device to stimulate individual neurons in the somatosensory cortex. A UEA-S may include a passive mechanical array of, for example, 100 penetrating electrodes, which may be similar or identical to an array used in a UEA-R. A UEA-S may include an active electronics assembly based around an ASIC microchip to harvest power and receive stimulation commands from an externally-applied inductive field, and to generate independent constant-current stimulation pulses for the electrodes. Control of the UEA-S and encoding of sensory feedback from the PL into commands compatible with the UEA-S may be performed by a MCU.

(ix) (Floating Microelectrode Array for Recording (FMA-R)

A FMA-R is a relatively highly-invasive wireless implantable device to record neural activity from the cortex. A FMA-R may include a passive mechanical array of, for example, 64 penetrating electrodes, and an active electronics assembly based around an ASIC microchip to harvest power from an externally-applied inductive field, record neural signals from up to, for example, 100 electrodes, perform signal analysis tasks, and transmit processed data off-chip using wireless telemetry. Control of a FMA-R and decoding of FMA-R data to determine the user's intended movements may be performed by a MCU.

(x) Floating Microelectrode Array for Stimulation (FMA-S)

A FMA-S is a relatively highly-invasive wireless implantable device to stimulate individual neurons in the somatosensory cortex. A FMA-S may include a passive mechanical array of, for example, 64 penetrating electrodes, and an active electronics assembly based around an ASIC microchip to harvest power and receive stimulation commands from an externally-applied inductive field, and to generate independent constant-current stimulation pulses for up to, for example, 100 electrodes. Control of a FMA-S and encoding of sensory feedback from a PL into commands compatible with the FMA-S may be performed by a MCU.

(e) Supporting Hardware and Software

Example supporting hardware and software are disclosed below.

(i) Neural Fusion Unit (NFU) HW/SW

A NFU may serve as a central communications and processing hub of a NI, and may be provided with multiple NI configurations. A NFU may include attachments to provide additional functionality to communicate with the user's nervous system through one or more available neural interface devices.

A NFU may be configured to accommodate, for example, zero or one IMES systems, zero or one CPC headstages, zero to eight tactor controllers, and zero to two MCUs. A NFU may provide a relatively high-speed wireless link to stream data out of a NI, such as for training purposes and/or as a gateway for commands sent from a VIE to a LC. Physical placement of NFU HW may vary for different limb configuration. NFU HW may be housed in a socket.

NFU HW may be configured to perform one or more of the following functions:
 decode motor data from CPC to formulate local decisions;
 decode motor data from the IMES subsystem to formulate local decisions;
 fuse decisions from CPC, IMES, a multi-BID subsystem and a multi-PID subsystem to formulate actions;
 communicate user-desired actions to the PL;
 route sensory data received from the PL to available sensory stimulation feedback channels;
 encode percepts for tactor stimulation; and
 provide a wireless gateway for other portions of the PL system.

(ii) Multi-modal Control Unit (MCU) HW/SW

A MCU serves as a gateway between a NFU and moderately and highly-invasive wireless implantable devices.

Multiple MCU-compatible devices may share a wireless interface.

Multiple implants may be controlled from and may communicate with the same MCU.

Relatively substantial energy levels may be needed to power implantable devices through skin and bones and to support computational efforts of motor decoding algorithms. The MCU may thus include a power source. To manage size and weight of the PL, MCU HW may be housed in a separate unit that attaches to NFU HW via a physical connection, rather than on the limb or in the socket.

MCU HW for use in a multi-BID subsystem and a multi-PID subsystem may utilize different antenna designs to accommodate wireless communications with corresponding implanted neural devices.

Algorithms hosted by MCU SW may differ for peripheral and cortical applications, which may be accommodated with corresponding code images and/or similar codeimages and configurable parameters.

MCU HW/SW may be configured to perform one or more of the following:
 generate electromagnetic fields to supply wireless power and transmit commands to implantable devices;
 receive and demodulate wireless data received from implantable devices;
 decode motor data from implantable recording devices to formulate local decisions; and
 encode percepts for implantable stimulation devices into activation patterns.

Headcap MHW and armband MHW may share the same connector on MCU HW.

(iii) Conventional Prosthetic Controls (CPC) Headstage HW/SW

CPC headstage HW may include amplifiers, analog-to-digital converters, and other electronics to record from conventional prosthetic controls. CPC headstage SW may package and transmit CPC data to the NFU. Physical placement of the CPC headstage HW may vary depending upon limb configuration. CPC headstage HW may be housed in socket.

(iv) Headcap MHW

Headcap MHW is a mechanical device that may physically house antennas associated with a multi-BID MCU implementations, and which may be worn on a user's head.

(v) Armband MHW

A NI may include two types of armband MHW, one each for a multi-PID MCU and an IMES subsystem. Both types of armband MHW may be mechanical devices that physically house antennas. A MPID-type armband MHW may house antennas supplied by a multi-PID MCU. An IMES-type armband MHW may house antennas supplied by an IMES system. Both Armband MHW types may be worn on a user's residual limb. Depending on the user's amputation level and implant site, the armband MHW may be integrated with the socket or may be a separate entity.

(f) System Interfaces

Figure 11:
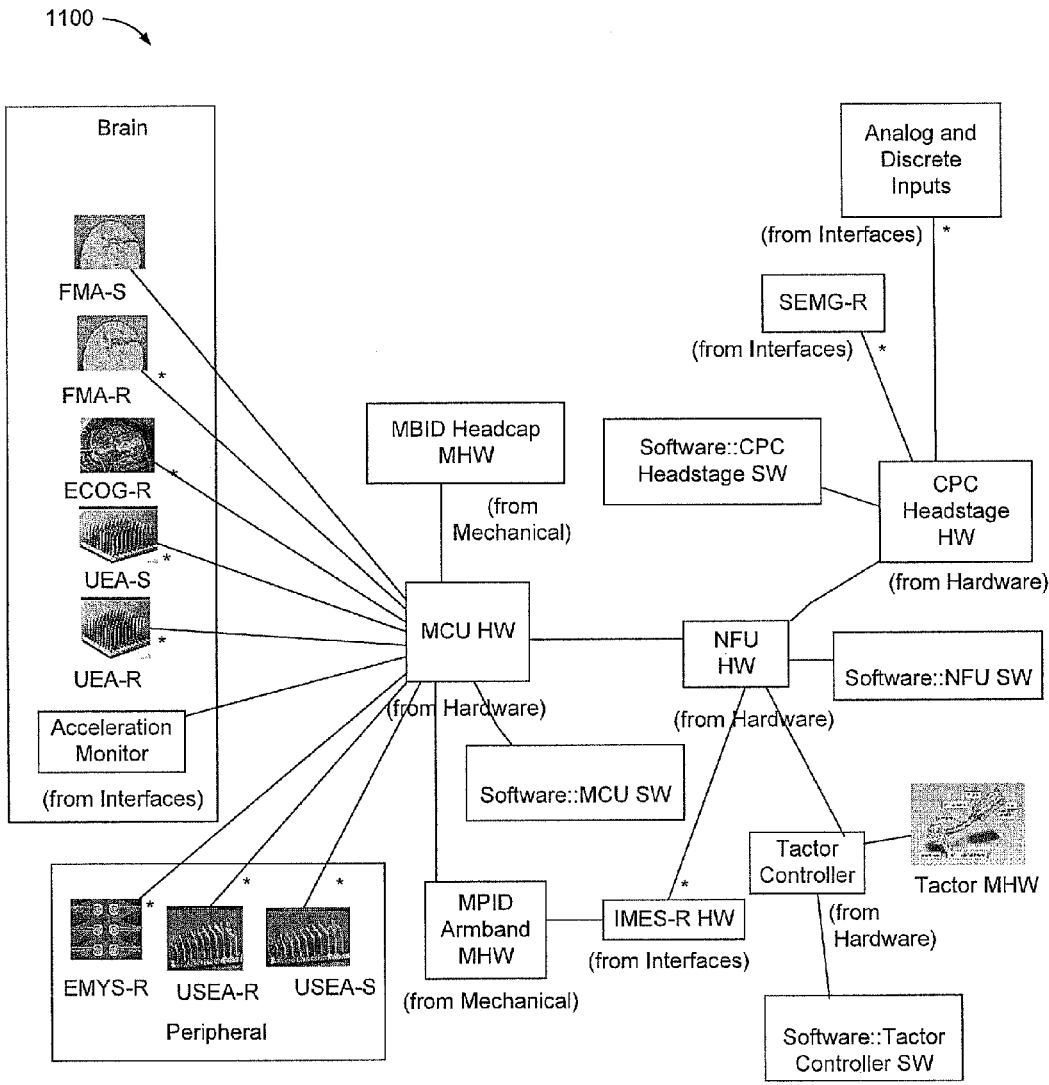
FIG. 11 is a graphic illustration of example internal interfaces between components of a NI.

FIG. 11 is a graphic illustration of example internal interfaces 1100 between components of a NI.

Figure 12:
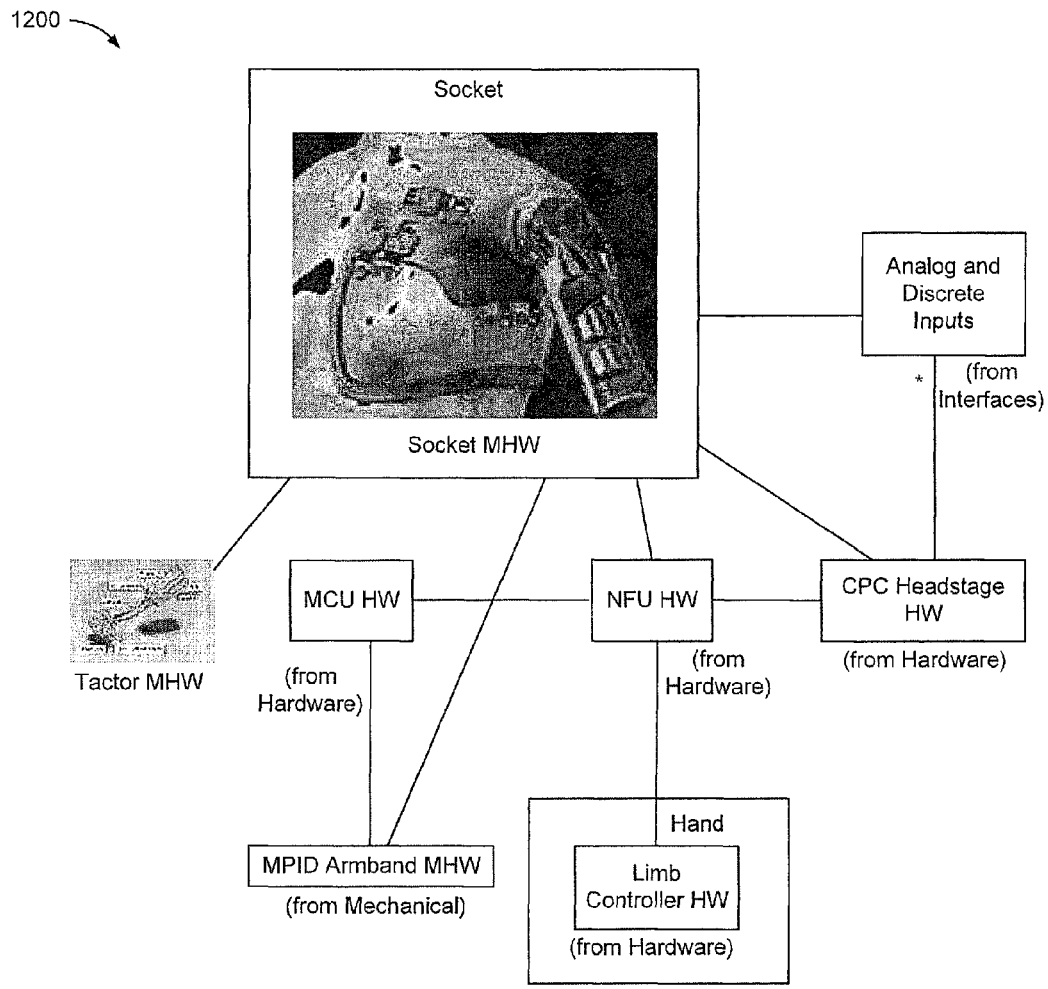
FIG. 12 is a graphic illustration of example external interfaces between a NI and other PL system components.

FIG. 12 is a graphic illustration of example external interfaces 1200 between a NI and other PL system components.

(g) System Architecture

As described above, a NI may be implemented in a modular fashion, which may be useful to isolate potential FDA Class II devices from potential FDA Class III devices, and/or to accommodate users with different injury types and different levels of tolerance for, and/or interest in implantable devices.

A NI may include a base configuration with non-invasive neural devices, supporting hardware and software, and infrastructure to communicate with other components. Such functions may be provided by a NFU, a CPC Headstage, and a tactor subsystem. A base configuration may correspond to an FDA Class II system.

The base configuration may be supplemented with one or more modular additions, which may include one or more of a multi-BID, multi-PID, and IMES subsystems. The one or more modular additions may correspond to FDA Class III devices.

Tasks or labor may be apportioned or divided amongst a NFU and a MCU to accommodate one or more considerations, such as modularity and/or power requirements.

For example, system requirements for total limb weight and number of battery changes per day may reduce or limit the total amount of power available to the NI from the main system battery. A single cortical (UEA-R/S, FMA-R/S, or ECoG-R) or peripheral nerve (USEA-R/S) implant may, however, utilize much less power. A multi-BID or multi-PID subsystem may thus be configured to operate off of the system battery. Additionally, motor decoding and sensory encoding algorithms for cortical and peripheral nerve devices may utilize relatively much more processing power than those for CPC and tactor MHW. One or more multi-BID/PID support functions may be implemented by the MCU rather than the NFU to the MCU, and the MCU may be implemented apart from the main system and may be provided with a separate power supply, such as in a container unit physically separate from the PL.

Since IMES-R implants require only a minimally-invasive surgical procedure, a PL user may be more willing to utilize an IMES subsystem, as compared to multi-BID and multi-PID subsystems. An IMES-TC may utilize a relatively substantial amount of power, while IMES decoding algorithms may be relatively significantly less demanding than multi-BID/PID algorithms and may be substantially functionally equivalent to decoding algorithms for surface EMGs. As part of a base configuration, EMGs may run on the NFU. The IMES subsystem may be separated from the base configuration as a potential FDA Class III device, a socket may accommodate the IMES-TC as a modular attachment, the NFU may host the IMES decoding algorithms, and the IMES subsystem may be powered by the main system battery. Such an implementation may facilitate integration of the IMES subsystem with the PL and NI.

(h) Wireless Calibration Link

A communication channel may be provided between the PL and a virtual integration environment (VIE), such as to configure mechanical components of the PL and algorithms in the NI.

A relatively significant portion of configuration may be performed in a prosthetist's office. A user may, however, have a VIE at home to permit periodic recalibration of motor decoding algorithms. To facilitate user-calibration and to make it as user-friendly as possible, a wireless communication link may be provided from the VIE to the PL. Such a wireless link may be provided by one or more of a variety of PL components and may utilize off-line or buffered data. The VIE may, however, have real-time access to all of, or substantially all of an entire volume of neural data collected by the NI. This may facilitate efficient calibration of motor decoding algorithms.

Where a bus linking the NFU to the LC is relatively limited in bandwidth, a wireless network may be implemented within the NI.

Where the NI is to be configurable even where only non-invasive SEMG recording devices are available, the wireless link may be implemented as part of the NI base configuration, and may be implemented on the NFU.

(i) Neural Toolkit

A NI may be designed, configured, and/or implemented with or as a neural toolkit to support a relatively wide variety of devices from which a user may select one or more tools to suit the user's particular level of injury and willingness to undergo invasive surgical procedures. A neural toolkit may include best-of-breed technologies selected from multiple classes of devices, which may range from relatively non-invasive to relatively highly-invasive. A neural toolkit may include devices that provide complimentary functionality, such that a user can expect increased sensory or motor performance from the PL with each additional implant. Example devices may include one or more neural recording devices and/or one or more neural stimulation devices.

A neural toolkit may include one or more of the following neural recording devices:
    SEMG (spatially- and temporally-averaged activity from multiple muscles);
    IMES-R (locally-averaged activity from individual muscles);
    USEA-R (high-resolution activity from individual α-motor neurons);
    ECoG-R (low-resolution information about endpoint location and movement intention);
    UEA-R (high-resolution goal information; information about endpoint location, movement intention, and upper-arm movements); and
    FMA-R (high-resolution information about endpoint location and finger movements).

Alternatively, or additionally, a neural toolkit may include, for example, one or more of the following neural stimulation devices:
    tactor MHW (low spatial and temporal resolution tactile and proprioceptive percepts; grasp confirmation);
    USEA-S (high spatial and temporal resolution tactile percepts);
    UEA-S (proprioceptive percepts); and
    FMA-S (coherent tactile percepts on individual fingers).

An MCU HW/SW may be implemented to be compatible with one or more of a variety of neural interface devices that conform to a communications protocol. For example, MCU HW/SW may be configured to accommodate a device based on an Integrated Neural Interface (INI) technology developed by Reid Harrison at the University of Utah. There are currently two main types of INI chips, one each for recording and stimulation.

Figure 13:
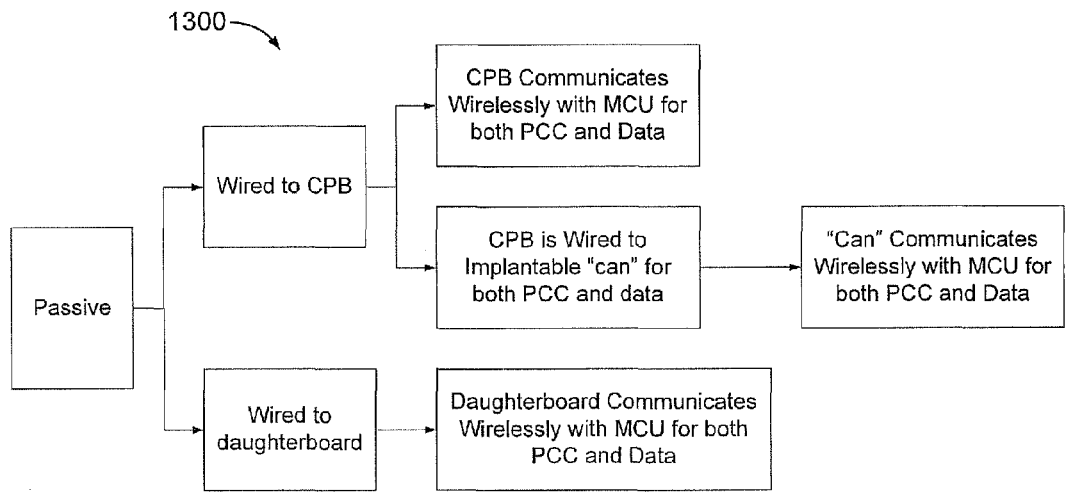
FIG. 13 is a block diagram of a neural device implantation architecture.
Figure 14:
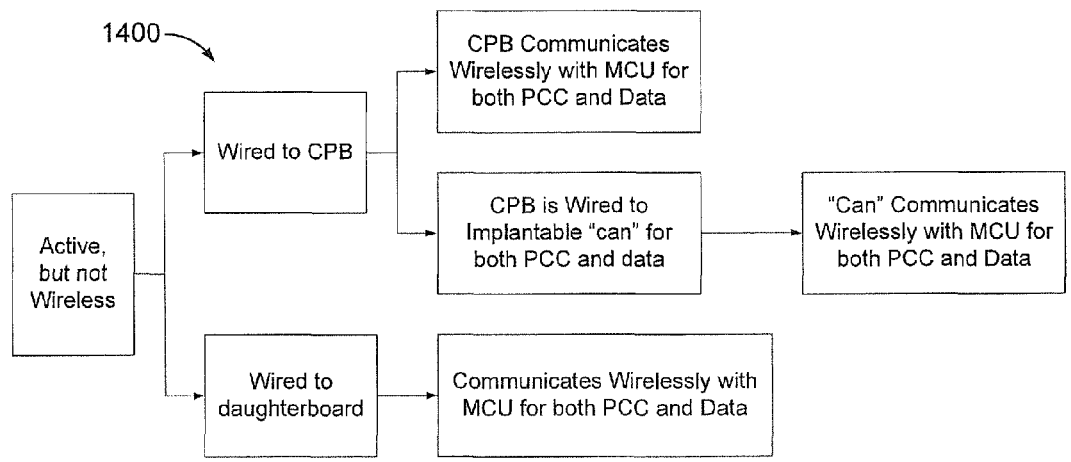
FIG. 14 is a block diagram of a neural device implantation architecture.
Figure 15:
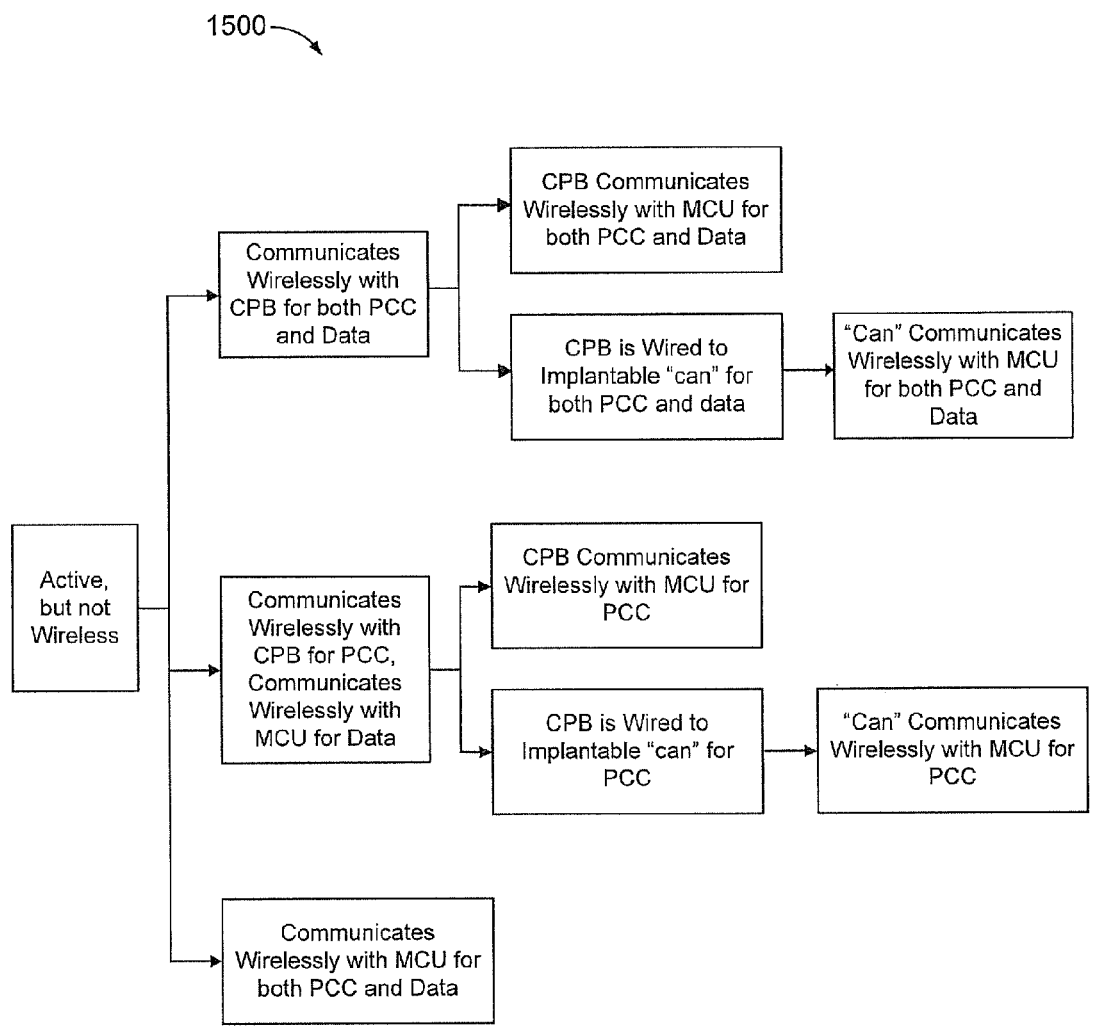
FIG. 15 is a block diagram of a neural device implantation architecture.

FIGS. 13, 14, and 15 are block diagram of example neural device implantation architectures, 1300, 1400, and 1500, respectively. In FIGS. 13, 14, and 15, "CPB" refers to a central processing board, which may host all or substantially all active electronics for an entire multi-BID and/or multi-PID subsystem. In FIGS. 13, 14, and 15, "PCC" refers to power, clock, and commands.

(j) Implant Locations

Depending on a user's level of amputation, IMES-R and USEA-R/S devices may be implanted in one or more of multiple locations. For example, a transradial amputee may have IMES-R and/or USEA-R/S devices implanted in the forearm, upper arm, and/or chest/brachial plexus level. While a NI system architecture may support all of these implant locations, there may be wireless coil and socket design considerations for each location. To ensure that resources are optimally allocated, surgeons and prosthetists were consulted to determine the most likely implant scenarios, as illustrated in the table immediately below.

| Injury Type | SEMG | IMES | Tactor | USEA | FMA | UEA | ECoG |
|---|---|---|---|---|---|---|---|
| Shoulder Disarticulation | Chest | Chest* | Chest | Chest* | PRR/S1/M1 | M1/PM/S2 | M1/PM/S2 |
| Transhumeral Amputation | U Arm | U Arm* | U Arm | U Arm* | PRR/S1/M1 | M1/PM/S2 | M1/PM/S2 |
| Elbow Disarticulation | U Arm | U Arm* | U Arm | U Arm* | PRR/S1/M1 | M1/PM/S2 | M1/PM/S2 |
| Transradial Amputation | L Arm | L Arm | L Arm | U Arm | | | |
| Wrist Disarticulation | L Arm | L Arm | L Arm | U Arm | | | |

In the table above, "L Arm" refers to lower arm, "U Arm" refers to upper arm, "PRR" refers to parietal reach region, "S1" refers to primary somatosensory cortex, "M1" refers to primary motor cortex, "PM" refers to pre-motor cortex, and "S2" refers to secondary somatosensory cortex. An asterisk indicates that the devices may be supported, but may not be accommodated simultaneously at the same location.

IMES-R devices may be supported in the forearm of transradial and wrist disarticulation amputees, the upper arm of transhumeral and elbow disarticulation amputees, and in the chest of shoulder disarticulation amputees with targeted muscle reinnervation (TMR).

USEA-R/S devices may be supported in the upper arm of transradial, wrist and elbow disarticulation, and transhumeral amputees, and in the chest of shoulder disarticulation amputees with TMR.

FMA-R/S, UEA-R/S, and ECoG-R devices may be supported for shoulder disarticulation, transhumeral, and elbow disarticulation amputees.

IMES-R and USEA-R/S devices may not be simultaneously accommodated at the same location if there is significant radiofrequency interference between the two types of devices.

(k) Algorithm Considerations

Different algorithms may run at different rates. To estimate the computational cost of these algorithms, operations counts may be been separated into units of operations per time step. In a computational cost analysis, estimates of memory requirements may be evaluated, which may include parameters for the algorithms and temporary variables created to hold intermediate calculation results.

Computational costs may be grouped into two categories: algorithms for individual decode of cortical and peripheral nerve signals, which run on the MCUs, and algorithms for fusion and EMG decoding, which run on a NFU.

Figure 16:
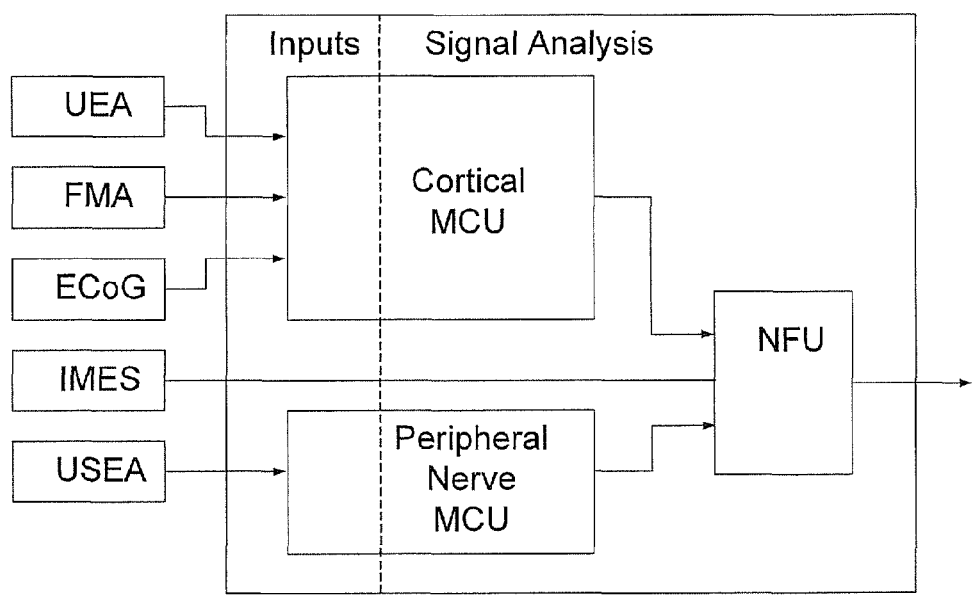
FIG. 16 is a block diagram of a NFU, including motor decoding algorithms and hardware on which the algorithms may execute.

FIG. 16 is a block diagram of a NFU 1600, including motor decoding algorithms and hardware on which the algorithms may execute.

Figure 17:
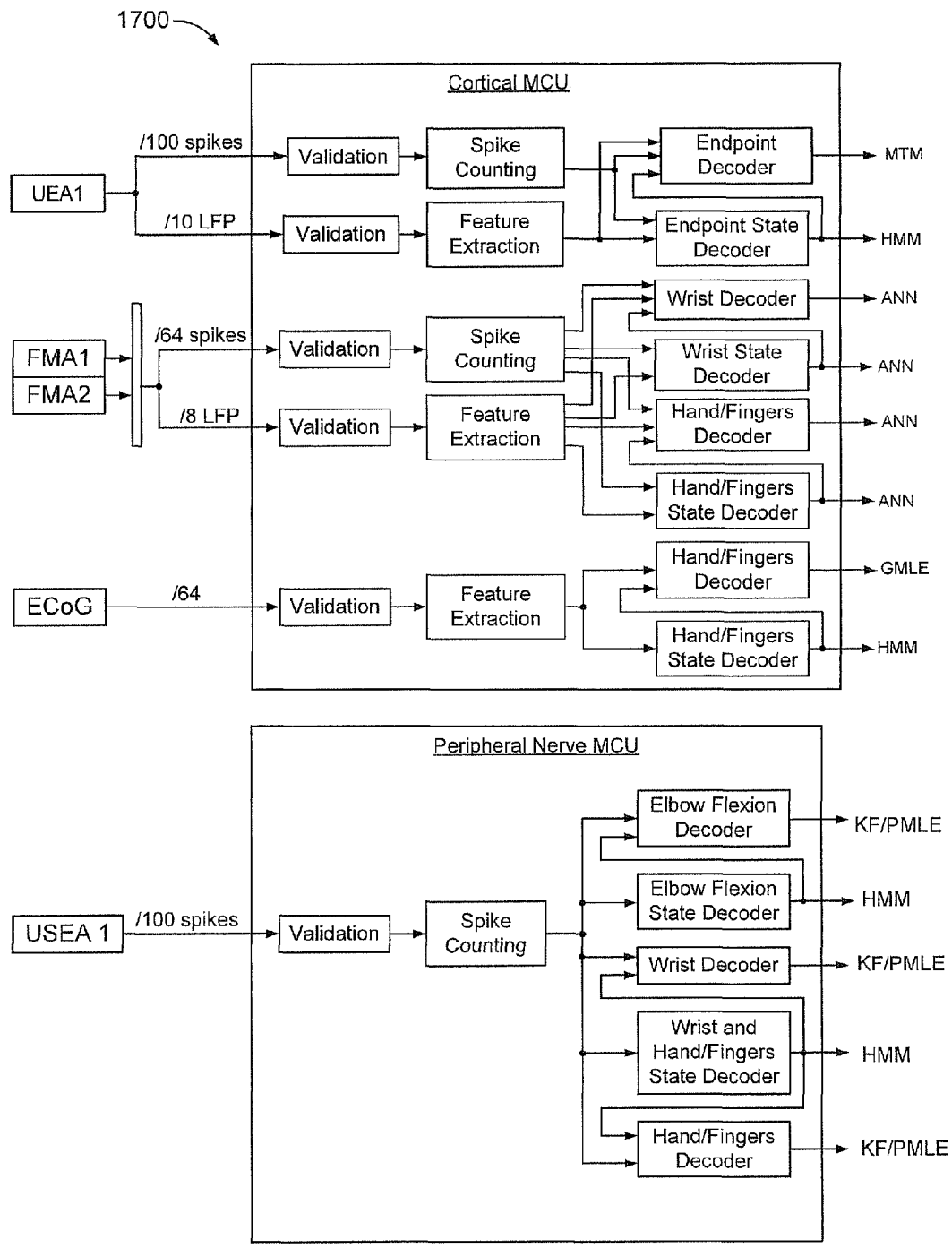
FIG. 17 is a block diagram of motor decoding algorithms for a set of implants, including algorithms that execute on multi-modal control units (MCUs).

FIG. 17 is a block diagram of NI individual motor decoding algorithms for a set of implants, including algorithms that execute on MCUs.

Figure 18:
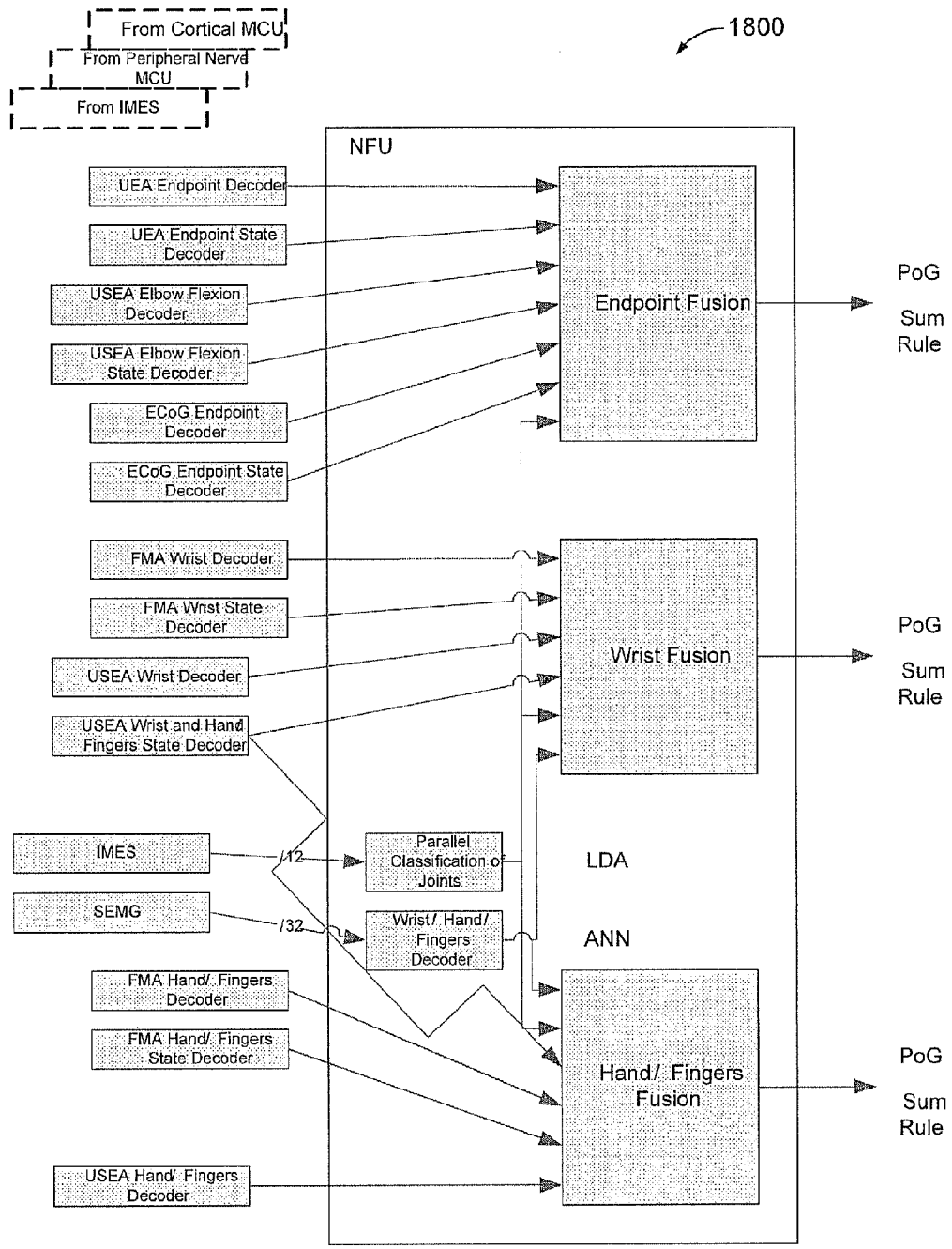
FIG. 18 is a block diagram of fusion algorithms to receive output of the algorithms of FIG. 17, including algorithms running on the NFU of FIG. 16.

FIG. 18 is a block diagram of example fusion algorithms to receive output of the algorithms of FIG. 17, including algorithms running on the NFU.

In FIGS. 17 and 18, "MTM" refers to Mixture of Trajectories Model, "HMM" refers to Hidden Markov Model, "ANN" refers to Artificial Neural Network, "GMLE" refers to Gaussian Maximum Likelihood Estimate, "PMLE" refers to Pseudo-Maximum Likelihood Estimate, "KF" refers to Kalman Filter, "PoG" refers to Product Gaussians, and "LDA" refers to Linear Discriminant Analysis.

Computational costs may be evaluated with respect to one or more of a worst case scenario, a typical case scenario, and an optimal case scenario, which may be distinguished by the number of implants and volume of data. Example computation costs are provided in the table immediately below.

| Operation | Cortical MCU | Peripheral MCU | NFU | TOTAL |
|---|---|---|---|---|
| Scalar + & − [O(n)] | 168,249,692 | 10,092,500 | 400 | |
| Scalar * & ^2 [O(n)] | 10,049,400 | 23,600 | 0 | |
| Scalar/[O(n$^2$)] | 37,400 | 4,800 | 0 | |
| Factorials [O(6)] | 205,800 | 5,000 | 0 | |
| Matrix + [O(n?)] | 0 | 0 | 38,800 | |
| Matrix * [O(nmp)] | 161,883,400 | 1,977,200 | 701,200 | |
| Matrix Inversion [O(n$^2$)] | 24,773,900 | 1,390,100 | 1,560,000 | |
| Logs [O(nlog(n))] | 29,557,300 | 0 | 0 | |
| Exp [O(nlog(n))] | 182,248,900 | 724,000 | 0 | |
| Max [O(n-1)] | 1,400 | 200 | 0 | |
| Determinants [O(n$^4$)] | 1,456,000 | 0 | 0 | |
| Nonlinear Function Calls [O(log(10$^4$))] | 3,149,400 | 0 | 362,000 | |
| Median Checks [O(nlog(n))] | 0 | 0 | 0 | |
| MIPS | 581.613 | 14.217 | 2.624 | 598.454 |
| Integer Data (16 bits) | 1,804 | 110 | 0 | |
| Float Data (40 bits) | 98,504 | 2,952 | 3,525 | |
| Memory (bits) | 3,969,024 | 119,840 | 141,000 | |
| Memory (KBytes) | 496.128 | 14.98 | 17.625 | 528.73 |

3. Example 2

Pre-Processing, Gating, and Intent Decoding

Methods and systems to pre-process, gate, and decode intent from biological and conventional prosthetic control (CPC) input signals are disclosed below.

Figure 19:
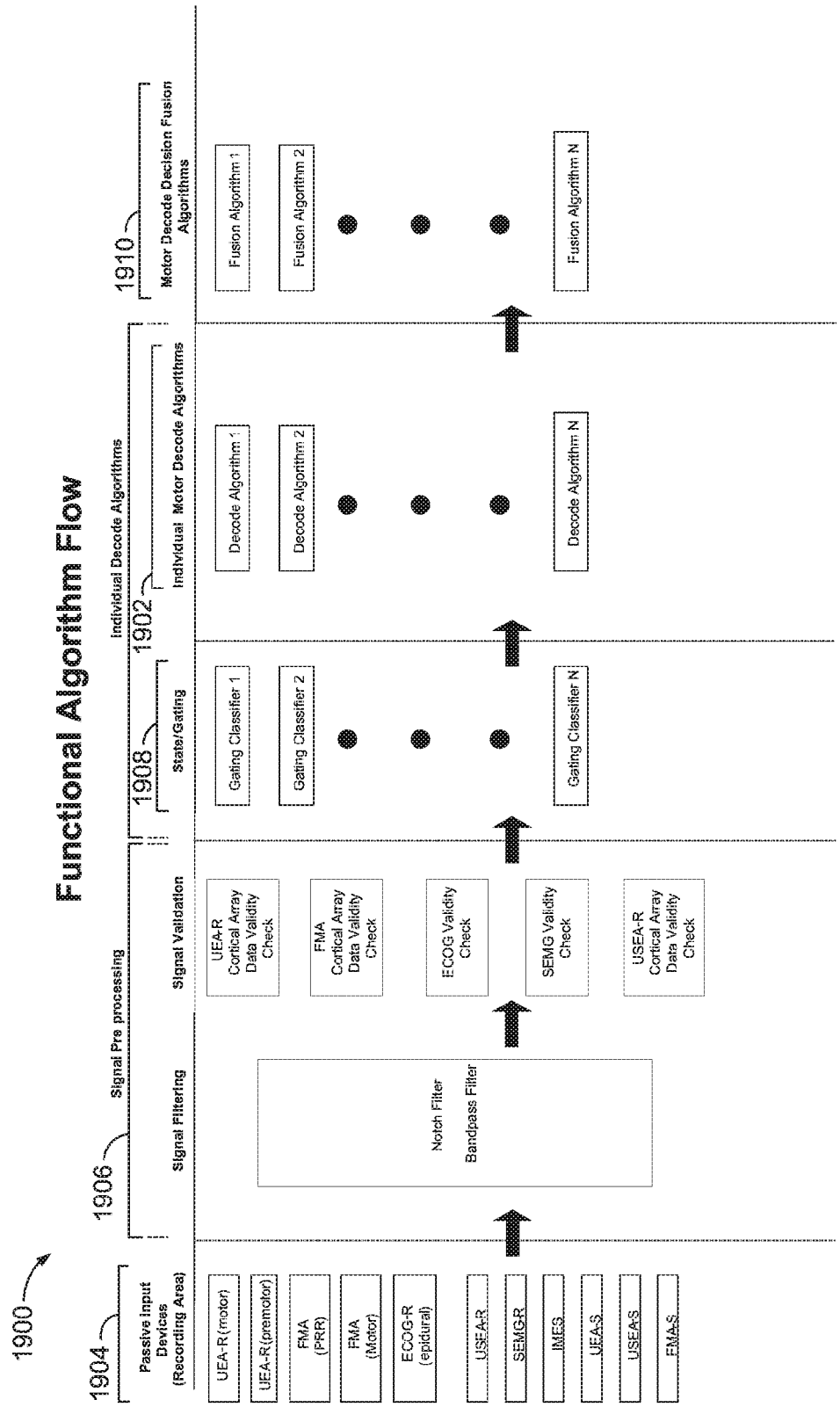
FIG. 19 is a block diagram of an example motor decode engine (MDE), which may be implemented as a software framework within a neural algorithm environment.

FIG. 19 is a block diagram of an example motor decode engine (MDE) 1900, which may be implemented as a software framework within a neural algorithm environment.

MDE 1900 may include one or more decode modules or algorithms 1902 to convert biological and conventional prosthetic control (CPC) input signals to limb commands. This is also referred to herein as decoding user intent.

One or more types of input devices 1904 may be used to record one or more of a variety of biological signals from which intent is to be decoded. Input devices 1904 may include, for example, one or more of floating micro-electrode arrays (FMAs), Utah electrode arrays (UEAs), Utah slant electrode arrays (USEAs), electrocorticogram (ECoG) electrodes, surface electromyogram (sEMG) electrodes, and implantable MyoElectric sensor (IMES) electrodes. In addition to biological signals, conventional prosthetic controls, such as force sensitive resistors and switches, may be used as input signals.

MDE 1900 may receive digitized neural data, which may include one or more of single-unit spike activity, local field potentials (LFP), EcoG signals, electromyogram (EMG) signals, and input from CPCs.

Input signals may be routed over an inputs bus, which may include analog and digital signals and a bit error field. Analog signals may include digitized analog data values. Digital signals may include of binary data values.

MDE 1900 may be organized as a set of subsystems.

MDE 1900 may include a preprocessor 1906 to preprocess input signals.

The preprocessed input signals may be routed to gating algorithms 1908 and, subsequently, to appropriate individual decode algorithms 1902. Outputs of decode algorithms 1902, referred to herein as decisions, may be processed in accordance with decision fusion algorithms 1910. Each instantiation of a decision fusion algorithm 1910 may represent a single group of control and decision space, where the decision space may be continuous or discrete.

A full joint state vector may be estimated in order to completely estimate user-intended motion.

Where a NI is implemented as a modular system, motor decoding algorithms 1902 may also be modular.

Motor decoding algorithms 1902 may run on multiple processors.

Figure 20:
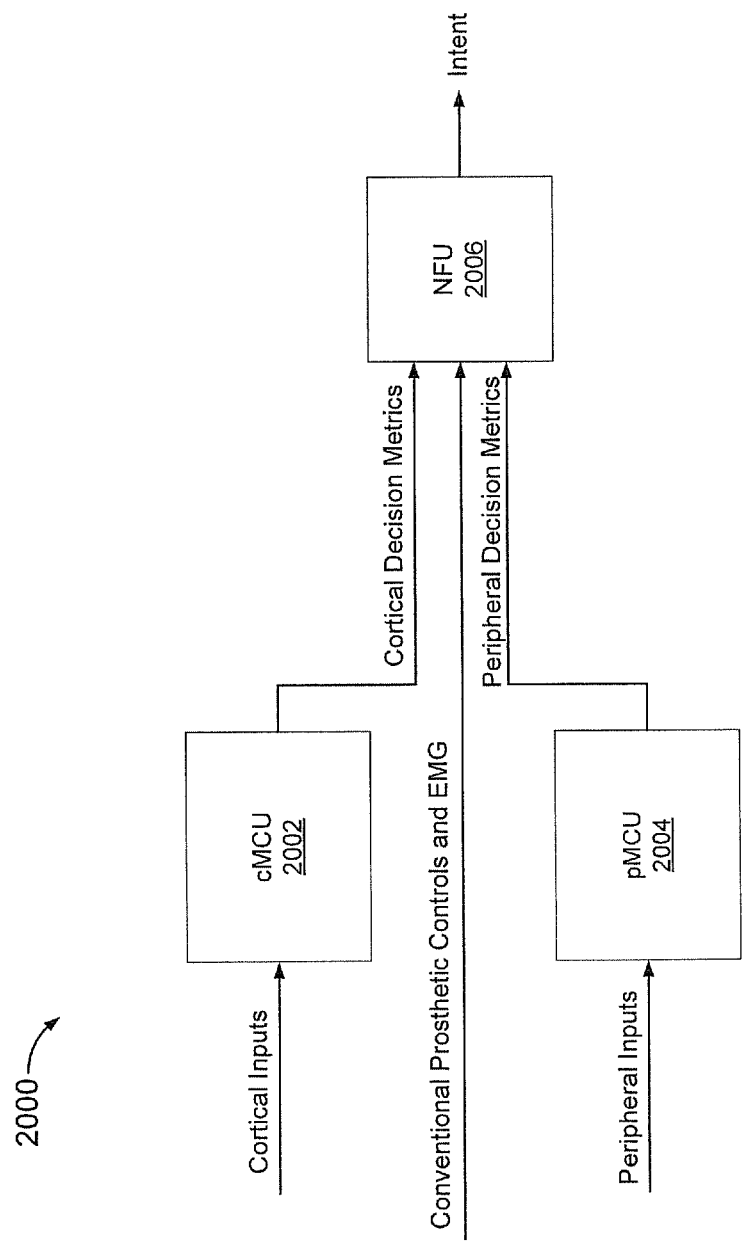
FIG. 20 is a block diagram of a MDE, including three processors, a cortical multimodal control unit (cMCU), a peripheral nerve multimodal control unit (pMCU), and a neural fusion unit (NFU).

FIG. 20 is a block diagram of a MDE 2000, including three processors, a cortical multimodal control unit (cMCU) 2002, a peripheral nerve multimodal control unit (pMCU) 2004, and a neural fusion unit (NFU) 2008.

cMCU 2002 hosts decode algorithms that utilize cortical input signals. pMCU 2004 hosts decode algorithms that utilize peripheral nerve input signals. NFU 2006 hosts decode algorithms that utilize EMG and CPC input signals, and decision fusion algorithms.

Inputs to the decision fusion algorithms may correspond to outputs provided by gating classifiers and individual decode algorithms, depending on which neural recording devices and signal types are available for an individual user. Such partitioning of functionality may facilitate relatively efficient use of each processor and may reduce bandwidth and power requirements of an MCU-to-NFU bus.

Algorithms of a MDE may be provided within a signal analysis block of a virtual integration environment (VIE). The signal analysis block may include infrastructure and interfaces.

Algorithms may be developed from a common template block that includes all or substantially all interfaces that are usable by the embedded system.

A MDE may be configurable during training and during online use.

During training, a clinician may selectively enable and disable algorithms, determine a superset of input signals that map to each individual algorithm, and/or tune algorithm-specific parameters. Algorithm-specific parameters may vary from algorithm to algorithm, and may include, for example, type of firing rate model a decoder assumes, and bin sizes used in collecting spikes. During training, algorithm parameters to be used for decoding, such as neuronal tuning curves, may also be generated.

During run-time, a patient or clinician may configure the motor decode engine. Multiple types of configurations may be supported, which may include turning on or off individual algorithms, switching the mode that an algorithm runs in (if an algorithm supports mode switching), and adjusting gains of decoder outputs. Mode switching may include, for example, switching the type of intent commends, such as from position to impedance, that the MDE sends.

Figure 21:
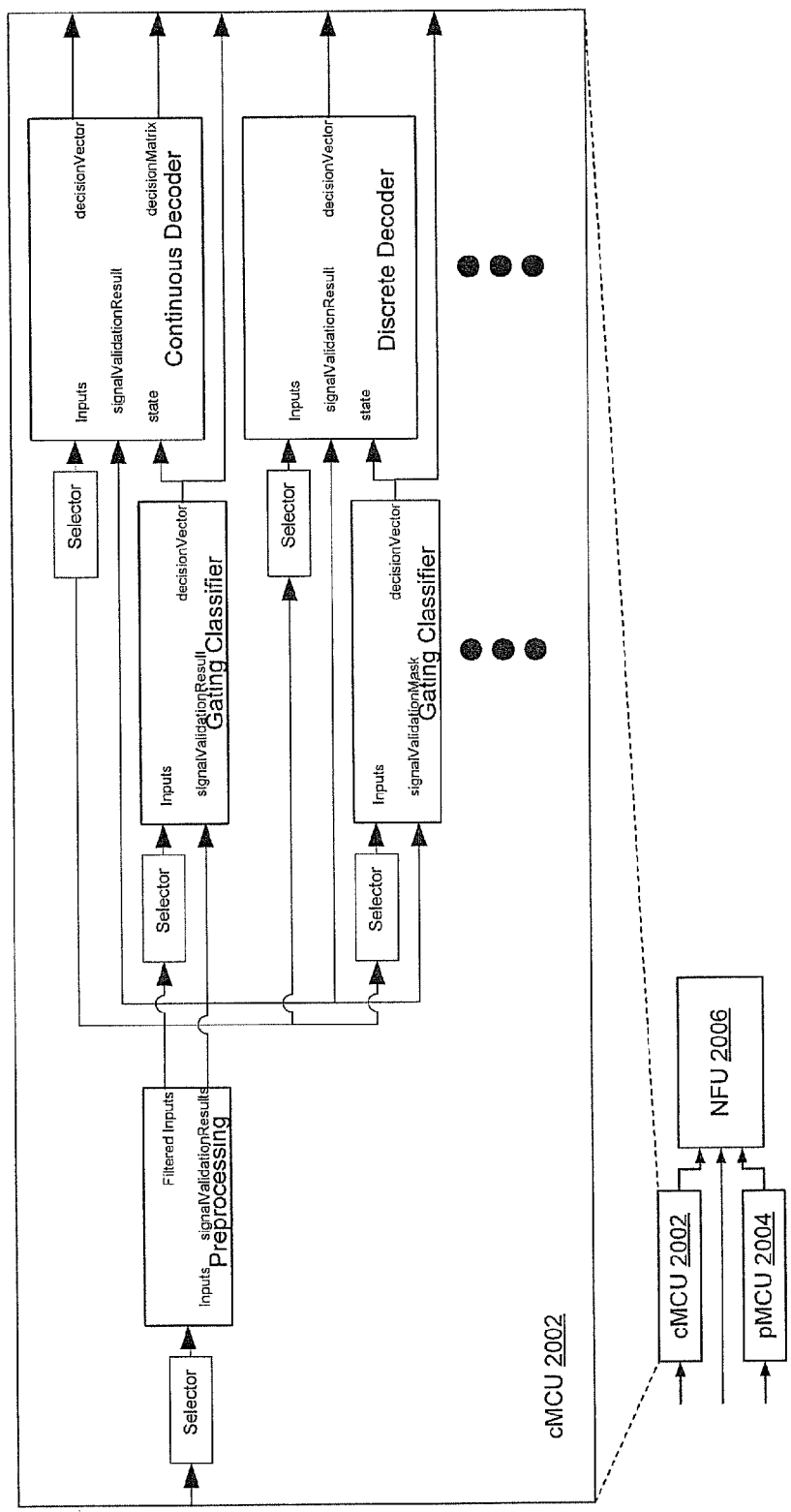
FIG. 21 is a block diagram of the cMCU of FIG. 20, including processes that run thereon.

FIG. 21 is a block diagram of cMCU 2002 of FIG. 20, including processes that run thereon.

Figure 22:
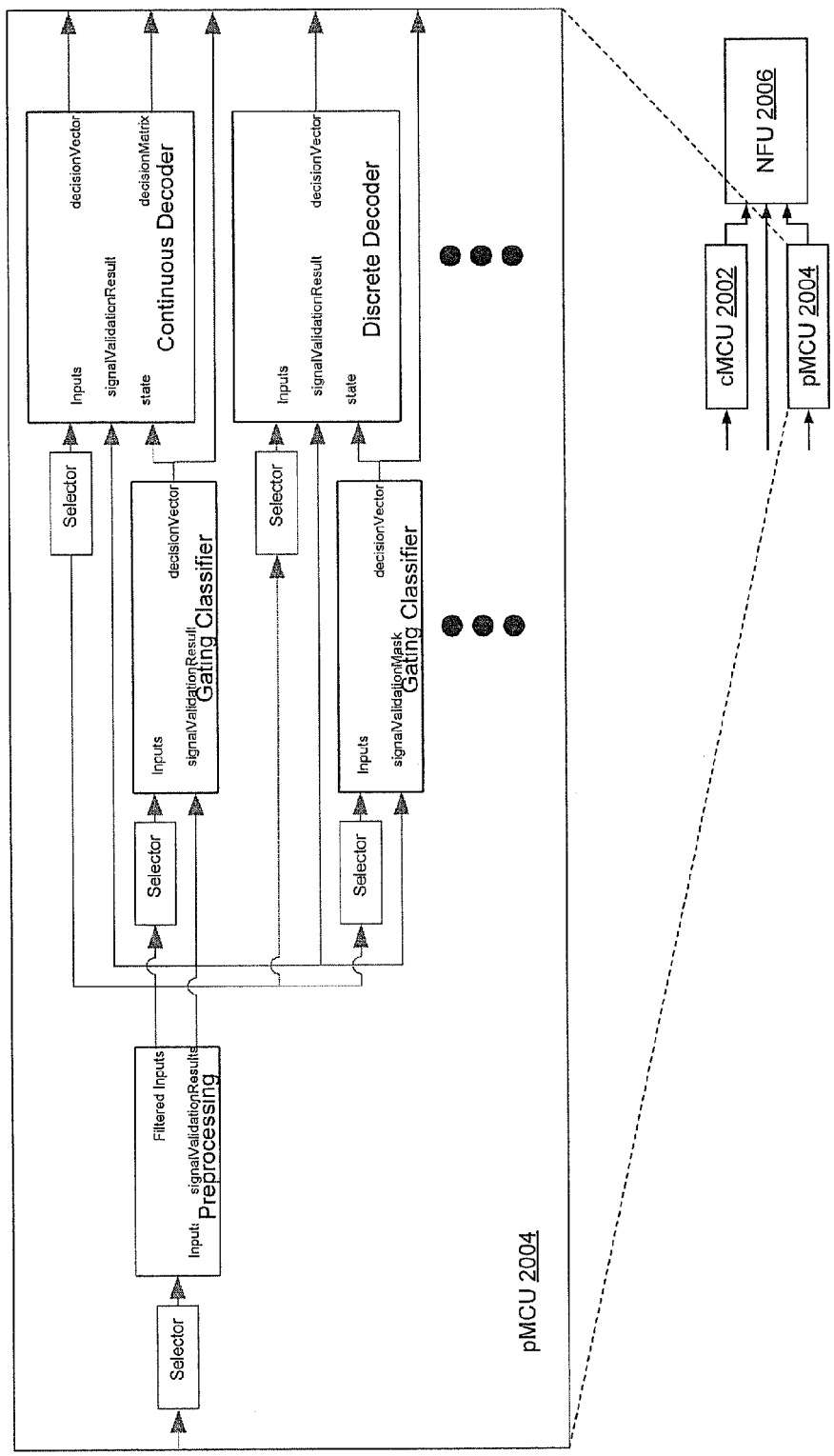
FIG. 22 is a block diagram of the pCU of FIG. 20, including processes that run thereon.

FIG. 22 is a block diagram of pCU 2004 of FIG. 20, including processes that run thereon.

Figure 23:
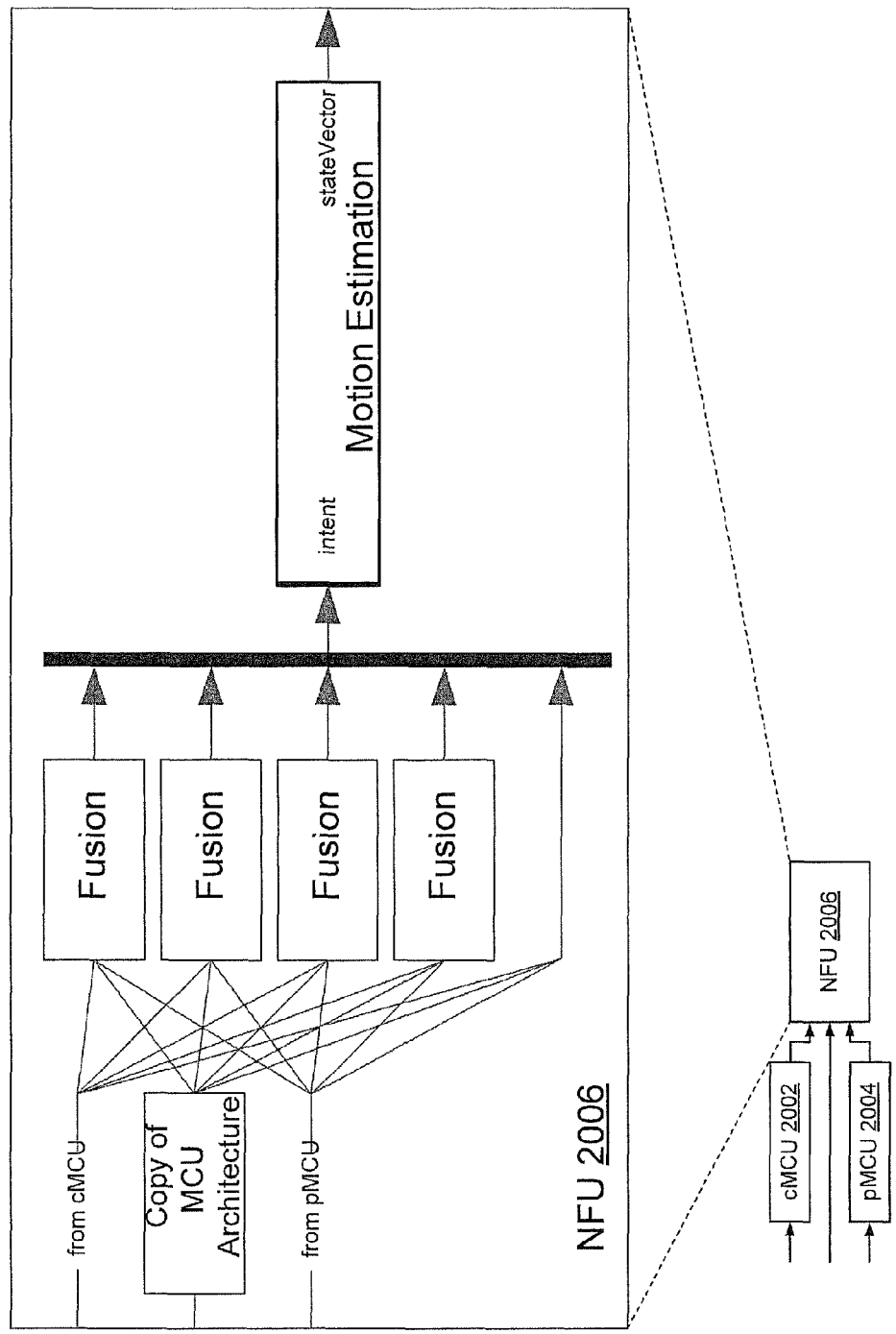
FIG. 23 is a block diagram of the NFU of FIG. 20, including processes that run thereon.
Figure 24:
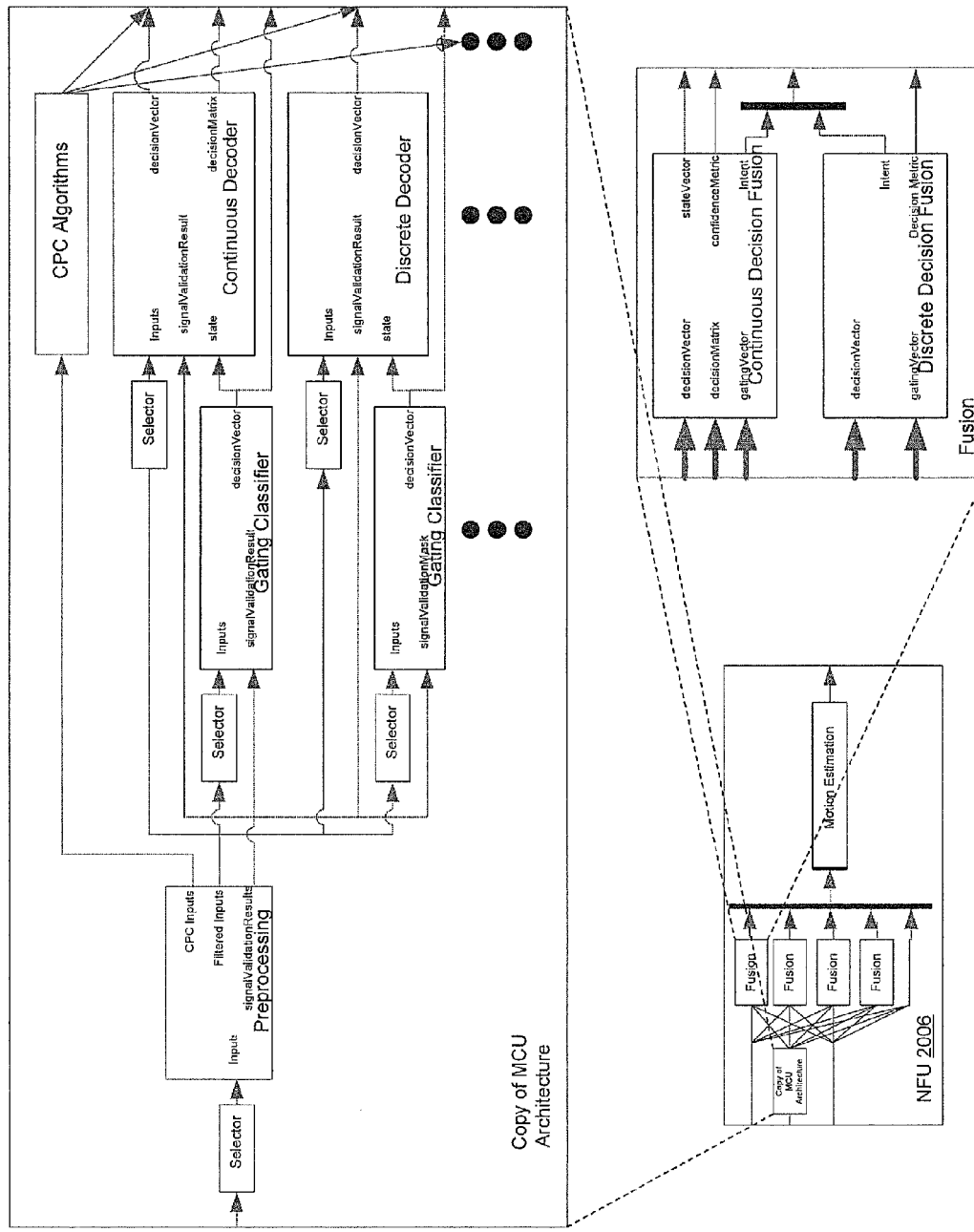
FIG. 24 is another block diagram of the NFU of FIG. 20, including processes that run thereon.

FIGS. 23 and 24 are block diagrams of NFU 2006 of FIG. 20, including processes that run thereon.

Figure 25:
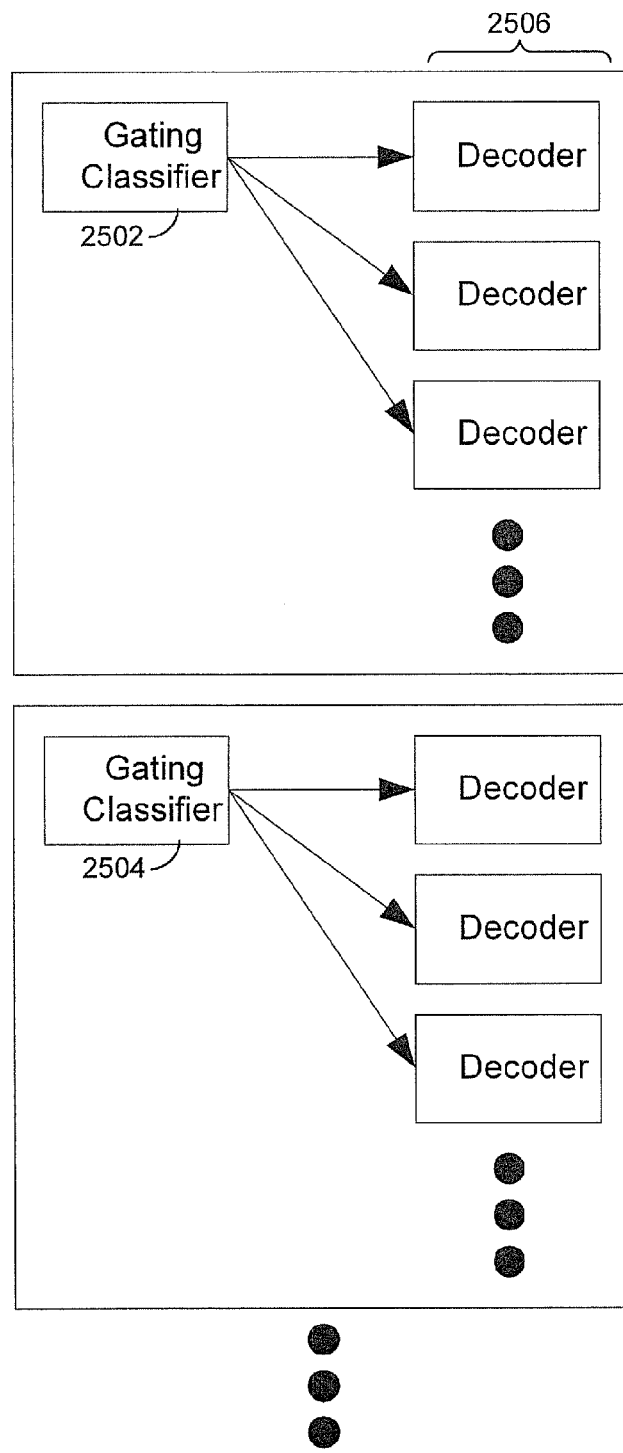
FIG. 25 is a block diagram of example gating classifiers and decoder algorithms.

FIG. 25 is a block diagram of example gating classifiers 2502 and 2504, e.g. gate classifier modules, and decoder algorithms 2506, to illustrate that outputs of gating classifiers may diverge within a group of control and interface with multiple decoders, and to illustrate that the number of gating classifiers may vary. In other words, various numbers of movement decoders may interface with a single gating classifier.

Each gating classifier and movement decoder may use a set or subset of available input signals. An initial selector may be used to discard unused signals, which may reduce the amount of initial processing. The initial selector may select a union of all sets of signals used by all gating classifiers and movement decoders. Preprocessing and other functions may be performed on the selected signals. Subsequent selectors may be included to select subsets of signals that are specific to each gating classifier or movement decoder.

In FIG. 25, ellipses indicate a function or feature that may be repeated, which may be implemented at compile time. The number of gating classifiers and the number of movement decoders may be configurable.

cMCU 2002 and pMCU 2004 may be implemented with frameworks that are similar to one another, with different inputs applied to each of cMCU 2002 and pMCU 2004.

NFU 2006 may be implemented with a similar framework as cMCU 2002 and pMCU 2004, but with different input signals. NFU 2006 may also include a framework to implement decision fusion and state vector estimation. Each fusion block of NFU 2006 may represent a corresponding group of control. A generic group of control may decode ROC ID.

Example subsystems and interfaces of MDE 2000 are described below with respect to FIG. 26.

Figure 26:
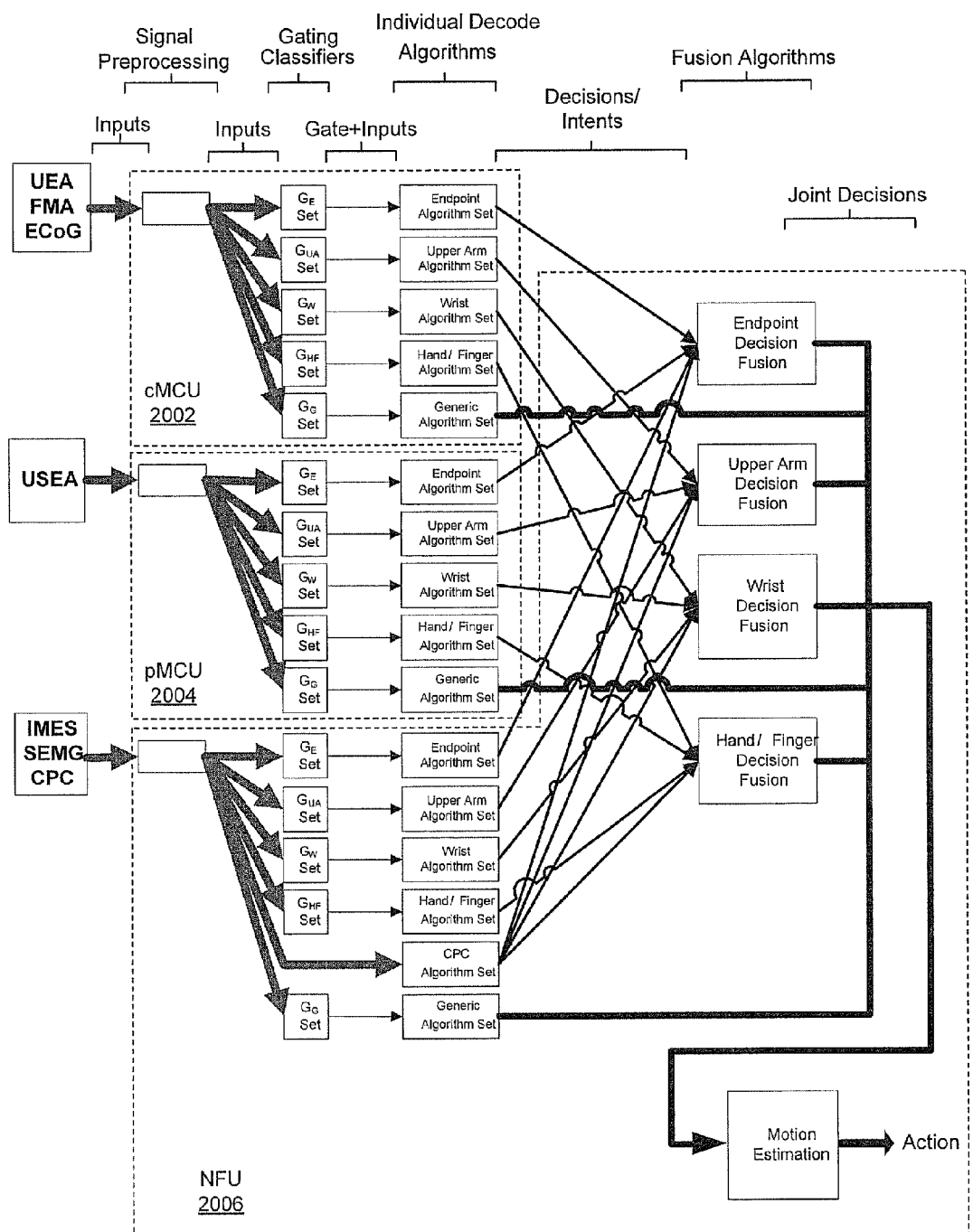
FIG. 26 is a block diagram of another MDE.

FIG. 26 is a block diagram of a MDE 2600. Some features are omitted from FIG. 26 for illustrative purposes, such as connections between gating classifiers and decision fusion.

(a) Preprocessing and Signal Validation

Input signals may be preprocessed in accordance with one or more techniques.

Preprocessing may include digital filtering, which may include, without limitation, all pass filtering.

Preprocessing may include signal validation, which may include signal detection and/or identification of potentially corrupted data. Corrupted data may arise from broken electrodes, poor connections, interference, and/or sensor drift. Resulting signals may have aberrant means, variance, and/or noise characteristics. In addition, some input devices may be permanently implanted, and it may be useful to know whether such a device is operating correctly.

Signal validation algorithms may be provided for specific types of signals to identify potentially corrupted data. Where signal validation algorithms are provided for each type of input signal, preprocessing may be implemented on cMCU 2002, pMCU 2004, and NFU 2006.

Identification of potentially corrupted data may include tagging or flagging data. A flag may include a value to indicate whether a signal is valid, and may include an indication of a stage at which the signal was marked invalid. A set of flags for all signals represent a signal validation result. Identification of potentially corrupted data may render downstream algorithms more efficient and more effective.

Validation algorithms may be implemented to identify or distinguish corrupted signals from uncorrupted signals. Validation algorithms may be also implemented to indicate the type of corruption, which may be used by downstream algorithms to determine whether to use or ignore the data.

Validation algorithms may classify signals as valid or invalid for further processing. Each algorithm may include multiple stages, each of which may flag the signal as invalid or pass the signal to the next validation stage. A signal flagged as invalid in a validation stage may bypass subsequent validation stages.

Validation stages may include one or more general signal analysis techniques with parameters tuned for appropriate signal types, and may include one or more signal-specific analysis techniques. methods. A validation system may classify a signal to be valid if the signal is not flagged as invalid by any validation stage.

A validation system may include one or more stage definitions, which may include one or more initial validation stages to detect readily apparent or common forms of corruption, and one or more subsequent stages to detect less apparent or less common forms of corruption. Such an approach may permit relatively easy computational detection of relatively obvious corruption, which may permit relatively quick invalidation of simple cases, such as flat signals. The validation system may provide signals deemed valid and signals deemed invalid to downstream algorithms, and the downstream algorithms may use stage definition information to selectively determine whether to use a signal deemed to be invalid by a stage of the validation system.

Figure 27:
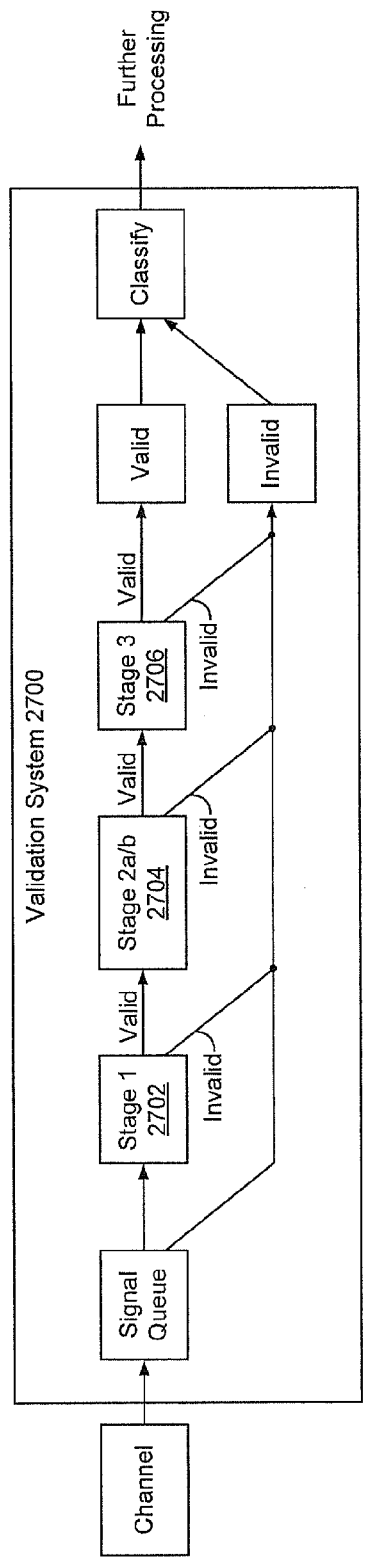
FIG. 27 is a block diagram of a validation system, including multiple validation stages.

FIG. 27 is a block diagram of a validation system 2700, including multiple validation stages 2702, 2704, and 2706.

Validation system 2700 may include corresponding algorithms to validate analog and digital data, which may include one or more of analog EcoG data, analog LFP data, and digital spike data.

For example, stage 2702 may be configured or implemented in accordance with the table immediately below.

| | Analog (Digitized) Validation | Digital (Binary) Validation |
| --- | --- | --- |
| Stage 1 2702 | No Data—Flat Signal | Spike Rate Analysis<br>a. Unnatural Spike Rates<br>i. Injured neurons may fire abnormally high (invalid)<br>ii. Multiple units may increase the spike rate on a single electrode (valid)<br>b. Abnormal Spike Rates (statistically outlier, not necessarily signal corruption) |
| Stage 2 2704 | Noise Level Analysis<br>a. No Data—Pure Noise<br>b. Noise Level above Threshold | Abnormal Spike Properties |
| Stage 3 2704 | Temporal Anomalies—Abnormal Mean/Variance | |

In addition to identifying corrupt channels, a validation system may be configured or implemented to identify when a channel returns to a valid state.

(b) Gating

Gating algorithms attempt to decode movement state of various types of motion, such as premovement and perimovement, or motionlessness. Before attempting to extract movement related activity from neural activity, a determination may be made as to a current state of movement. For example, a user may transition from a state of motionlessness, to a state of planning to make a movement, to a state of actually making a movement. Classifiers that extract discrete class information are referred to herein as state classifiers. A state classifier that extracts movement class information is referred to herein as a gating classifier. Let NG represent the total number of possible movement classes. From a stream of biological and CPC data, the task of a gating classifier is to determine the overall movement regime that the user is in. The estimated movement regime may then be provided to downstream decode algorithms.

In addition to potential increase in computational efficiency provided by a gating classifier in a hierarchical scheme, lack of a gating classifier may potentially permit a decoder to decode spurious movements. Output of gating classifiers may be divergent. One gating classifier may be used to gate multiple decoders of the same group of control on the same processor.

Gating classifiers determine a present state of a user, which may be used to determine how neural information is interpreted. For example, before determining how a user wants to move his or her arm, a determination may first be made as to whether the user wants to a movement. This may help to prevent erroneous movement commands when the user does not desire to make a movement.

Computational load placed on embedded processors may be reduced if components of movement decode algorithms are enabled when a user wants to make a movement.

Presence of a socket may be determined by a signal on one of multiple general purpose inputs on a CPC headstage. This may determine whether CPC algorithms are selected.

(c) Movement Decoders

Movement decoders may include functions to convert biological and CPC input signals to a decision representing a movement or type of movement.

Individual movement decoders produce decisions that represent a desired or intended movement for one or more modular prosthetic limb (MPL) degrees of control (DOC). Where the MPL includes a prosthetic arm, there may be five groups of control (GOC), including an endpoint group, an upper arm group, a wrist group, a hand/finger group, and a generic group. Generic algorithms may be configured to decode positions or velocities for movements of reduced order control and to decode ROC IDs.

End effector decoders may be implemented to decode position or velocity of the end effector at fixed time intervals and determine reverse kinematics at all arm joints. End effector decoders may decode force, position and/or velocity commands for all or substantially all individual joints that determine the position of the end effector. End effector decoders may decode with respect to continuous (position) and/or discrete (position on a discrete grid).

Upper arm decoders may be implemented to decode joint angles of the shoulder and elbow, and may be implemented with respect to continuous (joint angles) and/or discrete (direction of joint movement).

Wrist decoders may be implemented to decode abduction/adduction, pronation/supination and/or flexion/extension. Wrist decoders may be implemented to decode individually or to model as a ball joint and decode two spherical coordinates. Wrist decoders may be implemented to decode velocity and position. Wrist decoders may be implemented with respect to continuous (joint angles) and/or discrete (direction of joint movement).

Finger decoders may be implemented to decode velocity, force, and/or position of individual finger joints, which may be based on metacarpophalangeal (MCP). Finger decoders may be implemented with respect to continuous (joint angles) and/or discrete (direction of joint movement).

Generic decoders may be implemented to decode ROC ID, positions, and/or velocities for movements of reduced order control. Examples of reduced order control include grasps and canonical trajectories.

Multiple decode algorithms may provide the same or similar type of decision, which may not necessarily agree or coincide with one another, referred to herein as conflicting decisions. Conflicting decisions may be reconciled with decision fusion algorithms.

(d) Decision Fusion

Decision fusion algorithms are functions that determine a single intent from multiple decisions of the same type, such as the same group of control and decision space. In a case of one decision of a given type, the decision fusion algorithms may act as a pass-through. In a case of multiple decisions of a given type, decision fusion algorithms may determine an estimate of an intent, or final decision, and an associated confidence based on metrics from the individual decisions from the decode algorithms. From the intent, a corresponding command may be sent to the limb controller. The command may be modulated by the confidence value to prevent quick or sudden movements when confidence is low.

For a given GOC, multiple algorithms may compute decisions for the same MPL DOC. For example, a first algorithm may compute an end effector position and confidence based on EMG data. A second algorithm may compute an end effector position and confidence based on spike data. Alternatively, one of the first and second algorithms may compute joint angles, which may be mapped to an end effector position. Such redundant information may be transformed into a final decision.

A decoder may perform data fusion rather that decision fusion. Where different signal modalities are processed on different processors, data fusion may not be suitable.

Decision fusion algorithms may fuse decisions and confidence values from motor decoding algorithms into a final state estimate. The fused state estimate may be used to initiate an intent, such as sending a command to a limb controller. Computationally, fusion algorithms may be relatively inexpensive.

Some state variables may have discrete values, and some may have continuous values.

Discrete decisions may include finger extension/flexion, grasp type (e.g., cylindrical, lateral, tip, hook, palmer, and spherical), endpoint goal, and joint direction (e.g., flexion/extension, pronation/supination, abduction/adduction).

Continuous decisions may include position, velocity, and joint angles. A first set of decision fusion algorithms may operate on discrete decisions. A second set of decision fusion algorithms may operate on continuous decisions.

When a limb is in an obstacle avoidance mode, hybrid fusion may be considered. Avoiding obstacles may involve constraining movement of discrete joint classes, such as flexion or extension of the elbow, and continuous endpoint positions simultaneously.

Where decision fusion is executed on the NFU and individual decoders may be executed on either of the MCUs and/or on the NFU, depending upon the input modality. Confidence values generated by the individual decoders may be transmitted over a bus between the MCU and the NFU. Confidence values generated by individual decoders, and gating classifiers, may include probabilistic measures, or may be transformed and interpreted as probabilistic measures, and may be input to decision fusion algorithms as illustrated in FIG. 26. Parameters of the decision fusion algorithms may be determined on a per case basis.

To conserve bandwidth, the amount of confidence data may be kept to a relative minimum. For discrete decision fusion problems, decision vectors produced by each decoder may have a maximum length of, for example, 144 indices. For continuous decision fusion problems, decision matrices produced by each decoder may have a maximum length of, for example, 12 for each dimension. Values may be stored as single precision floating point numbers.

Discrete decision fusion algorithms may utilize one or more of majority voting, a linear opinion pool, the sum rule, the product rule, and the median rule.

Continuous decision fusion algorithms may utilize one or more of products of Gaussians, a single Gaussian approximation to a sum of Gaussians, and the pseudomeasurement method.

Optimal decision fusion algorithms may depend upon performance of individual decoders to be fused. In order to determine which fusion algorithms to use in a particular situation, statistics may be collected and measures may be computed from collected data. For continuous decision fusion, execution time, RMS error, and cross-covariance matrices may be computed offline in order to determine the tradeoff between accuracy and computational expense. For discrete decision fusion algorithms, execution time and confusion matrices may be formed and analyzed offline.

(e) Motion Estimation

Outputs of fusion algorithms illustrated in FIG. 26 represent desired commands to a limb controller (LC) in the form of intent. The commands may include desired motion/torque values for individual degrees of motion (DOMs).

A NI may include a full state estimation block to construct higher derivative state information, which may be sent across a system bus at a lower rate that otherwise attainable, without substantially degrading performance. This may improve bandwidth utilization of the system bus.

The full state estimation block may be implemented to recognize when higher derivative state information has already been computed in one or more preceding neural algorithms, and to utilize such information when available.

For example, where an intent provided by a neural algorithm includes a desired DOM joint angle velocity, the full state estimation block may perform one differentiation and one integration at greater than a system bus rate in order to be able to send a complete desired state vector composed of angular position, velocity and acceleration at the system bus rate. This may permit a smoother command signal to be reconstructed and used downstream by a motor controller, referred to herein as a large motor controller (LMC), and LC level.

Where the desired DOM angular position and velocity were previously estimated as part of a neural algorithm and this information is available, the full state estimation block may use the information directly instead of performing the differentiation and integration operations itself.

The full state estimation block may be flexible such that, when the state information is not available, or when the calculation of additional state information is relatively noisy, single command data may be passed on through to the LC as is. The full state estimation block may be implemented with flexibility to dynamically implement relatively more sophisticated state estimation algorithms under some circumstances.

(f) System Interfaces

A MDE may receive biological and CPC inputs from an inputs bus. Selected input signals may be preprocessed and routed to a preprocessing subsystem. Unused signals may be filtered out by a selector. Preprocessing may include signal validation, and may include digital filtering. Signal validation results may be used to remove signals with relatively low signal-to-noise and/or interference ratios. Preprocessing may be omitted or implemented as an all pass filter.

Gating classifiers may apply signal validation results to selected filtered input signals. Gating classifiers may output vectors with measures of confidence indicating or suggesting, for example, no movement, premovement, or perimovement activity. Selected filtered inputs and signal validation results may also used by movement decoders. Discrete movement decoders and continuous movement decoders may include similar or identical input interfaces.

Motion or movement decoders may be implemented to decode continuous state variables and/or discrete classes.

For continuous state variables, a decoder may output a decision vector with a maximum length of, for example, 144 indices, and a decision matrix where each dimension may have a maximum length of, for example, 12.

For discrete classes, a decoder may output a decision vector with a maximum length of, for example, 144 indices.

Movement decoder outputs and confidence metrics from gating classifiers may be provided as inputs to decision fusion. Cortical and peripheral inputs to decision fusion may be routed on a bus between a MCU and a NFU.

Each decision fusion process may output an intent, which may include a state vector for the continuous case or an enumerated discrete class label for a discrete class. Intents may be routed to a motion estimator or motion estimation function.

A motor decode engine may be implemented or configured to:
  extract a set of features from one or more signal inputs, referred to herein as feature extraction algorithms;
  generate a metric of confidence for each intent;
  generate metrics of confidence for decisions;
  generate discrete class decisions; and/or
  generate intents from one or multiple continuous state vector ID.

Additional example motor control features are listed below with reference to a prosthetic arm. One or more features listed below may be implemented with respect to other types of prosthetic devices.

With respect to a prosthetic arm, a motor decode engine may be implemented or configured to perform one or more of:
  decode position for each degree of control in a hand/finger group of control;
  decode velocity for each degree of control in the hand/finger group of control;
  decode positions for reduced order control for the hand/finger group of control when the limb is in grasp mode;
  decode velocity for reduced order control for the hand/finger group of control when the limb is in grasp mode;
  decode position for each degree of control in a wrist group of control;
  decode velocity for each degree of control in the wrist group of control;
  decode endpoint position;
  decode endpoint velocity;
  decode endpoint trajectory;
  scale decoded endpoint positions to a predefined range;
  scale decoded velocities to a predefined range;
  decode angular position for each degree of control in an upper arm group of control;
  decode angular velocity for each degree of control in the upper arm group of control;
  decode positions for reduced order control when a limb is in a reduced order control mode;
  decode velocities for reduced order control when the limb is in a reduced order control mode;
  decode control ROC IDs;
  scale decoded angular positions to a predefined range;
  scale decoded angular velocities to a predefined range; and provide a function that relates confidence of a decision to joint speed.

A motor decode engine may be implemented to generate intents periodically such as, for example, every 20 ms.

A motor decode engine may be implemented to determine signal validity for all selected input signals or a subset thereof. Unused input signals may be filtered out by a selector A motor decode engine may be configured to determine movement intent for each group of control or reduced order control, such as with gating algorithms.

A motor decode engine may be configured to support one or more of:

spike data input channels;

local field potential (LFP) data input channels;

electrocorticogram (ECoG) data input channels;

electromyogram (EMG) data input channels; and conventional prosthetic control (CPC) data input channels.

A CPC may include force sensitive resistors (FSR) and switches.

A motor decode engine may include algorithms with configurable parameters. For example, a motor decode engine may include gating algorithms to adaptively update gating algorithm parameters, and motor decode algorithms to adaptively update motor decode algorithm parameters.

A motor decode engine may be configurable to selectively bypass a movement decoder based on the confidence of a corresponding gating classifier. Gating classifiers may be configured or implemented with respect to corresponding groups of control.

(g) Input Devices

One or more factors may influence signals collected by input devices, including placement of a device.

Signals that contribute to or are correlated with motor control may be present only in certain muscles, nerves, and/or areas of the brain. Physical characteristics of the sensors should be compatible with geometry of an area of a collection medium. For example, finger movement information is encoded in an area of the brain near the central sulcus. Implantation of electrodes in the sulcus, however, often have a relatively low success rate. Impedance and spatial locations of elements in electrode arrays may also affect signal characteristics and correlation functions.

The surface of the brain is a collection of small hills (gyri) and fissures (sulci). Due to the spatial location of the areas planned for implantation, microelectrode arrays may be used to record both on top of sulci and within gyri. When recording on top of a gyrus, microelectrode arrays with shorter shank lengths may be positioned so that the base of the arrays is located on top of the gyms and shanks penetrate down into the cortex. UEAs are used.

To record from within a sulcus, arrays with shorter shank lengths may be placed within the sulcus. This may, however, cause irritation that may results in eventual extrusion of the arrays. Alternatively, arrays with longer shanks may be used, wherein the base may be positioned outside of the sulcus with the shanks extending or penetrating into areas of interest of the sulcus. FMAs may be used.

4. Example 3

LFP, ECoG, and Spike Decoding (a) Example Decoders

Methods and systems to decode flexion or extension of individual fingers and the wrist from spike, local field potential (LFP) and electrocorticographic (ECoG) activity are disclosed below.

Such methods and systems are referred to collectively herein as FM MLE spikeLFPECoG Cls decoding, where FM refers to finger movements, MLE refers to maximum likelihood estimation, spikeLPFECoG refers to spike, local field potential (LFP), and electrocorticographic (ECoG), and CL refers to class.

A FM MLE spikeLFPECoG Cls decoding algorithm may include three component algorithms, one for each of a spike decoder, an LFP decoder and an ECoG decoder.

Each of the three algorithms may include Bayesian classifiers, which may run independent of and in parallel with one another.

Each component algorithm may receive as input:

physiological data (spike, LFP or ECoG signals);

an external cue to trigger or initiate a decode (and to implicitly indicate that a movement should begin); and an external cue to indicate cessation or end of a movement.

Each component algorithm may output, in parallel:

a raw output; and an intent output.

Raw output may include, for each algorithm, unnormalized log posterior probability (ULPP) for all possible classes of movement. Down-stream algorithms in the signal analysis architecture may receive the ULPP values from each individual algorithm, make a final fused decision, and output an intent command that reflects the fused decision.

In generating an intent output, an algorithm may determine single most likely type of movement a user is doing, and may output a corresponding command that conforms to a Modular Prosthetic Limb (MPL) intent bus. This may permit each component algorithm to run alone and independently from the others, such as where a decode from only one modality is needed.

Figures 28, 29, 30:
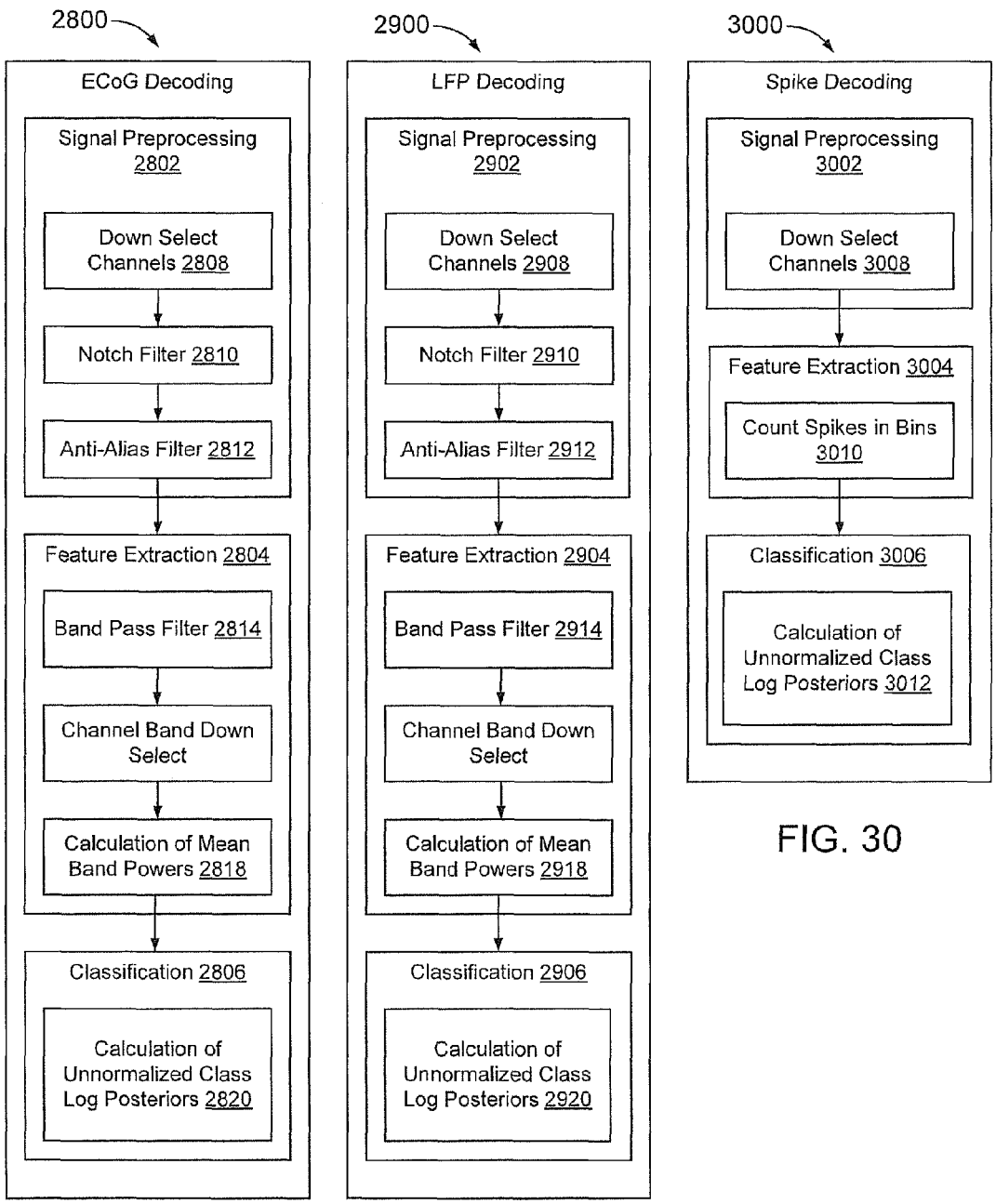
FIG. 28 is a flowchart of a method of ECoG decoding.
FIG. 29 is a flowchart of a method of LFP decoding.
FIG. 30 is a flowchart of a method of spike decoding.

FIG. 28 is a flowchart of a method 2800 of ECoG decoding.

FIG. 29 is a flowchart of a method 2900 of LFP decoding.

FIG. 30 is a flowchart of a method 3000 of spike decoding.

ECoG and LFP decoding are described below with respect to FIGS. 28 and 29.

Algorithmic flow of LFP and ECoG decoding may be substantially similar or identical to one another, while parameter values may differ from one another.

In FIGS. 28 and 29, ECoG decoding and LFP decoding each include signal preprocessing at 2802 and 2902, respectively, feature extraction at 2804 and 2904, respectively, and classification at 2806 and 2906, respectively.

EcoG and LFP preprocessing may each include initial down select of incoming channels. This may permit removal of erroneous channels before they go through any more processing, which may reduce subsequent computational burden. EcoG and LFP channel down select is illustrated at 2808 and 2908 in FIGS. 28 and 29, respectively.

Channels of data that pass through the down select may be notch filtered to remove power line noise that may be present in the signal. Notch filtering may be performed by default, and may be configurable to disabled at run-time. EcoG and LFP notch filtering is illustrated at 2810 and 2910 in FIGS. 28 and 29, respectively.

A raw sampling rate of the LFP and ECoG channels may be greater than that necessary for later processing. To reduce down-stream computational load, channels of data may thus be down-sampled by an integer value. The data may be passed through a low-pass or anti-aliasing filter prior to down-sampling to prevent aliasing in the down-sampled signal. The anti-aliasing filter may be configurable to be disabled at run-time. EcoG and LFP anti-aliasing filtering is illustrated at 2812 and 2912 in FIGS. 28 and 29, respectively.

EcoG and LFP feature extraction may each include band-pass filtering. Up to, for example, five different bands may be extracted from each channel. The same filters may be applied to all channels and then a channel/band down select may be performed to select only the bands from each channel with greater information content relevant to the decode. EcoG and LFP band pass filtering is illustrated at 2814 and 2914 in FIGS. 28 and 29, respectively.

The mean power of all relevant bands for each channel may be measured over a window of a pre-determined size and placed into a vector for use in the calculation of the unnormalized log posterior probability (ULPP) for each class of movement. While data may be constantly buffered to fill windows, mean power calculation may be performed only when an external cue is received to indicate that a moment to decode has arrived. EcoG and LFP mean band power calculation is illustrated at 2818 and 2918 in FIGS. 28 and 29, respectively.

EcoG and LFP classification may be performed with a Bayesian classifier to model the likelihood of observed LFP or ECoG signals for each class with multivariate Gaussian distributions. For reasons of floating point precision, this classification may output an unnormalized log posterior probability (ULPP) for each class, rather than a true probability for each class. A most likely class may be selected as the class with the largest ULPP. Alternatively, the ULPP may be used in a subsequent decision fusion process. Calculation of EcoG and LFP unnormalized class log posteriors is illustrated at 2820 and 2920 in FIGS. 28 and 29, respectively.

Spike decoding is now described with reference to FIG. 30.

In FIG. 30, spike decoding includes signal preprocessing at 3002, feature extraction at 3004, and classification at 3006.

Spike decoding may include receiving channels of pulse trains, where each pulse indicates a spike. Spike detection and sorting may be performed prior to spike decoding.

Preprocessing at 3002 may include channel down-selection at 3008, such as to remove channels of spike data that are erroneous or that carry relatively little information applicable to decoding.

During feature extraction at 3004, impulse trains passing through channel down select may be sent to a spike counter at 3010. When triggered by an external cue, the spike counter may count spikes in a bin of predetermined size and form(s) in a feature vector. The number of features of the feature vector may correspond to the number of counted spike. The spike counter may be configured to implement variable lags for different spike channels.

Upon completion of spike counting for a bin, the spike counter may send an enable signal to trigger or initiate classification at 3006. Classification at 3006 may include a Bayesian decoder. Likelihood terms may be formed based on an assumed conditional independence among spike channels, and each channel may be modeled with a Poisson distribution. As with ECoG and LFP decoding, this may not result in a true probability but rather, a ULPP value for each class, which may be interpreted as described above with respect to ECoG and LFP decoding.

Calculation of spike unnormalized class log posteriors is illustrated at 3012 in FIG. 30.

Figure 31:
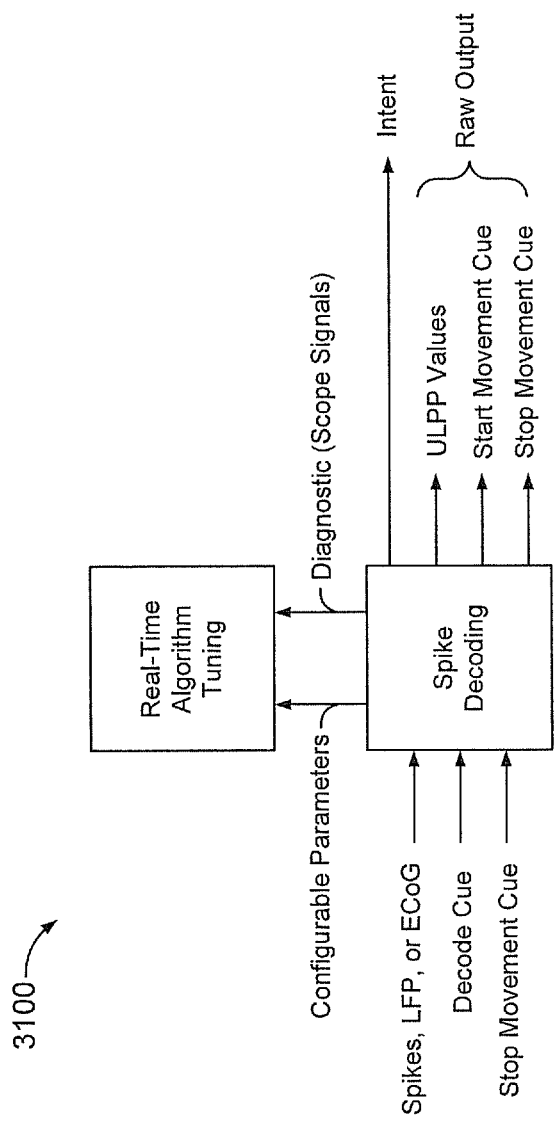
FIG. 31 is a block diagram of a FM MLE spikeLFPECoG Cls decoding system, including example inputs and outputs associated with ECoG, LFP, and spike decoding algorithms.

FIG. 31 is a block diagram of a the FM MLE spikeLFPECoG Cls decoding system 3100, including example inputs and outputs associated with ECoG, LFP, and spike decoding algorithms.

In FIG. 31, components of the FM MLE spikeLFPECoG Cls decoding algorithm each receive:
  physiological data (spike, LFP or ECoG data, as appropriate);
  a decode trigger cue; and
  a movement stop cue.

FM MLE spikeLFPECoG Cls decoder 3100 may receive ECoG, LFP and neural spike data. ECoG and LFP data streams may be provided at, for example, 1000 Hz, and may undergo hardware-based low-pass filtering prior to digital sampling to prevent aliasing. Spike data may be received in the form of spike impulse trains at, for example, 1000 Hz. FM MLE spikeLFPECoG Cls decoder 3100 may be configured without assumption regarding spike sorting, and without assumption spike trains are collected from a particular anatomical/physiological source.

A decode trigger cue may be, for example, a digital pulse of approximately 1 ms duration, and may be used to synchronize a decode to relevant portions of streaming physiological data. A decode trigger cue may will coincide with an occurrence of an event. For example, it might coincide with the closure of a switch.

Each of LFP, ECoG, and spike decoding may interpret trigger cues differently from one another. For spike decoding, a trigger cue may indicate that a decode is to be performed immediately on a window of data ending with the trigger cue. For LFP decoding, the trigger cue may indicate that a decode is to be performed after a window of data is collected. The window of data may start with the decode trigger pulse.

LFP, ECoG, and/or spike decoding may be configurable to delay a trigger cue by a number of samples. This may be useful, for example, where a decode is to be performed pre-determined time after a particular event.

A movement stop cue may be, for example, a digital pulse of approximately 1 ms duration. A movement stop cue may indicate, for example, when a prosthetic hand is to be returned to a neutral position.

Intent outputs may be provided so that component algorithms may be placed within a signal analysis module of a virtual integration environment (VIE) to decode intent without additional code. Intent commands produced by each algorithm may conform to an interface protocol, and may be sent substantially without modification to a controls block of the VIE to move a prosthetic limb.

For each decode occurrence, the intent may be set to drive joint positions to those of the most likely class. The position may be held until a movement stop cue is received, at which time joints may be driven back to a predetermined neutral position.

Raw output may be provided so that component algorithms may be used with fusion algorithms that combine individual outputs of component algorithms into a fused decision. A fusion algorithm may receive one or more of the following, which may be provided by raw outputs of the component algorithms:
- a pulse that indicates when movement is to start;
- ULPP values for each class from each component algorithm; and
- a pulse to indicate when movement is to stop and the joints (e.g., hand), are to return to a neutral position.

Raw output of the component algorithms may be provided on a bus with corresponding fields, such as ULPP, movementStart and movementStop. ULPP values may be provided in a vector, where the $i^{th}$ value is the ULPP value for the $i^{th}$ class. The particular meaning for each class number may be assigned during training.

The movementStart pulse may be synchronized to completion of the decode. For the spike algorithm, the movementStart pulse may coincide with the trigger cue input pulse. For the ECoG and LFP component algorithms, the movementStart pulse may occur after a window of data has been collected and the decode performed. Outputs may be in accordance with double precision.

Component algorithms may utilize configurable or tunable parameters, examples of which are disclosed below. A value of a tunable parameter may be changeable at runtime, and dimensions of a tunable parameter may be unchangeable at runtime. In such an implementation, the values of decode parameters (such as mean vectors and covariance matrices) may be changeable if an algorithm is retrained. If the number of features used in the decode changes, however, the algorithm may need to be recompiled.

Eight example tunable parameters for spike decoding are disclosed below with respect to two classes of parameters, referred to herein as decode and intent mapping tunable parameters.

Decode tunable parameters for spike decoding may include:
MLE_SPK_MEANS;
MLE_SPK_LOG_MEANS;
MLE_SPK_LOG_PRIORS; and
APL_MLE_SPK_CLASS_KEY.

MLE_SPK_MEANS provides the mean firing rate for each unit used in the decode for each class of movement. Specifically, the $i^{th}$, $j^{th}$ entry of this matrix is the mean firing rate of the $i^{th}$ unit for the $j^{th}$ class. Units that are provided to the decoder may be unusable to make a class decision. Thus, the nUnits variable in MLE SPK MEANS and MLE SPK LOG MEANS below, may represent the number of units used in the decode.

MLE_SPK_LOG_MEANS is the log of the MLE_SPK_MEANS variable. The log of the means may be precomputed to reduce computational overhead at runtime.

MLE_SPK_LOG_PRIORS is a vector with a length equal to the number of classes in the decode, where the $i^{th}$ entry gives the log of the prior probability of the occurrence of each class.

MLE_SPK_CLASS_KEY permits remapping of class numbers after decoding. MLE_SPK_CLASS_KEY may be a vector with a length equal to the number of classes in the decode, where the $i^{th}$ entry gives the number that class i is to be referred to in the remainder of the algorithm. Specifically, this variable determines the order that ULPP variables are placed in the ULPP output of the algorithm. For example, if the first entry of the vector is 2, the ULPP value for the class that is referred to as class 1 in the other decoder parameters mentioned in this section are placed as the second entry of the ULPP vector and referred to as class 2 in the intent mapping tunable parameters.

Intent mapping tunable parameters for spike decoding may include:
MLE_SPK_N_JOINTS_PER_CLASS;
MLE_SPK_JOINT_MAP;
MLE_SPK_MAG_MAP; and
MLE_SPK_JOINT_MAP_INC_NULL_CLASS.

MLE_SPK_N_JOINTS_PER_CLASS is a vector with a length equal to the number of classes in the decode. The $i_{th}$ value gives the number of joints in class i, as defined by the MLE_SPK_CLASS_KEY variable. For example, if class 1 involves flexion of the thumb and index MCP joints, the value of nJointsPerClass(1) is 2.

MLE_SPK_JOINT_MAP is a matrix of size nClasses by nJoints, where nClasses is the number of classes in the decode and nJoints is the number of joints of the prosthetic device. nJoints may be, for example, 27. By default, each value may be zero. This matrix maps the joints involved in class C using the key given in the table below. The value of the $i^{th}$, $j^{th}$ entry of the jointMap matrix may represent a value giving the ID of the $j^{th}$ joint in class i. The order of the joints may be immaterial. If a particular class of movement involves the movement of less than nJoints, zeros may be used as place holders at the end of the row for that class.

Example Key for Joint Values for Use in the jointMap Variable

| | |
|---|---|
| 1 | ShoulderFE |
| 2 | ShoulderAbAd |
| 3 | HumeralRot |
| 4 | Elbow |
| 5 | WristRot |
| 6 | WristAbAd |
| 7 | WristFE |
| 8 | IndexAbAd |
| 9 | IndexMCP |
| 10 | IndexPIP |
| 11 | IndexDIP |
| 12 | MiddleAbAd |
| 13 | MiddleMCP |
| 14 | MiddlePIP |
| 15 | MiddleDIP |
| 16 | RingAbAd |
| 17 | RingMCP |
| 18 | RingPIP |
| 19 | RingDIP |
| 20 | LittleAbAd |
| 21 | LittleMCP |
| 22 | LittlePIP |
| 23 | LittleDIP |
| 24 | ThumbAbAd |
| 25 | ThumbCMC |
| 26 | T umbMCP |
| 27 | ThumbIP |

MLE_SPK_MAG_MAP is a matrix of size nClasses by nJoints, and provides magnitude (angle) that a corresponding joint in the jointMap matrix is to be driven to. The position may be provided in degrees.

MLE_SPK_JOINT_MAP_INC_NULL_CLASS is a scalar value, which can be either 1 or 0. If the value is 1, when the enable signal is 0, a command may be sent to drive to the limb back to a neutral state. The neutral state may be treated as an extra class where an appropriate entry for it has been appended to the MLE_SPK_N_JOINTS_PER_CLASS, MLE_SPK_JOINT_MAP and MLE_SPK_MAG_MAP variables.

Example Configurable Algorithm Parameters for
Spike Decoding

| Parameter Name | Type | Size |
|---|---|---|
| MLE_SPK_MEANS | double | [nUnits, nClasses] |
| MLE_SPK_LOG_MEANS | double | [nUnits, nClasses] |
| MLE_SPK_LOG_PRIORS | double | [nClasses, 1] |
| MLE_SPK_CLASS_KEY | double | [nClasses, 1] |
| MLE_SPK_N_JOINTS_PER_CLASS | double | [nClasses + 1, 1] |
| MLE_SPK_JOINT_MAP | double | [nClasses + 1, nJoints] |
| MLE_SPK_MAG_MAP | double | [nClasses + 1, nJoints] |
| MLE_SPK_JOINT_MAP_INC_NULL_CLASS | double | 1 |

Eleven example tunable parameters for LFP and ECoG decoding are disclosed below with respect to three groups of parameters, referred to herein as filter, decode, and intent mapping tunable parameters.

Filter tunable parameters for LFP(ECoG) decoding may include:

MLE_LFP(ECoG)_ENABLE_NOTCH_FTR; and
MLE_LFP(ECoG)_ENABLE_AA_FTR.

These two parameters may enable (value of 1) or disable (value of 0) filtering in preprocessing LFP (ECoG) data.

MLE_LFP(ECoG)_ENABLE_NOTCH_FTR parameter determines whether a notch filter is applied to remove power line noise.

MLE_LFP(ECoG)_ENABLE_AA_FTR parameter determines whether an anti-aliasing filter is applied before down sampling.

Decode tunable parameters for LFP (ECoG) decoding may include:

MLE_LFP(ECoG)_CLASS_MEANS;
MLE_LFP(ECoG)_CLASS_INV_COVS;
MLE_LFP(ECoG)_CLASS_LOG_NORM_CONSTS;
MLE_LFP(ECoG)_CLASS_LOG_PRIORS; and
MLE_LFP(ECoG)_CLASS_KEY.

MLE_LFP(ECoG)_CLASS_MEANS is a matrix of size F by nClasses, where F is the number of features in the decode into a feature vector. The $ii^{th}$, $ji^{th}$ entry of this matrix gives the mean value of feature i for class j.

MLE_LFP(ECoG)_CLASS_INV_COVS is a matrix of size F*nClasses by F matrix. The first F rows may contain the inverse covariance matrix for the first class. The second F rows may contain the inverse covariance matrix for the second class, etcetera. The algorithm may be provided with inverted covariance matrices to save computational expense at run-time.

MLE_LFP(ECoG)_CLASS_LOG_NORM_CONSTS is the log of the normalizing constants of the likelihood terms for each class. This is a vector with a length equal to the number of classes in the decode. The $i^{th}$ value gives the normalizing constant for the $i^{th}$ class.

MLE_LFP(ECoG)_CLASS_LOG_PRIORS parameter may be substantially similar or identical to that of the spike decoder described above.

MLE_LFP(ECoG)_CLASS_KEY parameter may be substantially similar or identical to that of the spike decoder described above.

Intent mapping tunable parameters for LFP and ECoG decoding may be substantially similar or identical to intent mapping tunable parameters for spike decoding, such as described above.

Example Configurable Algorithm Parameters for
LFP Decoding

| Parameter Name | Type | Size |
|---|---|---|
| APL_MLE_LFP_ENABLE_NOTCH_FTR | double | 1 |
| APL_MLE_LFP_ENABLE_AA_FTR | double | 1 |
| APL_MLE_LFP_CLASS_MEANS | double | [nLFPFtrs, nClasses] |
| APL_MLE_LFP_CLASS_INV_COVS | double | [nLFPFtrs*nClasses, nLFPFtrs] |
| APL_MLE_LFP_CLASS_LOG_NORM_CONSTS | double | [nClasses, 1] |
| APL_MLE_LFP_CLASS_LOG_PRIORS | double | [nClasses, 1] |
| APL_MLE_LFP_CLASS_KEY | double | [nClasses, 1] |
| APL_MLE_LFP_N_JOINTS_PER_CLASS | double | [nClasses, 1] |
| APL_MLE_LFP_JOINT_MAP | double | [nClasses, nJoints] |
| APL_MLE_LFP_MAG_MAP | double | [nClasses, nJoints] |
| APL_MLE_LFP_JOINT_MAP_INC_NULL_CLASS | double | 1 |

Not all bands from all channels of data are necessarily used in the decode. Instead, a down select may performed and a subset of bands from a subset of channels may be formed Example Configurable Algorithm Parameters for
ECoG Decoding

| Parameter Name | Type | Size |
|---|---|---|
| APL_MLE_ECoG_ENABLE_NOTCH_FTR | double | 1 |
| APL_MLE_ECoG_ENABLE_AA_FTR | double | 1 |
| APL_MLE_ECoG_CLASS_MEANS | double | [nECoGFtrs, nClasses] |
| APL_MLE_ECoG_CLASS_INV_COVS | double | [nECoGFtrs*nClasses, |

| Parameter Name | Type | Size |
| --- | --- | --- |
| | | nECoGFtrs] |
| APL_MLE_ECoG_CLASS_LOG_NORM_CONSTS | double | [nClasses, 1] |
| APL_MLE_ECoG_CLASS_LOG_PRIORS | double | [nClasses, 1] |
| APL_MLE_ECoG_CLASS_KEY | double | [nClasses, 1] |
| APL_MLE_ECoG_N_JOINTS_PER_CLASS | double | [nClasses, 1] |
| APL_MLE_ECoG_JOINT_MAP | double | [nClasses, nJoints] |
| APL_MLE_ECoG_MAG_MAP | double | [nClasses, nJoints] |
| APL_MLE_ECoG_JOINT_MAP_INC_NULL_CLASS | double | 1 |

One or more decoding algorithms may be implemented with assumptions. Assumptions may include, for example, one or more of:

user's eys are center fixated;
user is in a seated position;
time of movement start is known a priori;
spike data has undergone spike sorting; and
signal tuning curves will not drift substantially over time.

A component algorithm may determine the most likely class of movement from streaming LFP, spike, or ECoG signals, as applicable, when cued by an external signal.

A component algorithm may wait a user-selectable pre-defined time after receiving an external signal before performing a decode. A delay period may be utilized. For example, a primate may be commanded to move a finger, and it may take, for example, 150-200 milliseconds after the onset of the command cue before cortical signals reflect a response to this command. A delay parameter may be used to take such a delay into account.

A component algorithm may make ULPP values available for each class. For example, decoding may utilize three independent algorithms, one for each modality, and downstream fusion algorithms may be utilized to fuse outputs of the three algorithms. In order for the fusion algorithms to fuse the output of each algorithm, more than a single class decision from each component algorithm may be provided. The ULPP values may thus be provided as a measure of the likelihood of each possible class.

Component algorithms may each be implemented to make a decision within a fixed time offset subsequent to receipt of a fresh feature vector. This may reduce jitter and latency, which may improve real-time, closed loop control of a virtual or real prosthetic.

A component algorithm may be implemented to permit mapping of any class to any possible combination of joint positions for which the prosthetic limb is capable. This may permit the component algorithm to be used for classification of movements of multiple types of joints or prosthetic devices.

A component algorithm may be precluded from a priori constraining its output to a limited set of a full set of trained classes. This may help to insure that a class that is relatively rare, is not ruled out as a possibility before a decode is performed. Potential performance benefits and patient safety issues may be considered with respect to implementation of such a constraint.

Component algorithms may each include a decoder sub-module and an intent mapping sub-module.

The decoder sub-modules may each receive as inputs physiological data, decode trigger, and movement stop cues. The decoder sub-module may output ULPP values for each class, movementStart and movementStop signals and diagnostic signals. ULPP values may be held constant between movementStart signals.

The intent mapping sub-modules of each component algorithm may receive vectors of ULPP values output by the decoder sub-module, and an enable signal. When the enable signal is at a first stage, the intent mapping sub-module may select the most likely class and may output a model intent command. When the enable command is at a second state, the intent mapping sub-module may output an intent command to drive the limb back to a neutral position.

To facilitate code reuse, the decoder sub-module of each component algorithm may be implemented so that it is not constrained to be used only for the classification of particular movements.

Similarly, to facilitate expanded use of component algorithms, the intent mapping sub-module of each component algorithm may allow for the mapping of any class to any possible combination of joint positions for which the prosthetic limb is capable.

Each component decoder may be implemented to independently estimate intent from one of spike, LFP, and ECoG signals.

Algorithms may be designed based on one or more data sets. For example, simultaneous recording of LFP and spike activity have been generated by the University of Rochester Medical Center [URMC], from a primate performing switch task. Such data may be used to design and/or verify spike and LFP algorithms. In addition, a ECoG component algorithm may be initially verified with LFP data, and subsequently be verified with ECoG data.

Where algorithms are tested and verified with switch task data, such algorithms may generalize to other paradigms, such as finger flexion and extension movements.

LFP and ECoG decoders may be implemented to extract different frequency bands to form corresponding feature vectors, and thus may be implemented with substantially similar or identical algorithmic flow. For example, a common frequency band decoder may be used for both the LFP and ECoG decoders, which may permit re-use of code.

Spike and frequency band decoders may be designed and verified within a simulator, following which, offline training of algorithm parameters may be performed. Thereafter, the component algorithms may be implemented in a fusion architecture.

(b) Bayesian Classifiers

One or more component algorithms may include Bayesian classifiers. Bayesian classification is based on a likelihood term for each class, a prior probability for each class, and a posterior probability of each class.

Regarding the likelihood term, when decoding, it may be assumed that the likelihood functions for each class are known. To understand the likelihood function, it may be helpful to think of the decoding problem in reverse. Instead of seeking the most likely class given some observed signal, the inquiry is directed to the probability of the observed neural signal given that a certain class of movement has occurred. The likelihood function provides that latter probability. By way of an example, based on an observer LFP signal, the likelihood function determines the probability of the observed LFP signal being produced by each possible class of movement.

Regarding the prior probability term, when decoding, it may be assumed that the prior probability for each class is known, and that the distribution for the prior probability for all classes is uniform. The assumption of a uniform distribution may help to ensure that no class of movement is "weeded out" simply because it rarely happens. This may serve as a safety consideration.

Regarding the posterior probability term, ultimately, the quantity of interest is not the probability of a observed signal given a class of movement but the reverse, that is, the probability of a class of movement given an observed signal. This is referred to as the posterior probability for each class, and Bayes' theorem permits going from one to the other. Once the posterior probability for each class is known, a command may be generated based on the class with the highest posterior probability.

After training, the likelihood and prior probability terms may be assumed to be known. The task of the each component decoder is to use these distributions and, when presented with a novel observation, determine the posterior probability of 1 of C classes occurring.

Bayes' theorem relates these three terms as follows:

$$P(\omega_c | \vec{O}) = \frac{P(\vec{O} | \omega_c) P(\omega_c)}{P(\vec{O})} \quad \text{(Eq. 1)}$$

In Eq. 1, $\omega_c$ is a variable that represents class c. For a hand prosthetic, classes may correspond to flexion or extension of corresponding single digits, or the combined flexion and extension of some group of fingers.

The variable $\vec{O}$ is an observation vector, which may include a vector of spike counts or a vector of the power of certain band passed signals from select LFP or ECoG channels.

$P(\omega_c | \vec{O})$ is the posterior probability term. It may be understood as giving the probability of class c occurring given that a known observation has been made.

The quantity $P(\vec{O} | \omega_c)$ is the likelihood term described above. $P(\omega_c)$ is the prior probability of each class.

$P(\vec{O})$ serves as a normalizing constant and is the probability of the observed vector. $P(\vec{O})$ may be a constant that equally applies to the posterior probability of all classes. As such, it may be omitted.

A formula to calculate ULPP values for class c may be derived as disclosed below.

Since unnormalized posterior probability terms are sought, the denominator in Eq. 1 may be removed to provide:

$$P(\omega c | \vec{O}) \propto P(\vec{O} | \omega_c) P(\omega_c)$$

In Eq. 2 below, the natural log of both sides is computed, which may reduce chances of having a numerical underflow when probability values become relatively small. In Eq. 2, the term $\text{ULPP}_c(\vec{O})$ is the unnormalized posterior probability for class C:

$$\text{ULPP}_c(\vec{O}) = \log(P(\vec{O} | \omega_c)) + \log(P(\omega_c)) \quad \text{(Eq. 2)}$$

Eq. 2 represents a general formula. For ULPP values, specific forms of Eq. 2 may be provided for the likelihood terms, such as disclosed in examples below.

The likelihood term for the spike decoder may be derived with the assumption that each unit will have a characteristic mean firing rate associated with each class. This may permit modeling of the likelihood of observing a firing rate for unit u given the occurrence of class c with a Poisson distribution:

$$P(n_u | \omega_c) = \frac{\lambda_{u,c}^{n_u} e^{\lambda_{u,c}}}{n_u!}$$

Symbols used in the equation above and in equations below are defined further below.

Conditional independence among the firing rates for all units may be assumed, and the likelihood of observing a collection of firing rates, represented as variable $\vec{O}$, described above, may be written as:

$$P(\vec{O} | \omega_c) = \prod_{u=1}^{U} \frac{\lambda_{u,c}^{n_u} e^{\lambda_{u,c}}}{n_u!}$$

Taking the log of the above-equation provides:

$$\log(P(\vec{O} | \omega_c)) = \sum_{u=1}^{U} (n_u \log(\lambda_{u,c}) \; \lambda_{u,c} \; n_u!)$$

The above-quantity may be inserted into Eq. 2 and used with the log of the prior probability for class c, which is assumed to be known, to calculate $\text{ULPP}_c(\vec{O})$.

Parameters in Likelihood Term for Spike Decoding

| Parameter | Definition |
| --- | --- |
| $\omega_c$ | Class c. |
| $\vec{O}$ | Observation vector. |
| $\lambda_{u,c}$ | Mean firing rate of unit u for class c. |
| $n_u$ | Observed firing rate for unit u. |

For LFP and ECoG decoders, it may be assumed that the power of certain frequency bands from certain channels will attain some mean values with some known covariance among themselves for each class of movement. Symbols used in the following equations are defined in the table below.

With these assumptions, likelihood term may be modeled for each class as a multivariate Gaussian distribution:

$$P(\vec{O} | \omega_c) = \frac{1}{S_c} e^{\frac{1}{2}(\vec{O} \; \mu_c)' \Sigma_c^{-1} (\vec{O} \; \mu_c)}$$

The term SC is referred to as a normalizing constant for class c and may be defined as:

$$S_c = \frac{1}{(2\pi)^{\frac{N}{2}}|\Sigma_c|}$$

Taking the natural log of the likelihood term provides:

$$\log(P(\vec{O}|\omega_c)) = \log(S_c) \frac{1}{2}(\vec{O}_c \ \mu_c)'\Sigma_c^{-1}(\vec{O}_c \ \mu_c)$$

As with spike decoding, the above-quantity may be inserted into Eq. 2 and used along with the log of the prior probability for class c, which is assumed to be known, to calculate $ULPP_c(\vec{O})$.

Parameters in Likelihood Term for ECoG and LFP Decoding

| Parameter | Definition |
|---|---|
| $\omega_c$ | Class c. |
| $\vec{O}$ | Observation vector. |
| $\mu_c$ | Vector of mean feature values for class c. |
| $\Sigma_c$ | Covariance matrix for class c. |

When training a spike decoder, the mean firing rate for each unit and class is needed ($\lambda_{u,c}$). In practice, the mean firing rate vector for class c ($\mu_c$) is found. The formula for $\mu_c$ may be written as:

$$\mu_c = \frac{1}{N_c}\sum_{i=1}^{N_c}\vec{O}_c$$

In the above-equation, $N_c$ is the number of training observation vectors for class C and $\vec{o}_c$ is the observed vector for each class.

When training LFP or ECoG component decoders, in addition to the mean, the covariance for each class is needed. The training formula for $\Sigma_c$ may be written as:

$$\Sigma_c = \frac{1}{N_c}\sum_{i=1}^{N_c}(\vec{O}_c \ \mu_c)(\vec{O}_c \ \mu_c)'$$

As disclosed above, one or more decoders may not use all units or bands from LFP channels to decode.

A one-way analysis of variance (ANOVA) test may be utilized to down select units and LFP channels/frequency band combinations. Such a test provides the probability that the difference in mean class values for feature values is due to chance. Units and LFP features having class means that have a significantly low probability, given by their p-value, of being different due to chance alone may be included in the decode. Features may also be ranked according to p-value, and a subset may be selected from the list.

A data set used to train a component algorithm may include:
 a stream of physiological data;
 a record of the occurrence of the event to be used in an online decode for which to synchronize the decode; and
 trials of data for each class of movement.

Example quantities are provided below. Methods and systems disclosed herein are not, however, limited to the examples herein.

For a spike decoder, approximately 20 training trials may be used for each class of movement, irrespective of the number of units in the decode. For an LFP decoder, approximately 200 trials per movement of LFP data have been used to train the decoder when approximately 20 channels of LFP data are actually used in decoding. Channels included in the decoding were down-selected from all available using a one-way ANOVA test.

(i) Analysis of Example Design Decisions

In an example implementation, design decisions were based on experience with a dataset of simultaneous recordings of LFP and spike data, obtained from another source. It is noted, however, that Bayesian approaches have been successfully utilized by others, as described immediately below.

(1) Previous Use of Bayesian Classifiers

Previous use of Bayesian classifiers are described below.

In a set of experiments conducted at the University of Rochester Medical Center (URMC), primates were trained to place a hand in manipulandum and individually flex and extend all five fingers and the wrist. Additionally, one primate was trained to flex and extend the thumb/index, index/middle and ring/little combinations of fingers.

Recordings were made with individual electrodes over a period of months from the primate motor (MI) and dorsal premotor (PMd) brain areas of each primate. Recordings from individual units were later combined to simulate recording from an array.

Spikes were counted in 100 millisecond bins directly before switch closure and using 30% of trials for training and 70% for testing the results in the table immediately below were obtained.

Summary of Results of Using a Bayesian Classifier to Decode URMC Manipulandum Data

| Monkey | Type of Movements Decoded | Number of Units used in the Decode | Percent Accuracy |
|---|---|---|---|
| K | Individual fingers and wrist | 102 | 100% |
| C | Individual fingers and wrist | 99 | 100% |
| G | Individual fingers and wrist | 111 | 99.8% |
| K | Individual fingers and wrist and combined fingers | 110 | 99.1% |

Additional information regarding the URMC datasets and decoding technique are provided in: Aggarwal, V., et al., *Asynchronous Decoding of Dexterous Finger Movements Using M1 Neurons*, Neural Systems and Rehabilitation Engineering, IEEE Transactions, vol. 16, no. 1, pp. 3-14, Feb. 2008, incorporated herein by reference in its entirety.

In a set of experiments conducted at the California Institute of Technology, a primate was trained to reach to 4 or 8 goals. Recordings of cortical spikes from the parietal reach region were made using microwire arrays. Spikes were counted in 1 second bins during a period after the primate had been instructed on which goal to reach for but before the primate was permitted to reach for the goal. 30% of the data was used for training, and 70% was used for testing. Decoding results for the "plan" activity are presented in the table immediately below.

Summary of Results of Using a Bayesian Classifier
to Decode CalTech Plan Activity

| Monkey | Number of Goals Included in the Decode | Number of Units used in the Decode | Percent Accuracy |
|---|---|---|---|
| S | 4 | 54 | ~89% |
| S | 8 | 82 | ~57% |
| S | 8 | 82 | ~70% |

Additional information the CalTech experiment and decode technique are provided in, S. Musallam, et al., *Cognitive Control Signals for Neural Prosthetics*, Science 305, 258 (2004), incorporated herein by reference in its entirety.

In a demonstration carried out at Stanford University, a primate was trained to perform a center out task to 4 goals. Recordings were made with a Stanford Hermes-C-Nano/INI-5 system. The system enabled the recording of spikes, detected via threshold crossings, on 20 electrodes and the wireless transmission of the data. The data was received and provided in real-time to the VIE, with a cue used to synchronize a Bayesian classifier. Using this system and counting spikes in 150 ms bins falling 150-200 ms after a go cue (individual lags were fit for each unit), an accuracy of ~95% was achieved with 200 trials using 18 threshold crossings.

(2) LFP and ECoG Filter Design

LFP and ECoG decoders may utilize digital filters, such as to remove power line noise, prevent aliasing when down-sampling, and/or to band pass filter channels of data as part of feature extraction.

The digital filters may be configured to have relatively sharp transitions between stop and pass bands, to have relatively low ripple in the pass band, and/or to have a relatively low number of coefficients.

Sharp transitions permit relatively tight control over which bands are passed through at each filtering step. For notch and anti-aliasing filters, sharp transitions permit tighter filtering bounds to be set, leaving more bandwidth for analysis. For bandpass filters used in feature extraction, sharp transitions reduce the region of frequency overlap between band passed signals.

Low ripple helps to ensure that all frequencies in a band are weighted equally.

Low numbers of coefficients may reduce latency that may otherwise be used to the decode using longer filters.

Digital filters in LFP and ECoG decoders may include elliptical filters, since they permit for relatively very sharp transitions between stop and pass bands while maintaining relatively low ripple in the pass band.

Elliptical filters were designed for multiple application areas. In the design of the filters, −10 decibels was selected as the cutoff attenuation. Analysis was carried out by examining magnitude plots of the elliptical filters, as described below.

Each filter may operator-adjustable for various environments. Filters analyzed below may be generally representative.

Figure 32:
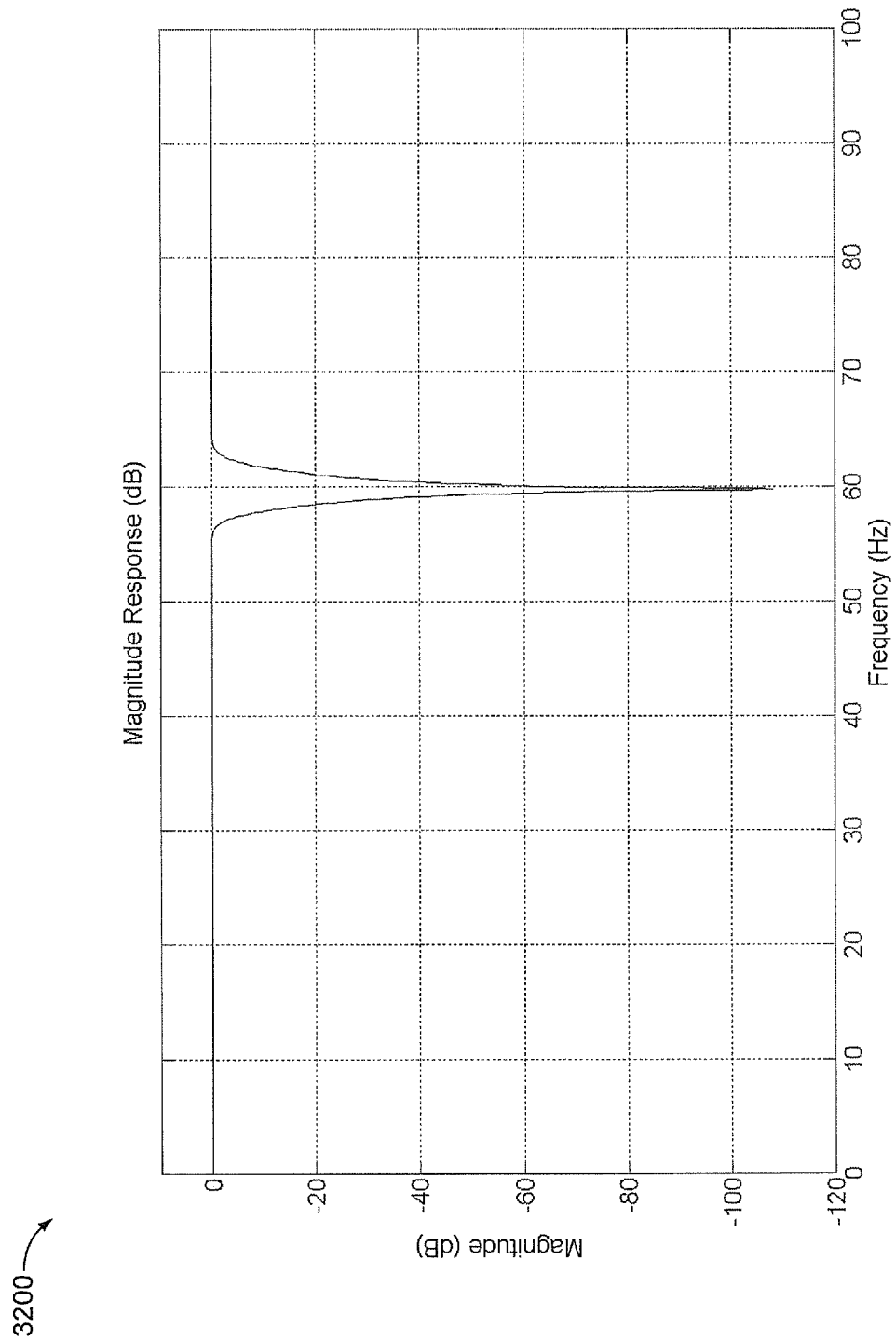
FIG. 32 is a magnitude plot for a 3rd order elliptical notch filter with cutoff frequencies at 55 and 65 Hz designed to operate at a signal sampled at 1000 Hz.

FIG. 32 is a magnitude plot 3200 for a 3rd order elliptical notch filter with cutoff frequencies at 55 and 65 Hz designed to operate at a signal sampled at 1000 Hz.

Figure 33:
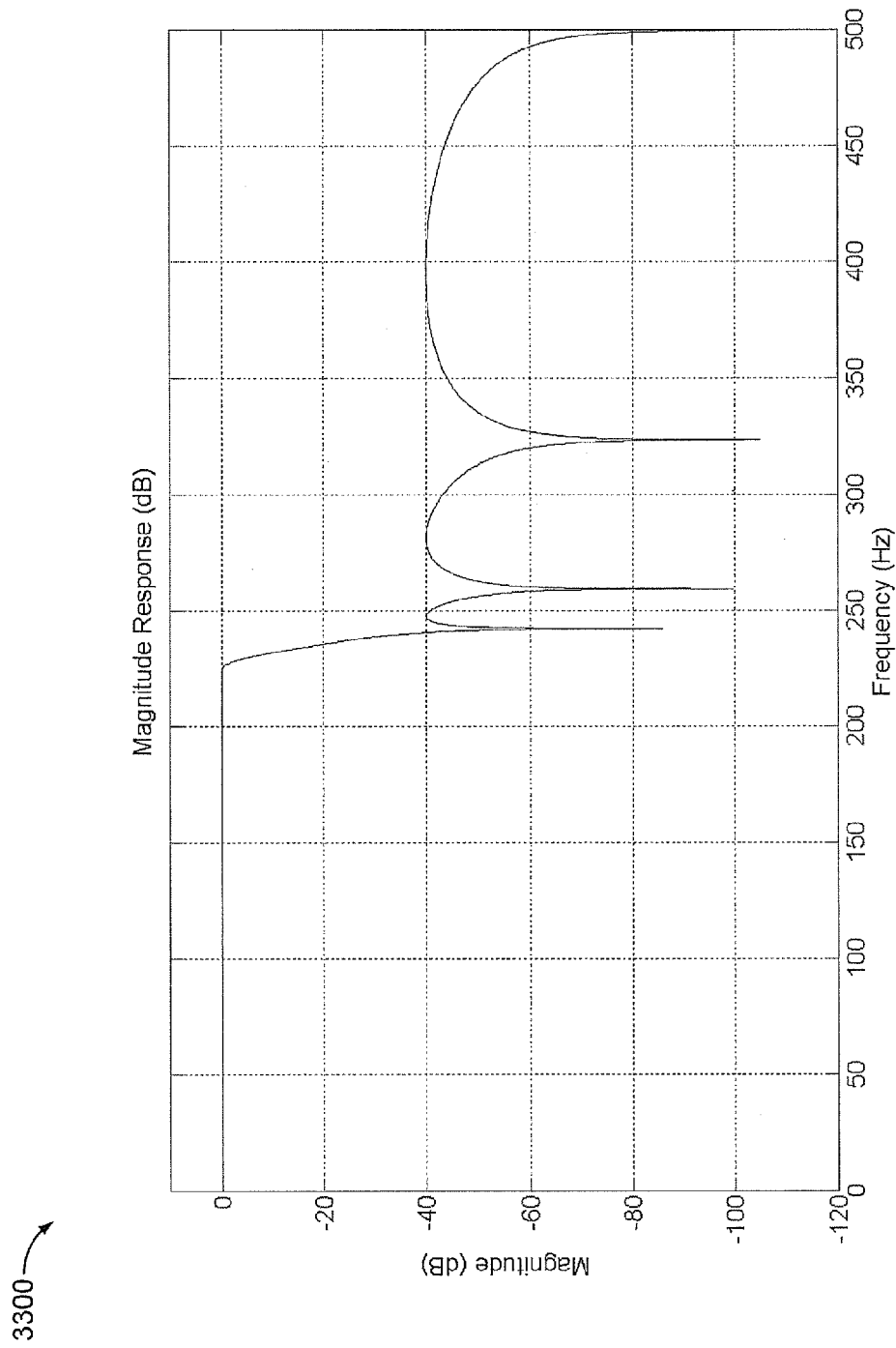
FIG. 33 is a magnitude plot for a 7th order elliptical anti-aliasing filter with a cutoff frequency of 225 Hz designed to operate on a signal originally sampled at 1000 Hz before down sampling to 500 Hz.

FIG. 33 is a magnitude plot 3300 for a 7th order elliptical anti-aliasing filter with a cutoff frequency of 225 Hz designed to operate on a signal originally sampled at 1000 Hz before down sampling to 500 Hz.

Figure 34:
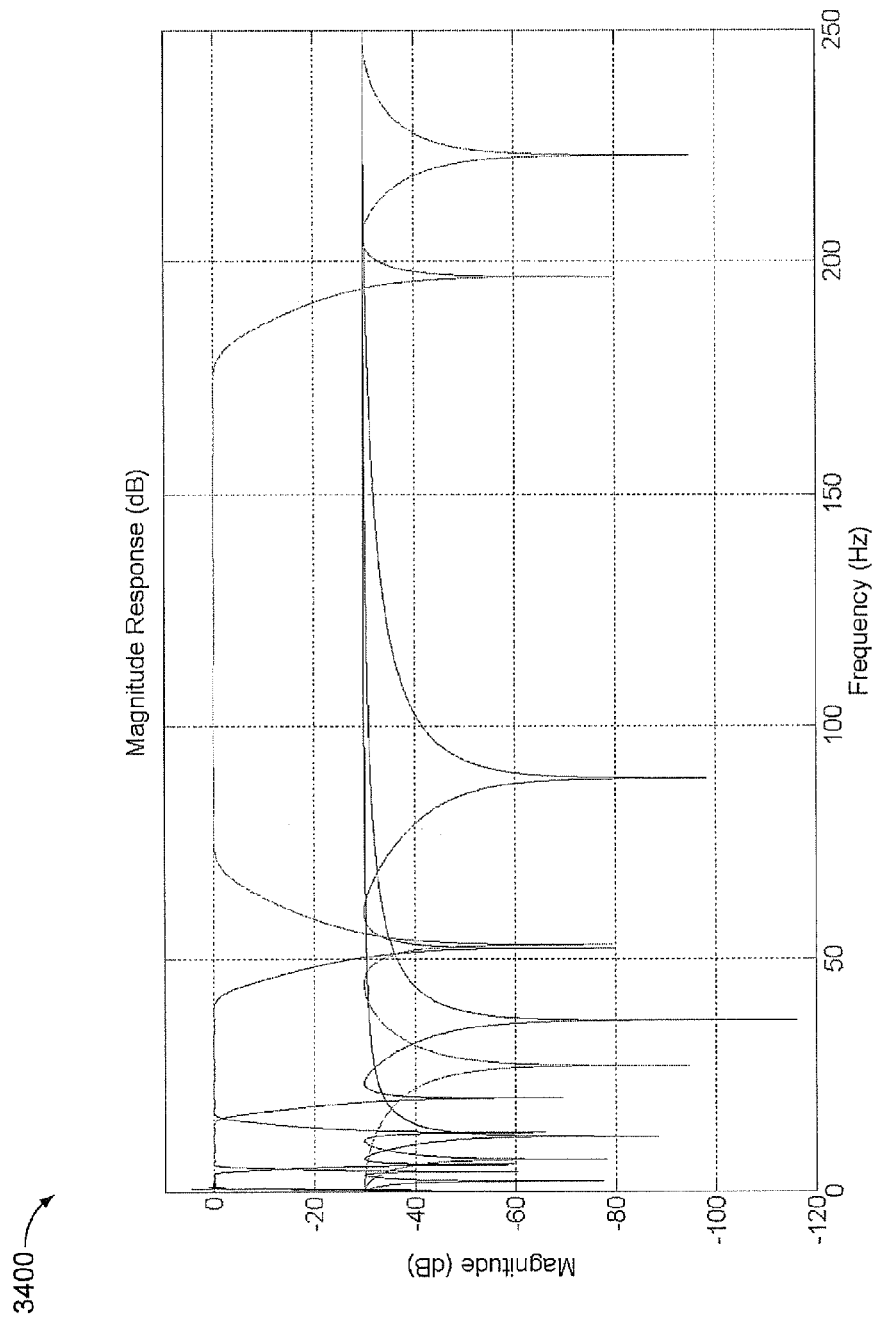
FIG. 34 is magnitude plot of four band pass filters usable to separate channels into different frequency bands before average power of each band is calculated, such as in feature extraction.

FIG. 34 is magnitude plot 3400 of four band pass filters usable to separate each channel into different frequency bands before average power of each band is calculated, such as in feature extraction. In FIG. 34, pass bands are between 1-4 Hz, 6-15 Hz, 17-40 Hz, and 75-175 Hz. All filters are fourth order filters.

(3) Component Decoder

A spike component decoder was analyzed with URMC switch task data Multiple factors were examined, and five analyses were performed.

The first analysis compared decoders using Poisson and Gaussian likelihood models.

The second analysis compared the performance of the spike decoder when spike sorting was used and when spikes were simply grouped by electrode.

The third analysis compared the performance of the decode when a one way ANOVA test was used to reduce the number of units included in the decode.

The fourth analysis again looked at the decode performance with sorted and unsorted spikes but used Gaussian (instead of Poisson, as was used in the first model) likelihood models.

The fifth analysis looked at the effect of bin size on decode performance.

In all the five analyses, times have been rounded to the nearest millisecond to reflect constraints faced on the xPC.

The results of these analyses are shown in the following five figures.

Ten fold cross validation was performed for each test point. To simulate the dropping of units, an appropriate number of units were selected at random to feed into the decoder. For each fold, between 50 to 150 repetitions were performed, roughly proportional to the reciprocal of the number of units presented to the decoder, to get an average accuracy value. This was then repeated for each fold to produce the values for the test points plotted in the figures below.

For those tests that used an ANOVA test to down select units, the number of units actually used in the decode was lower than the number presented to it. This simulates recording from a random population of units, some of which may be well tuned for the task at hand, while others may not be.

When using an ANOVA test with a low number of units, there were occasions when all units presented to the decoder were weeded out in training. In this case, results from that repetition were not counted.

Data from a switch task paradigm was used in this section. The decode task was to decode which of three switches a monkey was manipulating.

Figure 35:
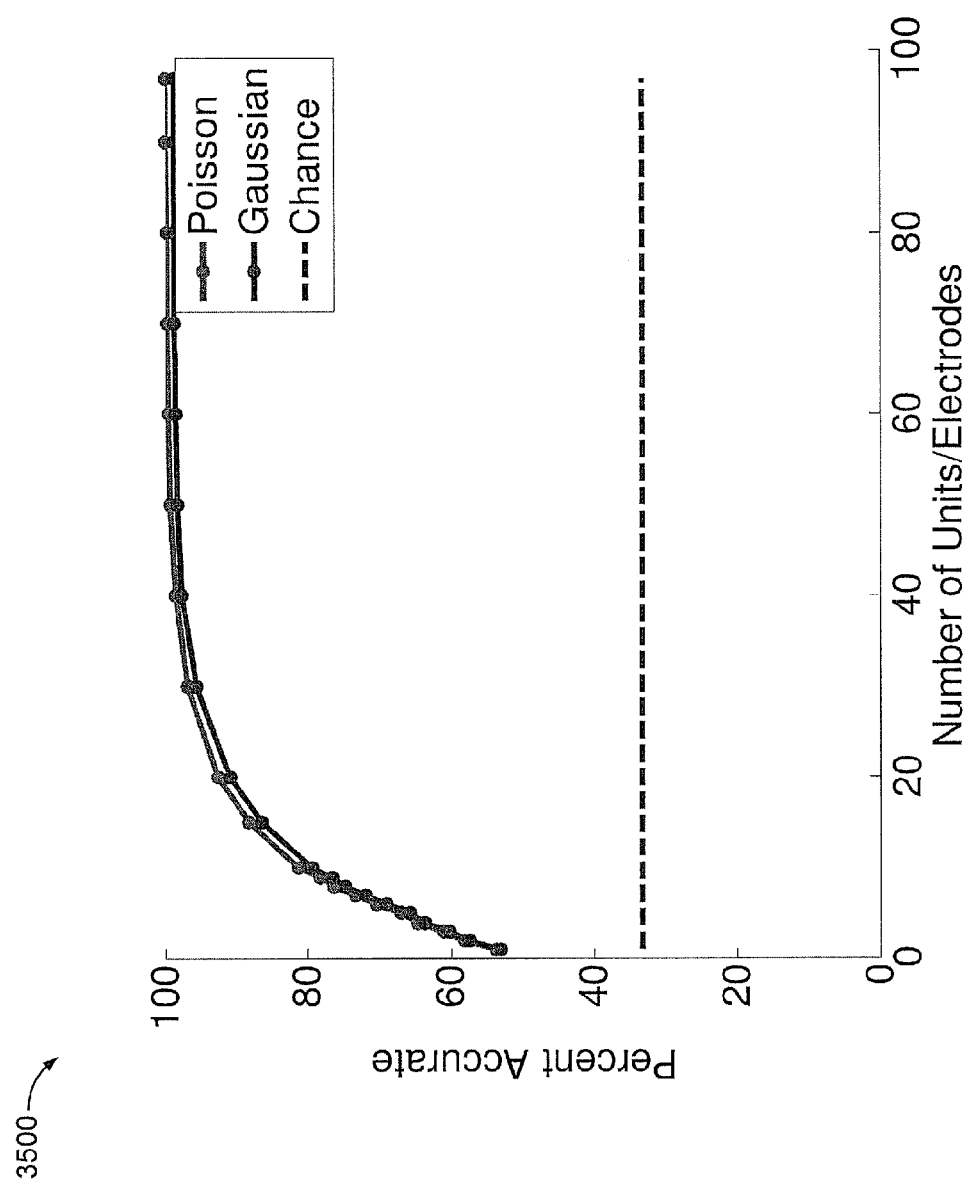
FIG. 35 is a graph of results of an analysis comparing the use of Poisson and multivariate Gaussian likelihood models.

FIG. 35 is a graph 3500 of results of the analysis comparing the use of Poisson and multivariate Gaussian likelihood models. In both cases, a one-way ANOVA test was performed to reduce the dimensionality of data. Spikes were counted in a 100 millisecond bin directly preceding switch closure. FIG. 35 illustrates percent accuracy of the spike decoder when a Poisson and Gaussian model is used.

Figure 36:
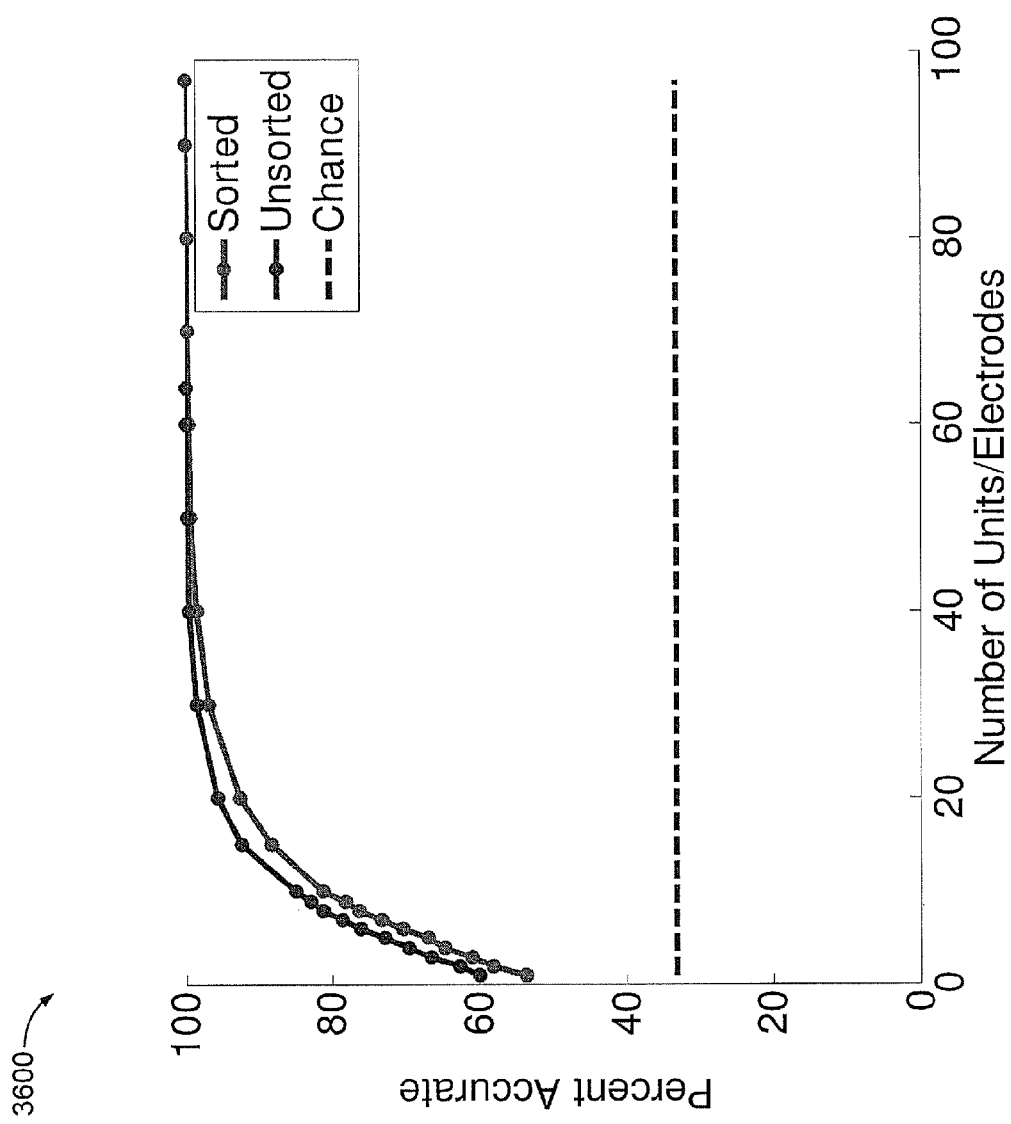
FIG. 36 is a graph of results of using a decoder with Poisson likelihood models when spikes were sorted and left unsorted.

FIG. 36 is a graph 3600 of results of using a decoder with Poisson likelihood models when spikes were sorted and left unsorted. All other parameters were held constant compared to the first analysis. FIG. 35 provides a comparison of accuracy of spike decoding using a Poisson model when spikes are sorted and left unsorted.

In FIG. 36, it can be seen that for lower unit/electrode numbers, the unsorted decode outperforms the sorted decode. As the number of units/electrodes increases, the two methods are similar. This may seem initially counter intuitive. A possible explanation follows. Each electrode may record multiple spikes. In a relatively extreme case of comparing one electrode with one unit, it is likely or possible that a single electrode recording from multiple units may contain more useful information for a decode than a single unit. This effect may diminishe as the number of electrodes and units grows.

Figure 37:
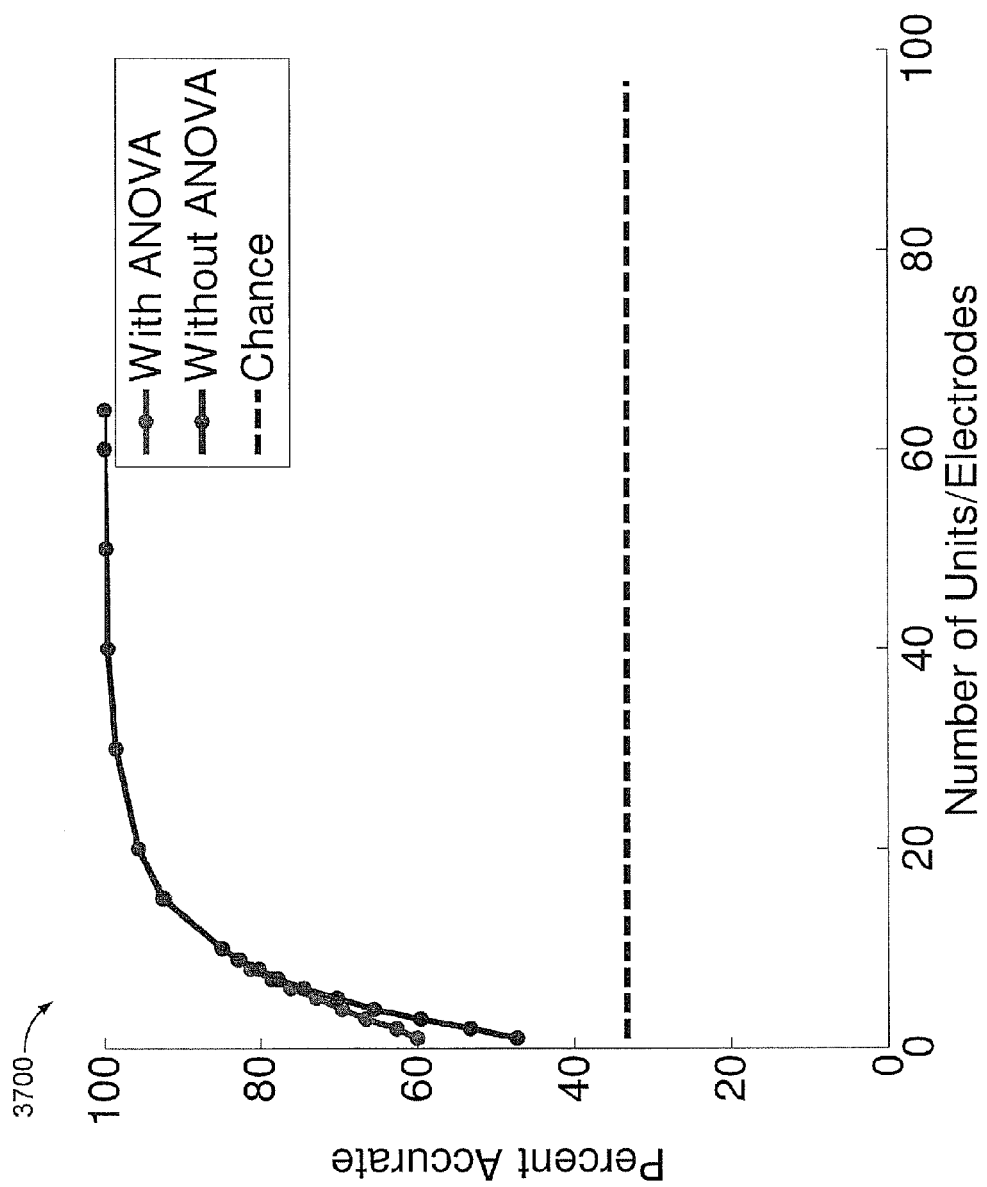
FIG. 37 is a graph to compare decode results when using and not using an ANOVA test to reduce data dimensionality.

FIG. 37 is a graph 3700 to compare decode results when using and not using an ANOVA test to reduce the dimensionality of data. This was done with unsorted spikes and spikes were counted as in the first analysis.

As described above, if no units were left after an ANOVA test, the analysis for that repetition was skipped. This is analogous to performing an ANOVA test on training data collected from a relatively old array, determining there were no good units on the array, and then determining to not decode.

FIG. 37 illustrates a comparison of the accuracy of the spike decoder when spike sorting was ignored and ANOVA was and was not used to weed out limits.

In FIG. 37, it can be seen that the use of ANOVA improves decode accuracy with low unit numbers, possibly by determining when there are no "good" units with which to perform a decode and thereby preventing a bad decode from entering the analysis. In FIG. 37, it can also be seen that the use of ANOVA does not impair decode performance as the number of units increases. While decode accuracy does not suffer, there may be a practical benefit from the use of ANOVA when many units are presented to the decoder. By selecting only those units which have relatively low p-values, the number of units use in the decode can be lowered, reducing computational burden.

Figure 38:
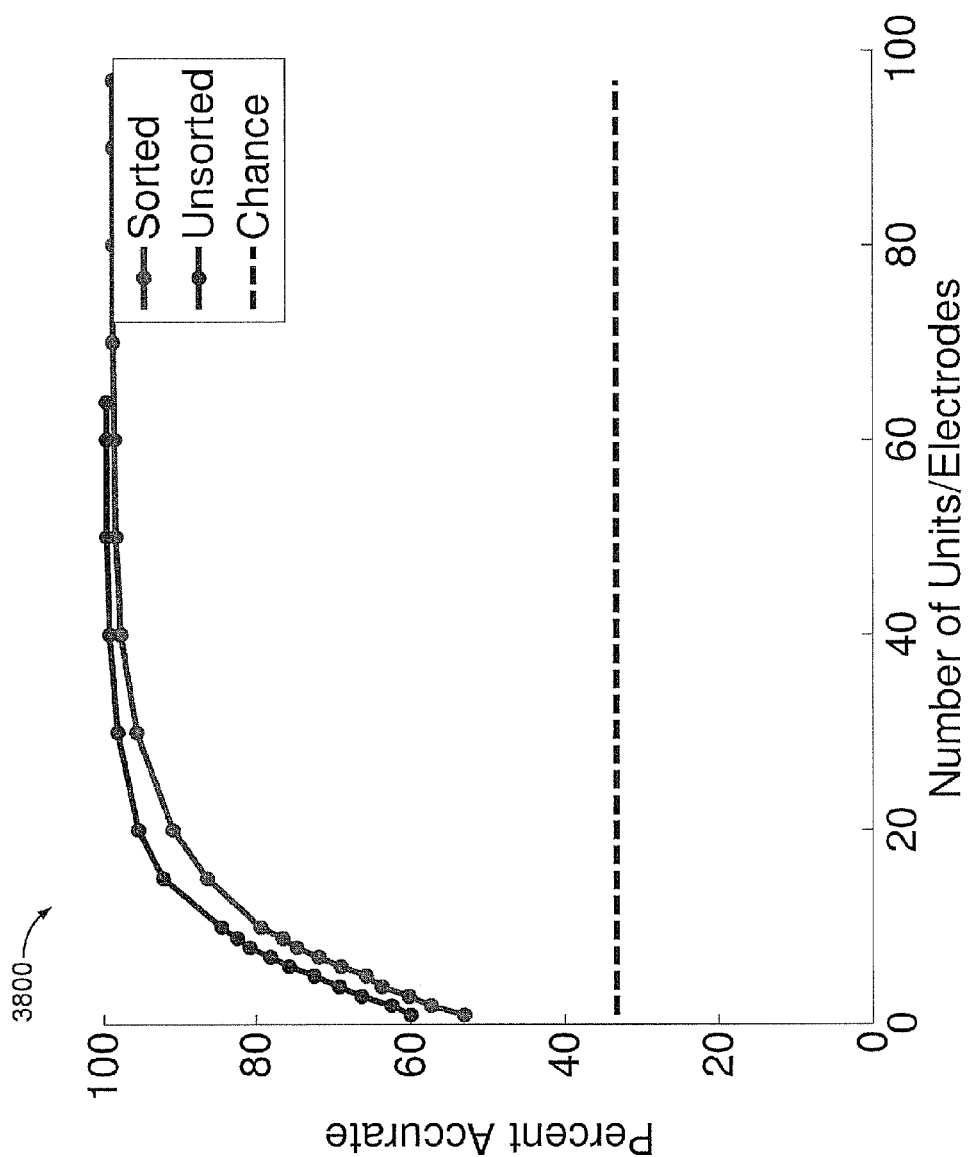
FIG. 38 is a graph of an analysis where a decode with sorted and unsorted spikes was performed.

FIG. 38 is a graph 3800 of an analysis where a decode with sorted and unsorted spikes was again performed. In this decode, multivariate Gaussian likelihood models were used. All other parameters were held constant. FIG. 38 illustrates a comparison of the accuracy of the spike decoder using a Multivariate Gaussian model when spikes are sorted and left unsorted.

Figure 39:
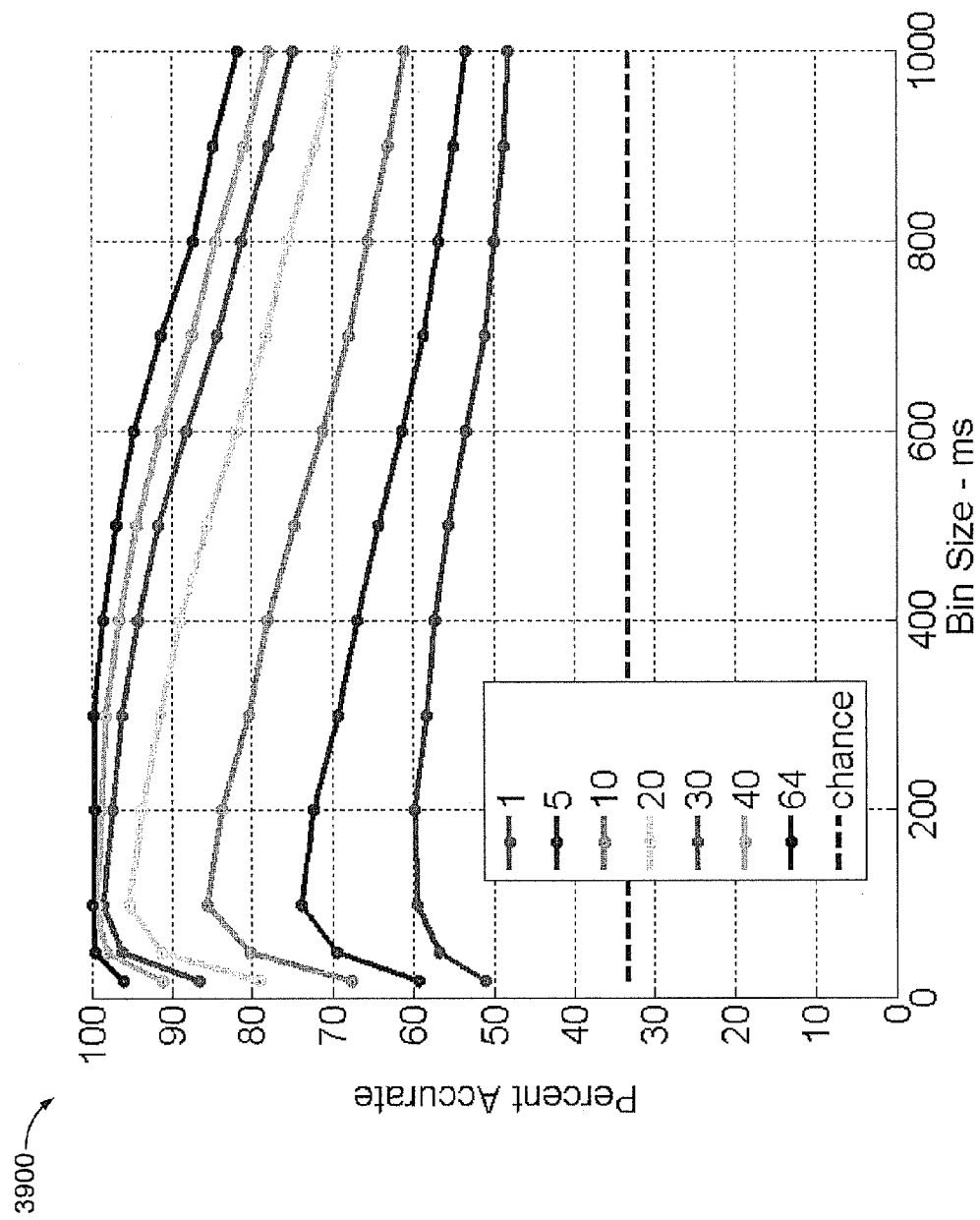
FIG. 39 is a graph showing results of examining bin size on decoder performance.

FIG. 39 is a graph 3900 showing results of examining bin size on decoder performance. FIG. 39 illustrates a comparison of the accuracy of the spike decoder at different bin sizes, where each curve represents presenting the decoder with a different number of units.

For FIG. 39, the decoder used Poisson likelihood functions, unsorted spikes and an ANOVA test to reduce the dimensionality of data. Bin size was then varied. In all cases the closing edge of the bin was aligned with switch closure. Thus, all spikes that were counted preceded switch closure. The analysis was repeated for different numbers of units that were included in the decode. The results show that for this particular dataset, accuracy saturates for bin sizes around 100 milliseconds in length.

(4) LFP Channel Dropping Analysis

As with the spike decoder, a LFP component decoder was analyzed with URMC switch task data. The number of channels included in the decode was examined.

Ten fold cross validation was performed for each test point. To simulate the dropping of channels, an appropriate number of channels were selected at random to feed into the decoder. For each fold, between 100 to 150 repetitions were performed, roughly proportional to the reciprocal of the number of units presented to the decoder, to get an average accuracy value. This was then repeated for each fold to produce the values for the test points plotted in the figure below.

Figure 40:
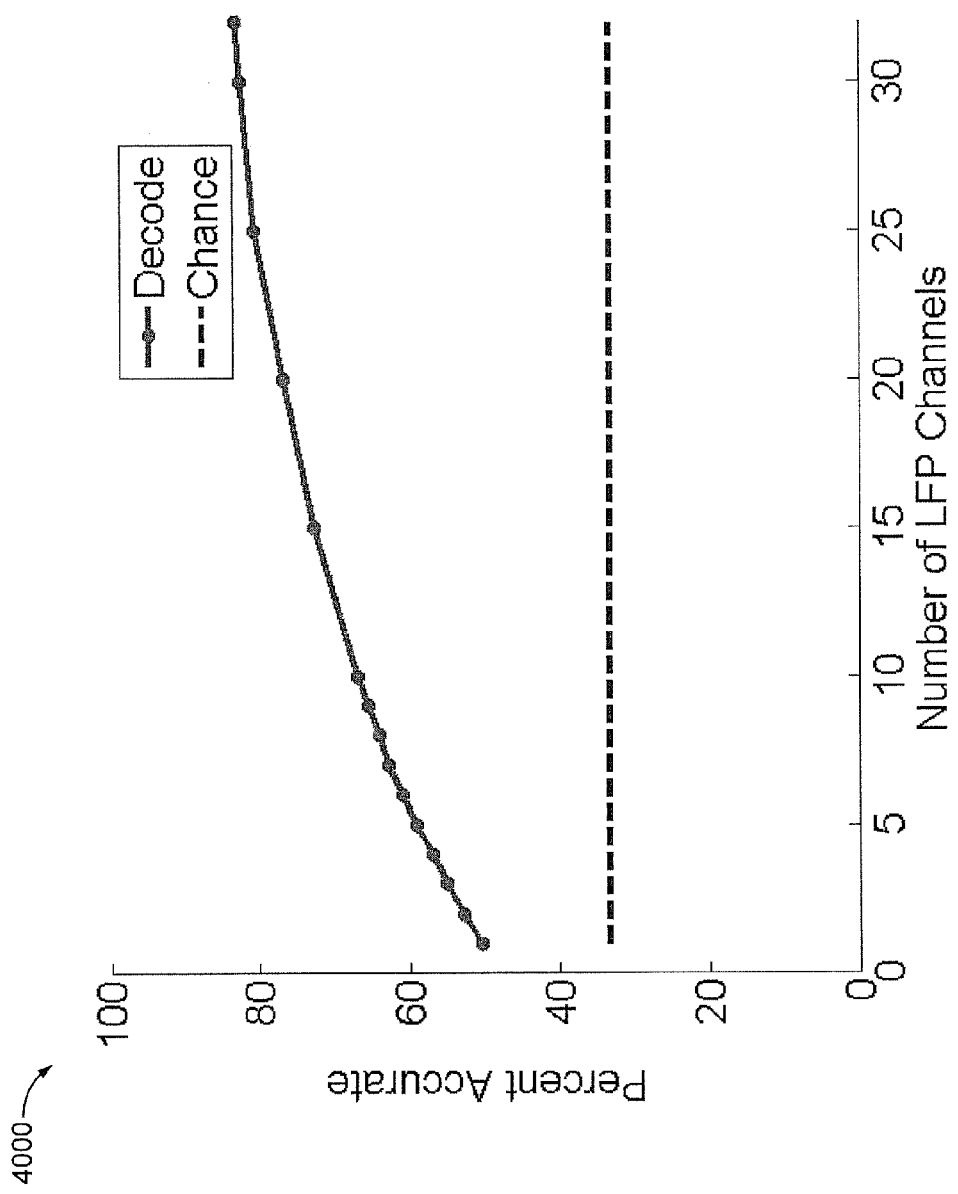
FIG. 40 is a graph of a comparison of accuracy of an LFP decoder as collections containing different numbers of channels are randomly formed and presented to the decoder.

FIG. 40 is a graph 4000 of a comparison of the accuracy of the LFP decoder as collections containing different numbers of channels are randomly formed and presented to the decoder.

As with the spike decode, because of the use of an ANOVA test, the number of channels presented to the decoder, and given on the ordinate axis of FIG. 40, was an upper bound on the number of channels actually used in the decode.

(c) Example Algorithm Implementation

In the description below, component algorithms are described as placed or implemented within corresponding configurable subsystems. Alternatively, or additionally, component algorithms may be placed or implemented within a signal analysis configurable subsystem, and may be run simultaneously in a fusion approach. The former more readily permits unit testing, validation, and verification of each component algorithm before more sophisticated data and decision fusion techniques are undertaken.

(i) Spike Decoder Signal Analysis Configurable Subsystem

Figure 41:
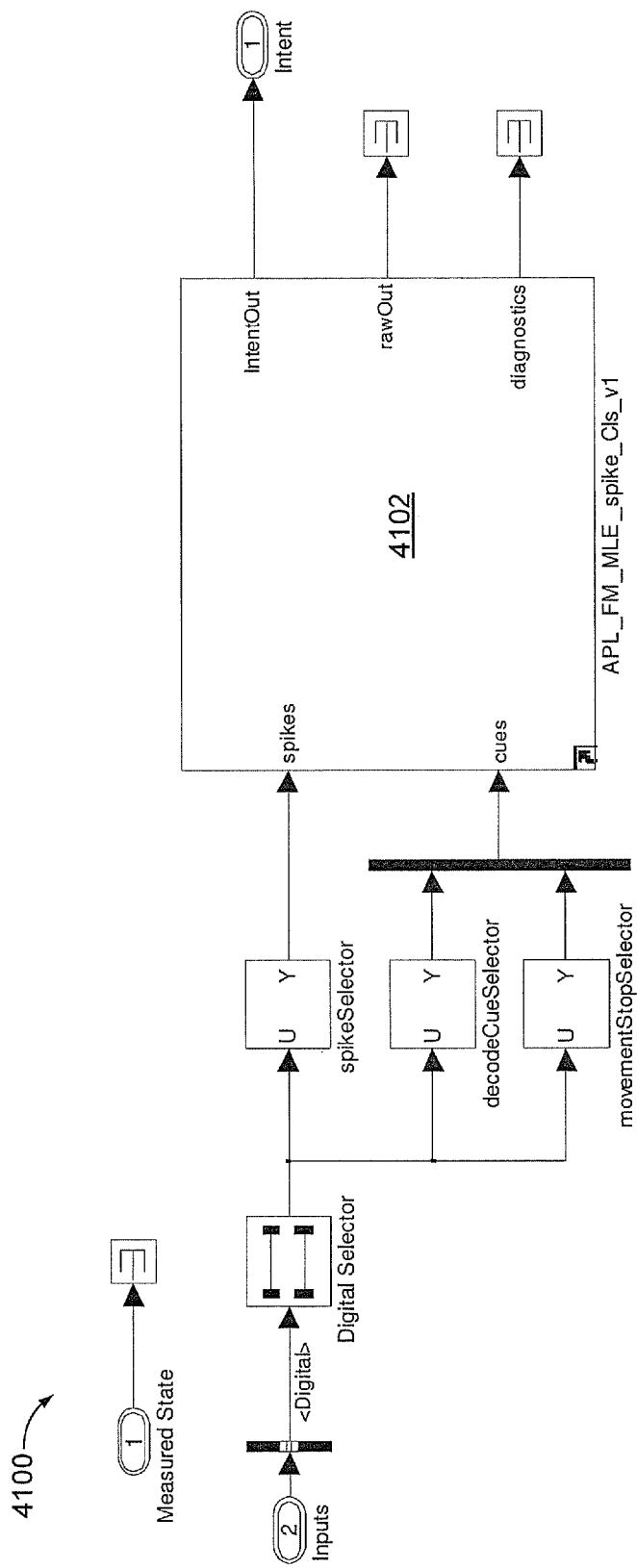
FIG. 41 is a block diagram of a FL_APL_FM_MLE_Spike_Cls configurable subsystem.

A spike decoder may be implemented within a configurable subsystem FIG. 41 is a block diagram of a FLAPL_F-M_MLE_Spike_Cls configurable subsystem 4100, which may include a spike decoder. Configurable subsystem 4100 may represent an instantiation of a signal analysis block in a multi-block model of a VIE, and may receive inputs on an inputs bus and send commands to a controls block over an intent bus.

Configurable subsystem 4100 may include a digital sub-bus of the inputs bus and a selector to select a spike signal, a decodeCue signal, and a movementStop signal.

The spike signal, the decodeCue signal, and the movementStop signal may be provided to block 4102, which may represent a spike component decoder, denoted here as APL_FM_MLE_spike_Cls_v1.

Block 4102 receives the spike and cues signals, and outputs an intent bus and a rawOut bus. Block 4102 may output a diagnostics bus. Where fusion is not performed, and the spike component decoder is implemented to drive the limb by itself, the rawOut bus may be unused.

Figure 42:
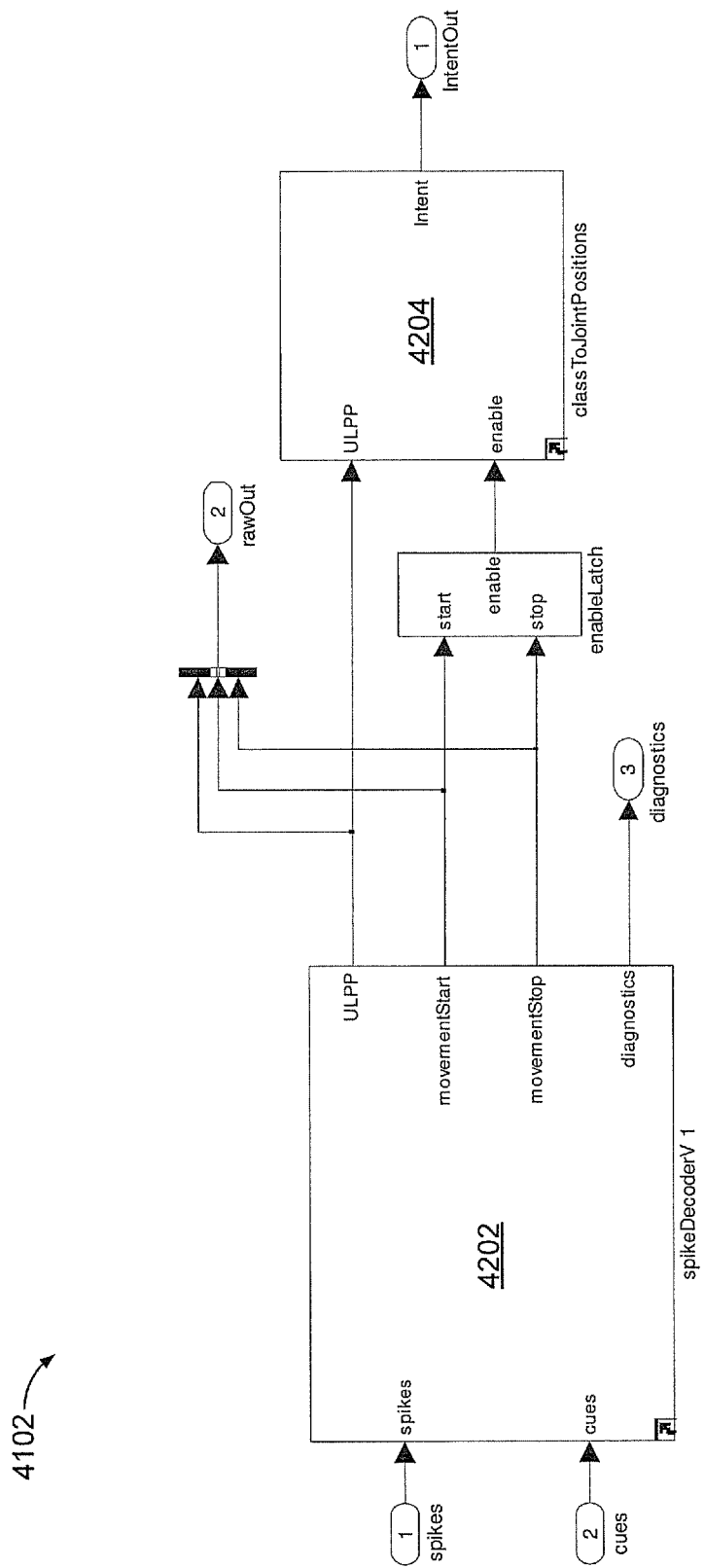
FIG. 42 is a block diagram of a portion of the configurable subsystem of FIG. 41, including a decoder block and an intent mapping block, denoted here as spikeDecoderV1 and classToJointPositions, respectively.

FIG. 42 is a block diagram of block 4102, including a decoder block 4202 and an intent mapping block 4204, denoted here as spikeDecoderV1 and classToJointPositions, respectively, which are described further below.

The table immediately below lists names of parameters that may be used by configurable subsystem 4100. One or more of the parameters may be automatically generated during training.

Example Parameters Used by Configurable Subsystem 4100

| Variable Name | Description |
|---|---|
| aplMLESpkDecode.baseSmpRate | (non-tunable) This is the base sample time the algorithm |

| Variable Name | Description |
|---|---|
| | runs at in seconds. |
| aplMLESpkDecode.intentRate | (non-tunable) The rate that commands should be sent to controls on the Intent Bus in seconds. |
| aplMLESpkDecode.nRawUnits | (non-tunable) This is the number of raw channels sent into the Spikes input port. |
| aplMLESpkDecode.goodChs | (non-tunable) The unit numbers that should be used in the decode. Any unit numbers that are not placed in this vector will be weeded out to avoid unnecessary computational burden. Unit numbers are one-indexed, with channel one being the first channel that appear on the spike input line, channel two the second, etc.. |
| aplMLESpkDecode.binSize | (non-tunable) This is the number of model time steps that should make up a bin when counting spikes. (Example: If baseSmpRate is .001 and bin sizes of 10 milliseconds are desired, then binSize of 10 would be used). |
| aplMLESpkDecode.nCueDelaySmps | (non-tunable) nCueSmpDelays provided during training. |
| APL_MLE_SPK_MEANS | Described Above |
| APL_MLE_SPK_LOG_MEANS | Described Above |
| APL_MLE_SPK_LOG_PRIORS | Described Above |
| APL_MLE_SPK_CLASS_KEY | Described Above |
| APL_MLE_SPK_N_JOINTS_PER_CLASS | Described Above |
| APL_MLE_SPK_JOINT_MAP | Described Above |
| APL_MLE_SPK_MAG_MAP | Described Above |
| APL_MLE_SPK_JOINT_MAP_INC_NULL_CLASS | Described Above |

(ii) LFP Signal Analysis Configurable Subsystem

Figure 43:
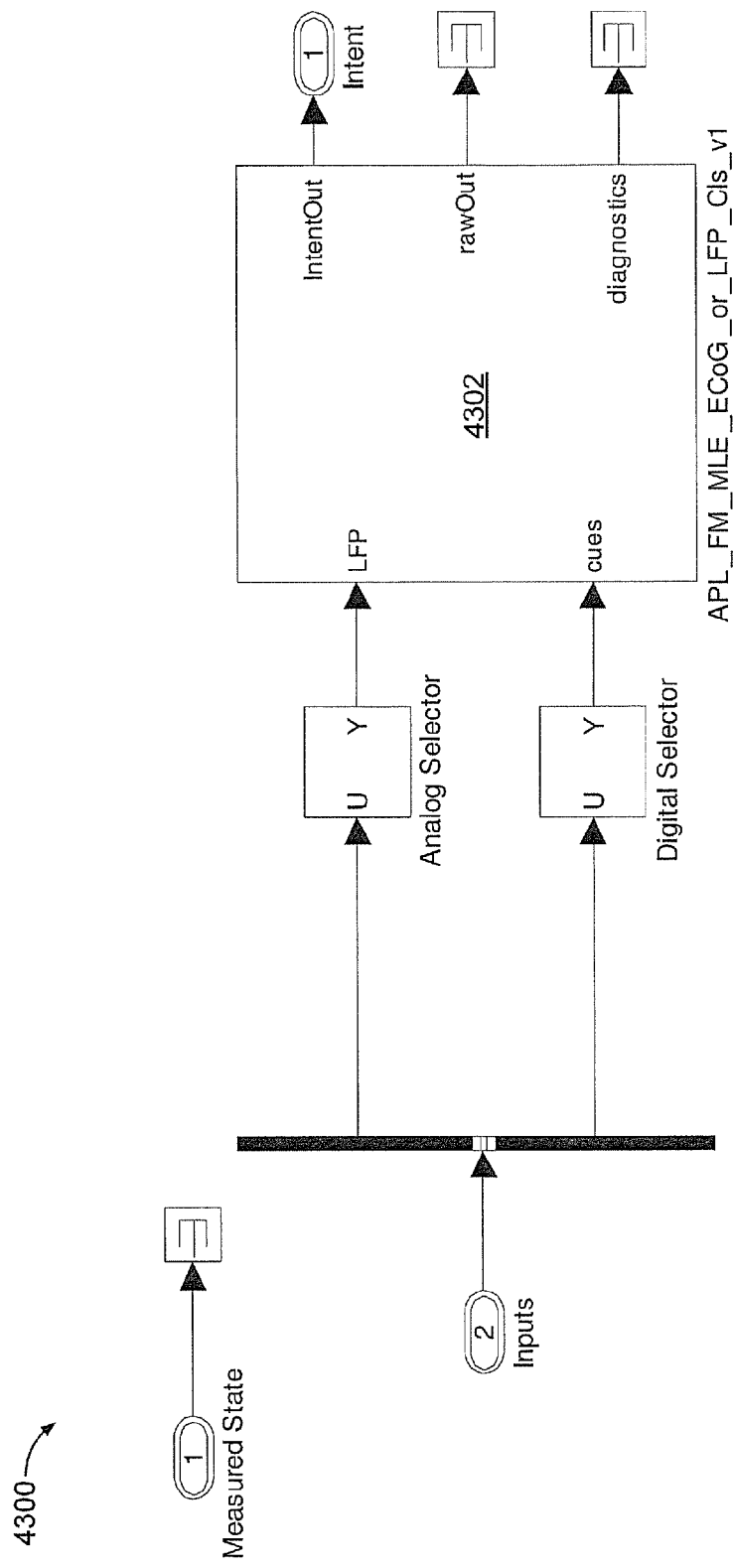
FIG. 43 is a block diagram of a FL_APL_FM_MLE_LFP_Cls configurable subsystem, which may include a LFP decoder.

FIG. 43 is a block diagram of a FL_APL_FM_MLE_LFP_Cls configurable subsystem 4300, which may include a LFP decoder.

Configurable subsystem 4300 may include a digital sub-bus of the inputs bus and a selector to select cues signals. In the example of FIG. 43, selector outputs trigger cue as channel 1 and a movementStop cue as channel 2. An analog bus is may be routed another selector where LFP channels may be selected.

Selected signals may be provided to a block 4302, denoted here as APL_FM_MLE_ECoG_or_LFP_Cls_v1, which may represent a component decoder block. Block 4302 may be configured to perform LFP or ECoG decoding.

Figure 44:
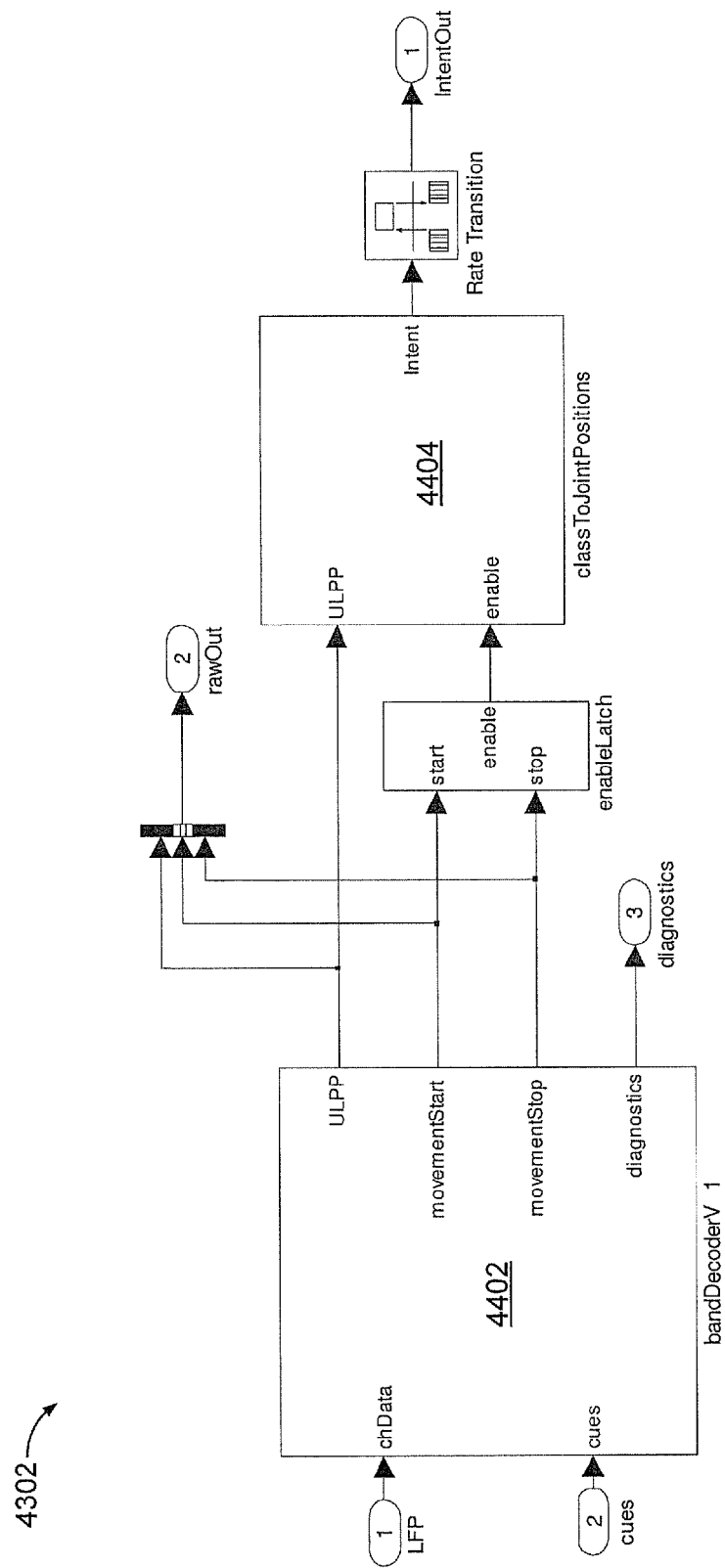
FIG. 44 is a block diagram of a portion of the configurable subsystem of FIG. 43, including a decoder block and an intent mapping block, illustrated here as bandDecoderV1 and classToJointPositions, respectively.

FIG. 44 is a block diagram of block 4302, including a decoder block 4402 and an intent mapping block 4404, illustrated here as bandDecoderV1 and classToJointPositions, respectively, which are described further below.

The table immediately below lists names of parameters that may be used by configurable subsystem 4300. One or more of the parameters may be automatically generated during training.

Example Parameters Used by Configurable Subsystem 4300

| Variable Name | Description |
| --- | --- |
| aplMLELFPDecode.baseSmpRate | (non-tunable) This is the base sample time the algorithm runs at in seconds. |
| aplMLELFPDecode.intentRate | (non-tunable) The rate that commands should be sent to controls on the Intent Bus in seconds. |
| aplMLELFPDecode.nRawChs | (non-tunable) This is the number of raw LFP channels that are initially provided to the decode before any down selection. |
| aplMLELFPDecode.goodChs | (non-tunable) The channels of LFP data that should be used in the decode. Channels not listed in this vector will be weeded out to avoid unnecessary computational burden. |
| APL_MLE_LFP_ENABLE_NOTCH_FTR | Described Above |
| aplMLELFPDecode.notchFtr | (non-tunable) This is a structure with the following fields:<br>bCoefs - The feed-forward coefficients of the notch filter.<br>aCoefs - The feedback coefficients of the notch filter<br>rate - The rate the notch filter runs at in seconds. |
| APL_MLE_LFP_ENABLE_AA_FTR | Described Above |
| aplMLELFPDecode.aaFtr | (non-tunable) This is a structure with the following fields:<br>bCoefs - The feed-forward coefficients coefficients of the anti-aliasing<br>aCoefs - The feedback coefficients of the anti-aliasing filter<br>rate - The rate the notch filter runs at in seconds. |
| aplMLELFPDecode.dwnSmpFactor | This is the integer value the LFP data should be down-sampled by. Down sampling will be applied after notch and anti-alias filtering |
| aplMLELFPDecode.bandPassFtrs | (non-tunable) This is a 1 by 5 structure which contains the parameters to use for each of 5 possible filters used to break up the LFP signal into bands.<br>enable - 1 if a filter should be used. 0 if a filter should not be used.<br>aCoefs - The feed-forward coefficients of the filter. If enable is set to 0, a place holder aCoef value must still be provided.<br>bCoefs - The feedback coefficients of the filter. If enable is set to 0, a place holder aCoef value must still be provided.<br>rate - The rate the filter should run at (in seconds). If enable is set to 0, a place holder rate value must still be provided. |
| aplMLELFPDecode.ftrSelector | (non-tunable) For the real-time decode, band one for all channels is filtered and placed in a vector, band two for all channels is filtered and then added to the end of the existing feature vector, and this is repeated for all bands. However, the decode only takes place on a few of the channel/band features and the feature vector that the classifier has been trained on may be different than the order of features output by the band-pass filters. Thus, to appropriately down select features and re-arrange them for later decode, a selector block is required. This parameter provides the index selector for this selector block. Specifically, it contains the following fields:<br>selInds - This is an array determining what incoming channel/band features are passed through and in what order. The order that feature indices are specified in this vector will be the order they are sent to the decoder in. If a feature number is not represented in this vector, it will not be sent to the decoder.<br>inputSize - This is the size of the incoming feature vector before down-selection. It can be computed as the number of LFP channels that are passed through the initial channel down-selector multiplied by the number of bands extracted from each channel.<br>To make things clear, a simple example will be provided. In this example, 2 LFP channels are used and two bands (first, a 25-50 Hz band and |

-continued

| Variable Name | Description |
| --- | --- |
| | second, a 75-100 Hz band) are extracted from each. Thus, the feature vector coming into the selector block would first have the 25-50 Hz band from channel 1, next the 25-50 Hz band from channel 2, next the 75-100 Hz band from channel 1 and finally the 75-100 Hz band from channel 2. However, in this example, the decoder has been trained on a feature vector composed of the power of the 75-100 Hz band from channel 1 and then 25-50 Hz band from channel 2. The ftrSelector would be used to form a proper feature vector for decode by setting the inputSize field to 4 and the selInds field to [3 2]. |
| aplMLELFPDecode.nCueDelaySmps | (non-tunable) nCueSmpDelays provided during training. |
| aplMLELFPDecode.nSmpsInFtrMean | (non-tunable) The number of band-passed samples that should be included in the mean value. |
| APL_MLE_LFP_CLASS_MEANS | Described Above |
| APL_MLE_LFP_CLASS_INV_COVS | Described Above |
| APL_MLE_LFP_CLASS_LOG_NORM_CONSTS | Described Above |
| APL_MLE_LFP_CLASS_LOG_PRIORS | Described Above |
| APL_MLE_LFP_CLASS_KEY | Described Above |
| APL_MLE_LFP_N_JOINTS_PER_CLASS | Described Above |
| APL_MLE_LFP_JOINT_MAP | Described Above |
| APL_MLE_LFP_MAG_MAP | Described Above |
| APL_MLE_LFP_JOINT_MAP_INC_NULL_CLASS | Described Above |

(iii) ECoG Signal Analysis Configurable Subsystem

A FL_APL_FM_MLE_ECoG_Cls configurable subsystem may include a ECoG decoder, which may be substantially similar or identical to the LFP decoder described above with respect to FIGS. 43 and 44, with the exception that in parameter names, the character string LFP may be replaced with ECoG.

(iv) spikeDecoderV1 Block

Figure 45:
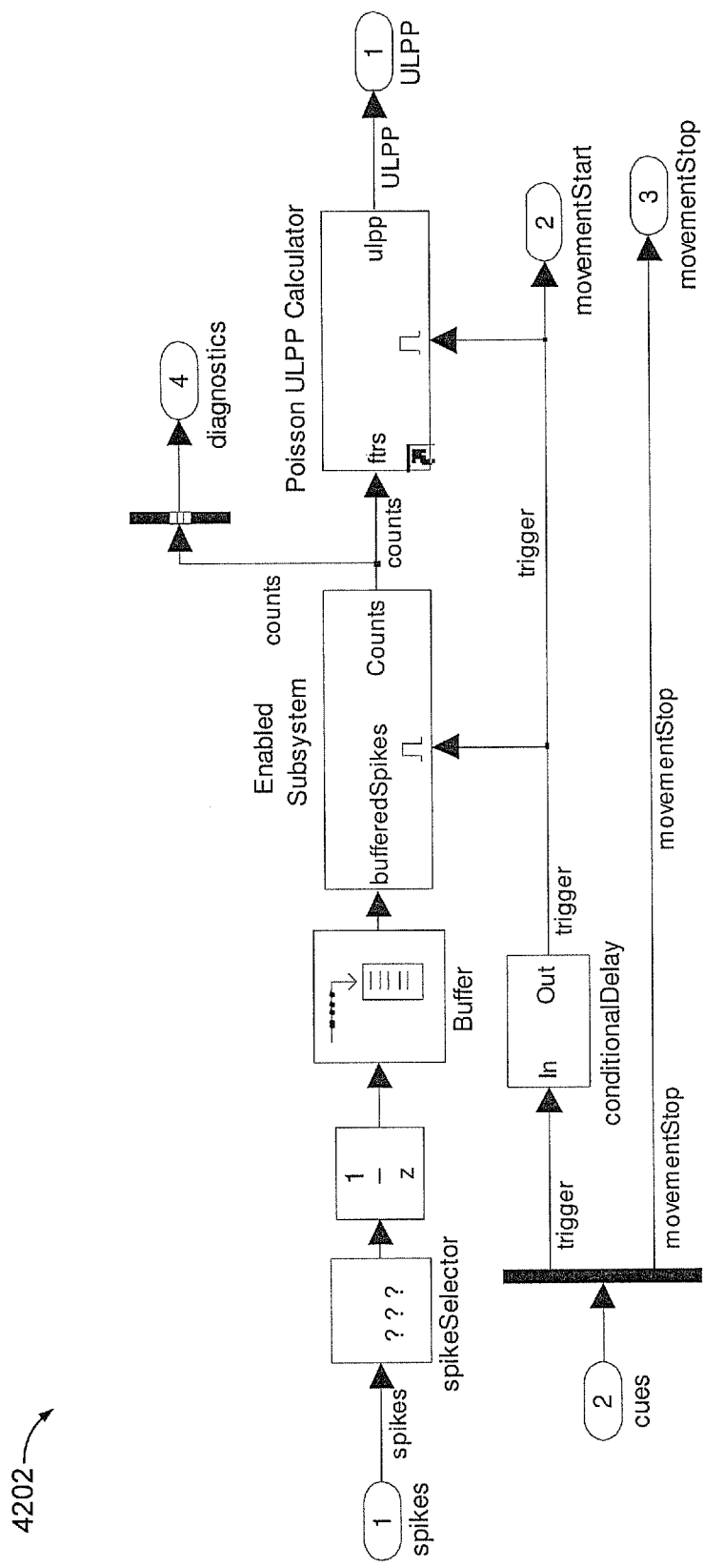
FIG. 45 is a block diagram of the spikeDeocerV1 block of FIG. 42.

FIG. 45 is a block diagram of decoder block 4202 (FIG. 42), also referred to herein as a spikeDeocerV1 block.

Decoder block 4202 may receive spikes, a decode trigger and movement stop cues, and to output ULPP values.

The movementStop cue may be unused by decoder block 4202, and may be passed thru for use by blocks downstream.

The trigger cue may be passed through a conditionalDelay block to delay the trigger pulse a requested number of samples (aplMLESpkDecode.nCueDelaySmps) before it reaches a spike counter block and a Poisson ULPP calculator.

When spikes arrive in the model, they may be initially passed through a selector block to weed out any units that are not used in the actual decode. This may free up memory and/or computational resources. A unit delay may be applied to incoming spike trains, such as to ensure that when spikes are counted in bins, the leading edge will be inclusive and the trailing edge will be exclusive, which may correspond to how training is performed. Spikes may then be sent to a buffer to keep a record of the last N samples of spike trains for each unit, where N is determined by the binSize used in the decode.

An enabled subsystem may be configured to access the buffer and count the number of spikes for each unit. The enabled subsystem may count spikes when triggered by the potentially delayed trigger pulse rather than constantly. This may conserve computational resources.

After spikes are counted, a Poisson ULPP Calculator block may access the spike counts and produce ULPP values for each class. The ULLP values may be computed when a trigger pulse is received, and the ULPP values may be held between trigger pulses.

(v) bandDecoderV1 Block

Figure 46:
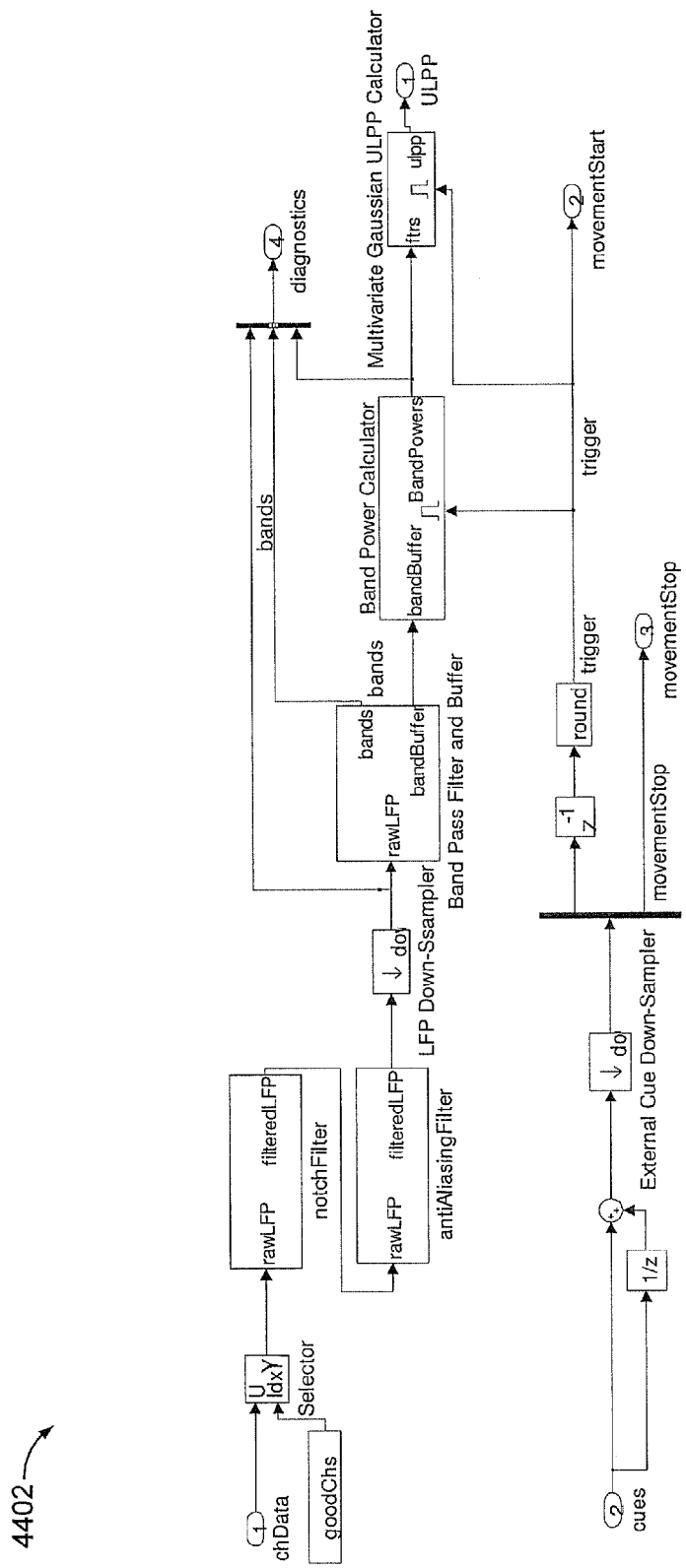
FIG. 46 is a block diagram of the bandDecoderV1 block of FIG. 44.

FIG. 46 is a block diagram of decoder block 4402 (FIG. 44), also referred to herein as a bandDecoderV1 block.

LFP data may be received on a chData input port. LFP channels may be down selected to remove any channels that are not used in the decode. Remaining LFP channels may be sent through a notch filter to remove power line noise. LFP data may then be down sampled, which may reduce downstream computational load. Where down sampling is implemented, an anti-aliasing filter may be applied. The notch filter and anti-aliasing filters may be configured to permit disabling at run-time. When the notch filter and anti-aliasing filters are disabled, LFP data may pass through them unchanged.

Where down sampling undesired, a down sample factor of 1 may be provided. Parameters that determine the down sample factor in the LFP and ECoG algorithms are referred to herein as aplMLELFPDecode.dwnSmpFactor and aplMLEECoGDecode.dwnSmpFactor, respectively.

After down sampling, the LFP channels may be sent to a band pass filter and buffer block. The band pass filter and buffer block may apply band pass filters specified in a parameter referred to herein as aplMLELFPDecode.bandPassFtrs/aplMLEECoGDecode.bandPassFtrs. The band pass filter and buffer block may also select appropriate band/channel combinations using a parameter referred to herein as aplMLELFPDecode.ftrSelector/aplMLEECoGDecode.ftrSelector, and may buffer the band/channel combinations. A buffer length may be determined by a frame length used to calculate average band power.

The decoder may review two cues, which may each undergo down sampling as applied to the LFP data. The cues may then be sent through a selector block where the first cue is used for the trigger signal and the second cue is sent out of the block as the movementStop signal.

The down sampled trigger may then be passed through a delay block, illustrated here as a unit delay, to delay the trigger sample by a number of samples indicated in a parameter referred to herein as aplMLELFPDecode.nCueDelaySmps/aplMLEECoGDecode.nCueDelaySmps. The signal may then be used to trigger the band power calculator and the ULPP calculator.

When enabled by the trigger signal, a band power calculator may access the channel/band signals buffered in the band pass filter and buffer block to calculate the average power for the signals. The power of these signals may be calculated when the trigger signal is set high, which may conserve computational resources. After the band powers are calculated, a Multivariate Gaussian ULPP Calculator block may calculate ULPP values. The ULPP values may be calculated when a trigger pulse is received, and ULPP values may be held between pulses.

(vi) Intent Block

Figure 47:
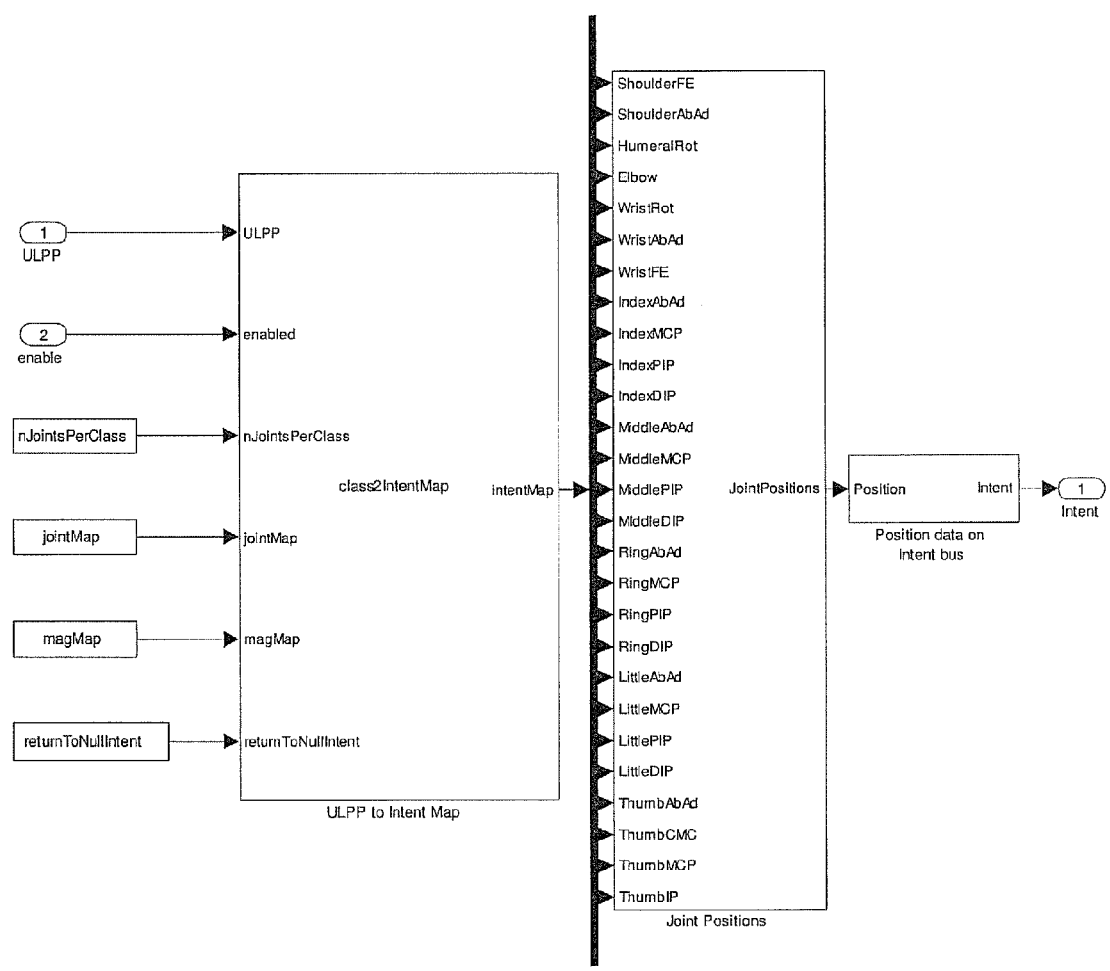
FIG. 47 is a block diagram of an intent block, illustrated here as a classToJointPositions block, which may correspond to the intent block of one or more of FIGS. 42 and 44.

FIG. 47 is a block diagram of an intent block 4702, illustrated here as a classToJointPositions block, which may correspond one or more of block 4204 (FIG. 42) and block 4404 (FIG. 44).

Intent block 4702 receives ULPP values and enable signal. When the enable signal is high, intent block 4702 selects the most likely class from a vector of ULPP values and generates a formatted intent command using intent mapping parameters described above.

(d) Experimental Performance Metrics

Experimental performance metrics for spike and LFP component decoders are provided below. Experimental metrics were not generated for an ECoG component decoder.

The algorithms were evaluated with switch task data obtained from the University of Rochester Medical Center. The following description of the switch task data is based on a task description provided by Vikram Aggarwal, at the Johns Hopkins University (see Mollazadeh et al. described above, for additional information):

Monkeys sat in a primate chair with their head restrained. A box with three switches mounted on the front panel was positioned approximately 6 inches in front of the monkey at eye level. The switches were aligned horizontally from right to left in the following order for files m001 to m077: vertical toggle switch, push button switch, horizontal toggle switch. For files m078 to m081 switches were arranged in the following order: horizontal toggle, vertical toggle, push button. For files m082 to m088 switches were arranged in the following order: push button, horizontal toggle, vertical toggle. Reaches were made with only the right arm; the left arm was not restrained, but was enclosed within the primate chair. The monkey could move the right arm at anytime, and was not required to hold an initial position between trials or during cue presentation.

For the results presented here, switch 1 is a vertical toggle switch, switch 2 is a push button and switch 3 is a horizontal toggle switch.

Using 10 fold cross validation, the overall accuracy for the spike component algorithm using unsorted spike data from 64 electrodes was 99.85%. The confusion matrix is provided in the table immediately below.

Confusion Matrix for Spike Decoder on URMC Switch Task Data

|  | Switch 1 | Switch 2 | Switch 3 |
| --- | --- | --- | --- |
| Switch 1 | 11050 | 0 | 0 |
| Switch 2 | 0 | 11050 | 0 |
| Switch 3 | 0 | 50 | 10850 |

Again using 10 fold cross validation, the overall accuracy for the LFP component algorithm using 32 LFP channels was 83.18%. The confusion matrix is provided in the table immediately below.

Confusion Matrix for LFP Decoder on URMC Switch Task Data

|  | Switch 1 | Switch 2 | Switch 3 |
| --- | --- | --- | --- |
| Switch 1 | 18700 | 2000 | 1400 |
| Switch 2 | 1700 | 17800 | 2600 |
| Switch 3 | 1000 | 2400 | 18400 |

Features of the experimentally evaluated spike component decoder include:
  computationally light;
  adjusting the algorithm to take into account individual unit lags can be easily performed;
  direct path exists for building in the capability to add and remove units on-the-fly.
  relatively fast training times (<1 minute);
  robust to the dropping of units;
  no decrease in performance when spike sorting is removed;
  training times is not a factor of the number of units included in the decode;
  the use of ANOVA reduces dimensionality of feature vectors, and thus computational load, while maintaining performance;
  assumes conditional independence among units;
  does not take into account individual unit lags; and
  does not allow for on-the-fly adding and dropping of units.

One or more of the above-listed features may differ with other spike decoder implementations.

Features of the experimentally evaluated LFP component decoder includes:
  direct path exists for building in the capability to add and remove LFP channels on the fly;
  does not assume conditional independence among features;
  computationally light;
  the use of ANOVA reduces dimensionality of feature vectors, and thus computational load, while maintaining performance;
  relatively fast training times (<1 minute);
  fairly robust to the dropping of LFP channels;
  does not allow for on-the-fly adding and dropping of LFP channels; and
  training times are a factor of the number of units included in the decode.

One or more of the above-listed features may differ with other LFP decoder implementations.

Component algorithms may be implemented individually and corresponding decisions may be fused in a data fusion module. Alternatively, or additionally, a mathematical model may be implemented to decode from spike, LFP and ECoG data simultaneously, without a data fusion module.

5. Example 4

Spike and LFP Decision Fusion

Decision fusion is described below with reference to motor decoding algorithms FM MLE spike Cls and FM MLE LFP Cls, described above, and with respect to a fusion algorithm referred to herein as a decision fusion FM class. In the examples below, "FM" refers to finger movement, "MLE refers to maximum likelihood estimation, "LFP" refers to local field potential, and "CL" refers to class.

The fusion algorithm described below is a discrete decision fusion algorithm that performs decision fusion on two classifiers, each of which decode three classes. The decision fusion algorithm may receive unnormalized log posterior probability (ULPP) vectors from the two motor decoders, and may output a decision vector.

Methods and systems disclosed herein are not, however, limited to the example fusion algorithm disclosed below.

(a) Algorithm Overview

The decision fusion FM class first converts the ULPP values from the decoders to normalized posterior probabilities so that they are no longer in log space and sum to one. Then it fuses the probability vectors into a decision vector using a weighted average where the weights are optimized by training and sum to one. The index of the decision vector that contains the maximum value corresponds to the final class decision, and the maximum value of the decision vector can be interpreted as the confidence of the decision which can be used to modulate the velocity of the class state transition.

Figure 48:
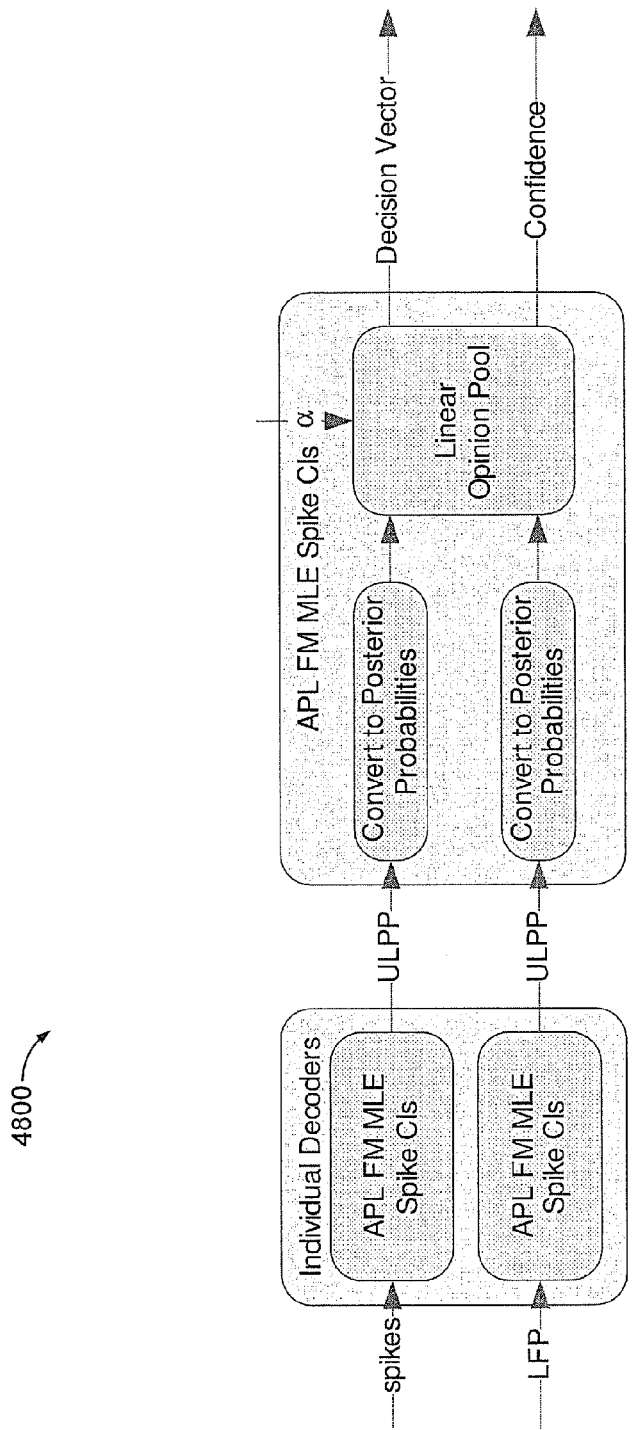
FIG. 48 is a block diagram of a decision fusion algorithm, referred to herein as a FM class algorithm.

FIG. 48 is a block diagram of a decision fusion algorithm 4800, referred to herein as a FM class algorithm.

A spike classifier weight is denoted $\alpha$, a LFP classifier weight is denoted $1-\alpha$, an $\alpha$ may include a tunable parameter.

A decision vector may be a [3,1] vector, and a maximum value index corresponds to a most likely class.

Inputs to decision fusion algorithm 4800 may include unnormalized log posterior probabilities from spike and LFP decoders. Each ULPP vector may be a [3,1] vector.

Weighting of the ULPP vectors may be a configurable algorithm parameter, referred to herein as APLLOP_Weights, which may have a size [2,1]. The elements may sum to one.

Decision fusion algorithm 4800 may be implemented to:
  operate on decision vectors with the same dimensionality;
  produce a decision output that has the same length as the input vectors;
  run at the output rate of its individual decoders;
  not compete for the same lines on the intent bus as other decision fusion algorithms running concurrently; and/or
  use a linear opinion pool as its decision fusion algorithm.

(b) Design Approach

Methods of designing a discrete decision fusion algorithm are disclosed below.

Discrete decision fusion data sets may be analyzed with one or more of the flowing discrete decision fusion algorithms:
  the Sum Rule;
  the Product Rule; the Median Rule;
  Majority Vote; and
  the Linear Opinion Pool.

Where the fusion algorithm involves two classifiers and three classes, many of these discrete decision fusion algorithms become relatively trivial. The sum rule is always a special case of the linear opinion pool. Similarly, the product rule is a special case of the log opinion pool. For two classifiers, the sum rule and median rule are equivalent and the majority vote becomes a unanimous vote. The latter will only achieve the performance of the best individual classifier. The product rule is the sum rule in log space. The only analysis that needs to be performed is on the linear opinion pool and the log opinion pool. Also, for a two-classifier problem, the opinion pools simplify to having one weight, a, since the weight of the other classifier will be $1-\alpha$ to satisfy the criterion that the weights sum to unity. It would be expected that the log opinion pool would provide similar accuracy to the linear opinion pool but be more sensitive to outliers and therefore less robust. Both methods may be analyzed, but if the log opinion pool can be shown to be less useful, then only the linear opinion pool may be considered.

The spike decoder provides relatively high accuracy when all of the spike units are included. However, spike content tends to degrade over time, on the order of months to years, and it may become necessary to evaluate the spike decoder with a subset of the original spikes. The decision fusion algorithm may be designed to optimally fuse the decisions independent of the spike decoder accuracy.

Design of the algorithm may include evaluating the linear opinion pool and the log opinion pool using decisions from the LFP and spike decoders, which are generated from a 10-fold cross-validation analysis, which uses 9 of the 10 folds for training the individual decoders. This process may be repeated for variations of the set of active spike units, while all LFP channels may be always used. Where the linear opinion pool proves more useful as a decision fusion method, weights that optimize the correct classification percentage as a function of the number of spike units may be determined Optimal weights may generalize by performing a 2-fold cross validation and determining the optimal weights for each of the two training/testing set pairs.

There are multiple ways to assess confidence in the fused decision. A first technique includes treating the posterior probabilities as arbitrary data points and considering the distribution of the data points associated with each of the three classes. Density functions may be estimated, and distribution of data points will determine new decision boundaries instead of taking the class that has the maximum resulting value. While this technique may accurately model a particular data set, it may not generalize well with a limited set of data points, and it may disregard the probabilistic intention of the decision vectors. It may also be more expensive computationally, and more complicated than a second technique described below.

A second technique of assessing the confidence treats the data points as probabilities and preserves original decision boundaries. If the confidence of an individual decoder can be defined as the maximum probability of its raw output, then the confidence of the decision fusion result using the linear opinion pool can be defined as the maximum value of the weighted sum of the probabilities of the individual decoders. In other words, if both decoders agree, then linearly interpolating between the two data points will also agree. If the decoders disagree, then as the weights are swept, the resulting data point will cross a decision boundary and the confidence should be lower because the resulting point will be closer to that boundary.

Figure 49:
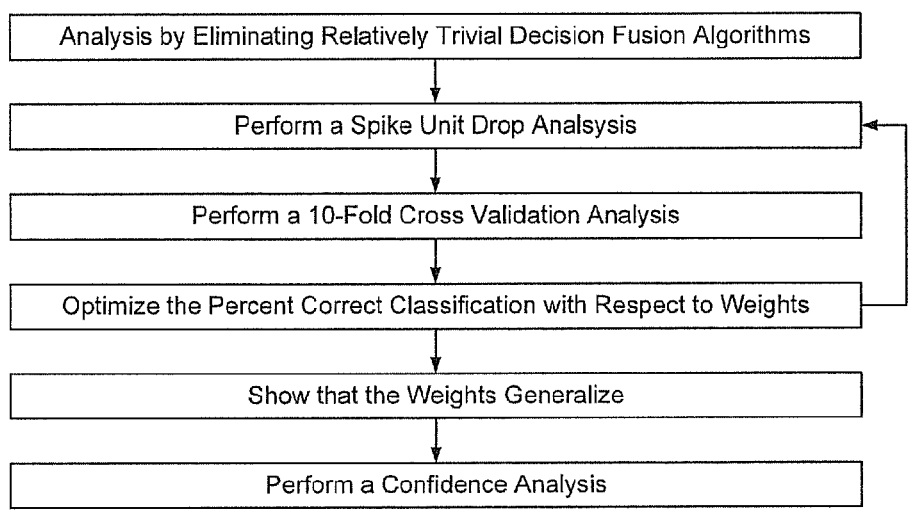
FIG. 49 is a flowchart of a method of designing a decision fusion algorithm.

FIG. 49 is a flowchart of a method 4900 of designing a decision fusion algorithm.

A mathematical description of a discrete fusion algorithm is provided below.

Discrete decision fusion classifiers are described by Kittler in terms of a Bayesian theoretical framework. According to Eq. 3 below, the pattern Z should be assigned to class $\omega j$ provided that the posteriori probability of that interpretation is maximum. Applying Bayes theorem to Eq. 3 yields Eq. 4.

$$\text{assign } Z \to \omega_j \text{ if} \qquad \text{(Eq. 3)}$$
$$P(\omega_j \mid x_1, \ldots, x_R) = \max_{k=1}^{m} P(\omega_k \mid x_1, \ldots, x_R)$$

$$P(\omega_k \mid x_1, \ldots, x_R) = \frac{p(x_1, \ldots, x_R \mid \omega_k) P(\omega_k)}{p(x_1, \ldots, x_R)} \qquad \text{(Eq. 4)}$$

Assuming conditional independence, the classes are highly ambiguous, and equal priors, yields Eq. 5, which is the linear opinion pool also mentioned by Wanas.

$$\text{assign } Z \to \omega_j \text{ if} \qquad \text{(Eq. 5)}$$
$$\sum_{i=1}^{R} w_i P(\omega_j \mid x_i) = \max_{k=1}^{m} \sum_{i=1}^{R} w_i P(\omega_k \mid x_i)$$

The LFP and spike based decoder may output a ULPP vector for each class. The ULPP values may be normalized prior to decision fusion so that the sum of the posterior probabilities in the vector is one. Eq. 6 may be used to accomplish this. Where elements of $e^{ULPP}$ are too large or too small to be represented with double precision floating point values, normalization may first be accomplished without taking the numbers out of log space using the approximation provided by Eq. 7 from Primeaux.

Eq. 6 may be used for normalization and linearization of a ULLP vector:

$$\frac{e^{ULPP}}{\sum e^{ULPP}} \qquad \text{(Eq. 6)}$$

Eq. 7 may be used for addition in log space approximation:

$$\ln(x+y) \approx \ln(e^{\ln(x)\ln(y)}+1)+\ln(y) \qquad \text{(Eq. 7)}$$

The linear opinion pool (LOP) of Eq. 5 as applied to herein is provided in Eq. 8, where posterior probability (PP) vectors are [3,1] and weights, a, are scalars.

$$LOP = \alpha_{spike} PP_{spike} + \alpha_{LFP} PP_{LFP} \qquad \text{(Eq. 8)}$$

In Eq. 8, $\alpha$ represents a [2,1] weight vector where and:

$$\sum_i \alpha_i = 1$$

Training of a discrete fusion algorithm is described below.

May weights may be selected to maximize the percent correct classification. Measuring the percent correct classification may include creating a confusion matrix, or table in which the $ij^{th}$ entry is the count of points that are actually of class i and classified as class j. From the confusion matrix, the percent correct classification (PCC) may be computed using Eq. 9, where Tr(CM) is the trace of the confusion matrix and N is the total number of trials included in the confusion matrix.

$$pcc = \frac{\text{Tr}(CM)}{N} \qquad \text{(Eq. 9)}$$

The complete data set may be the raw output of the individual decoders from their respective analysis. The data set may include a cross-fold validation analysis and may vary the set of spike units.

The may be, for example, at least 30N data points for each class, where N is the number of independent classifier weights. In the case of this analysis N=1 and there are approximately about 220 trials per class. A problem with three classifiers may have, for example, at least 900 trials. With four or more classifiers, this condition may not be met.

(a) Analysis to Support Design Decisions

Viability of decision fusion may be assessed to show that it is possible to improve the performance of the system with respect to any of the individual classifiers by combining information.

As described above, for a three-class decision fusion problem with two individual classifiers as input, only the linear and log opinion pools may be considered. Since spike performance may degrade over time, analysis may include varying the subset of spike units.

Figure 50:
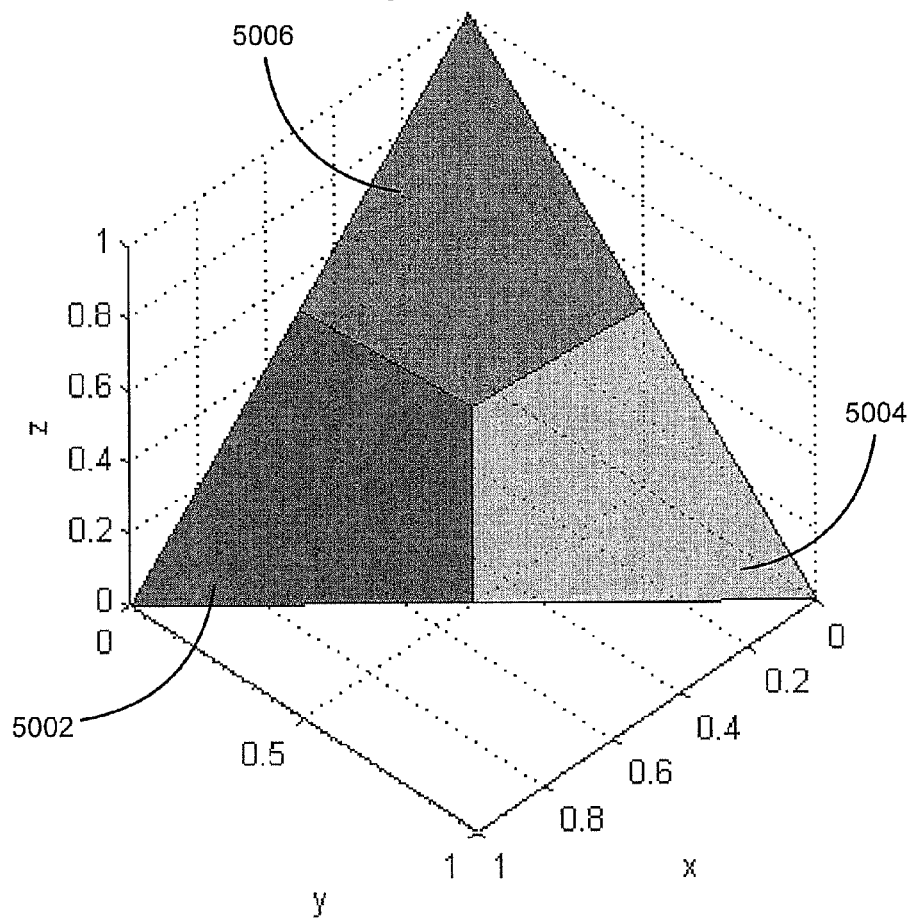
FIG. 50 is a graphic illustration of an equilateral triangle within a plane.

FIG. 50 is a graphic illustration of an equilateral triangle 5000 within a plane x+y+z 1=0 and bounded by the planes x=0, y=0, z=0.

Each normalized probability vector may be visualized as a point on equilateral triangle 5000. The index containing the maximum value may be selected as the most likely class, which partitions triangle 5000 into three regions, as illustrated in FIG. 50. Points that lie inside a blue region 5002 may be classified as class 1. Points that lie inside a green region 5004 may be classified as class 2. Points that lie inside a red region 5006 may be classified as class 3. Points near vertices of the triangles have higher confidences of being correctly classified. Points near decision boundaries, between regions 5002, 5004, and 5006, have lower confidences of being correctly classified.

Figure 51:
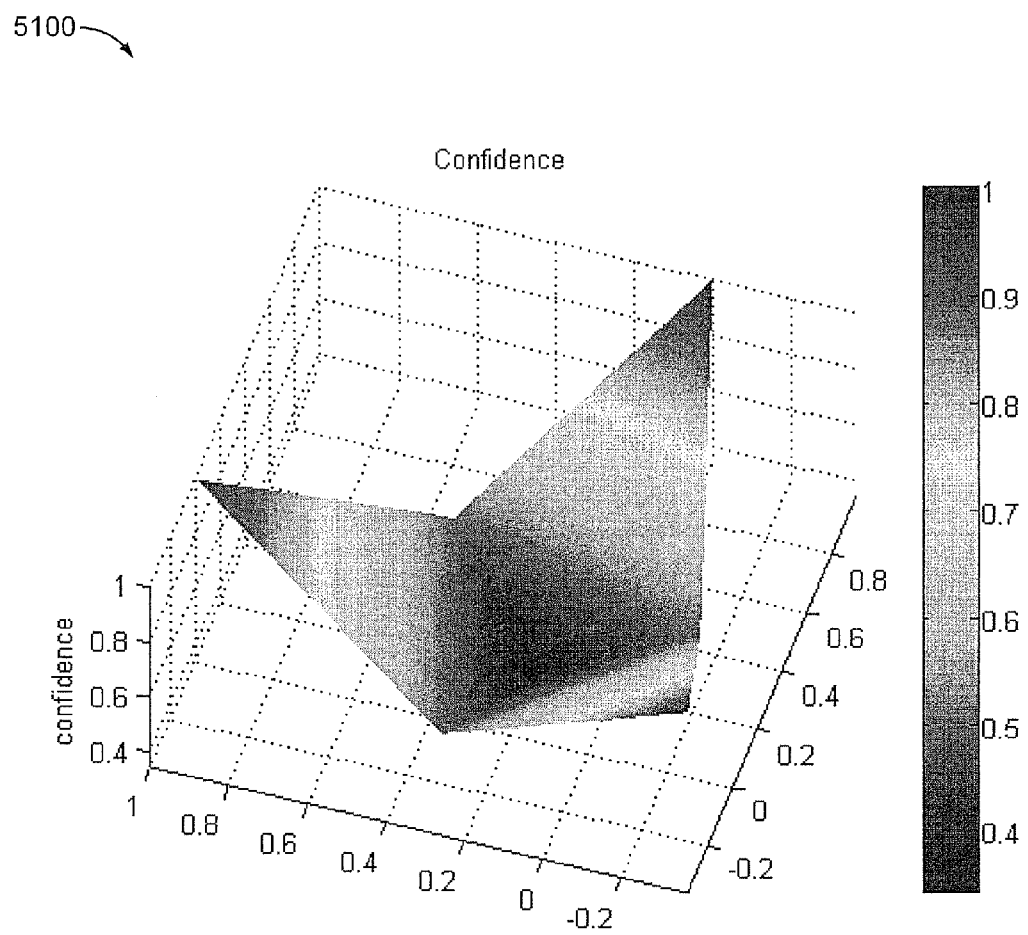
FIG. 51 is a graphic illustration of confidence of a chosen class for a normalized 3-class problem.

FIG. 51 is a graphic illustration 5100 of confidence of a chosen class for a normalized 3-class problem. Where a data point is to be classified as one of the three classes, the lower bound on the confidence is ⅓.

Figure 52:
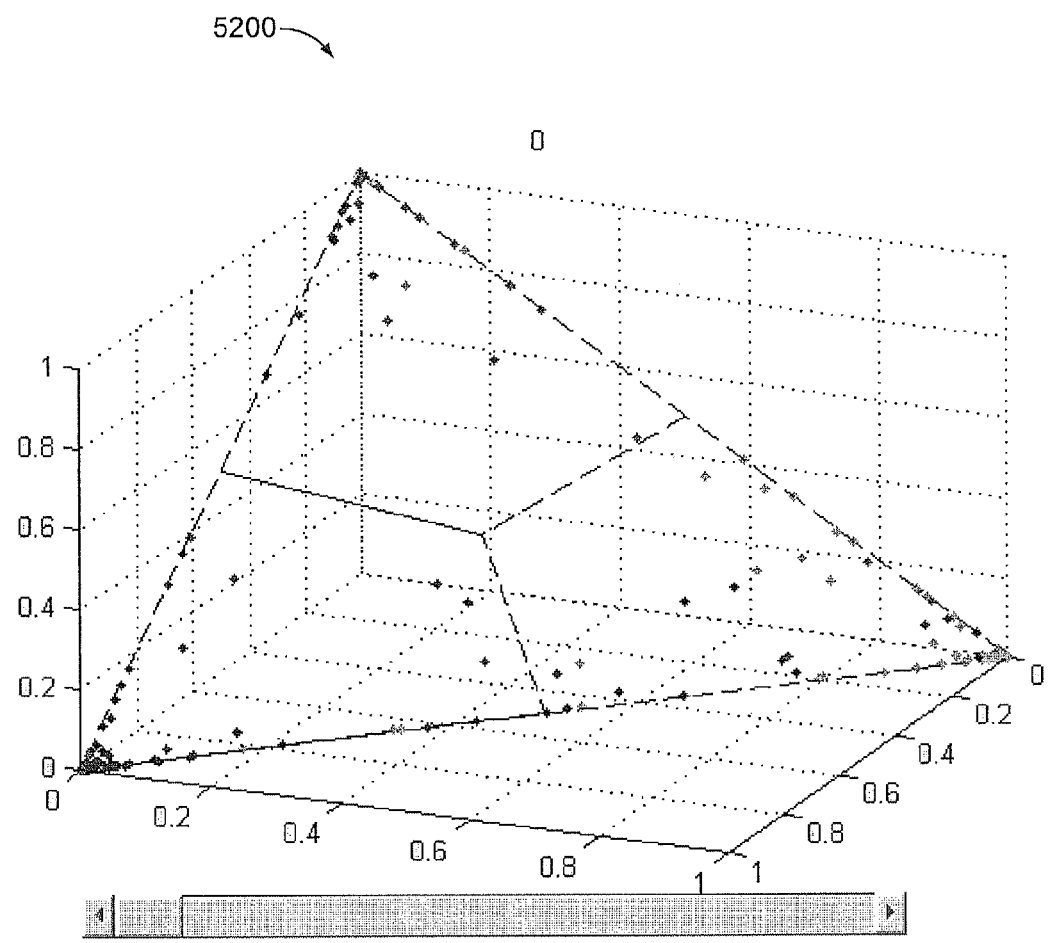
FIG. 52 is a plot of a set of points corresponding to results from a LFP classifier.
Figure 53:
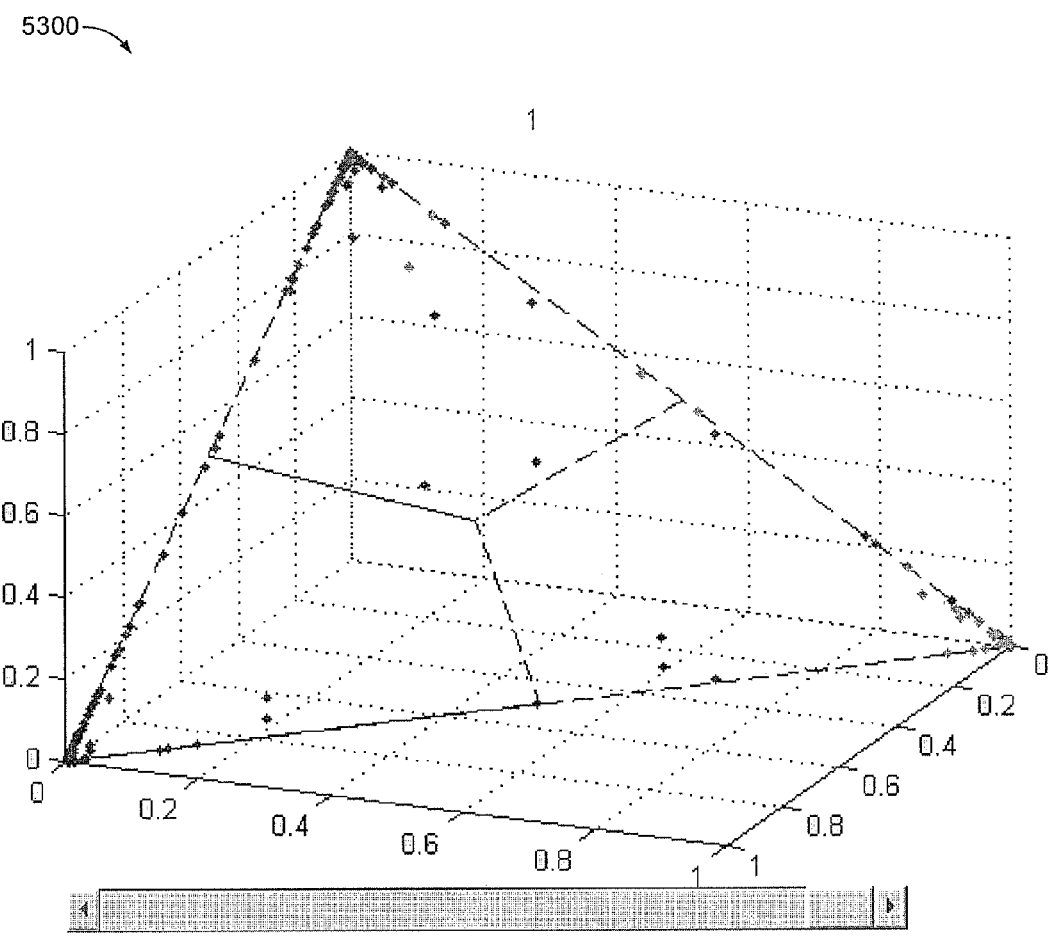
FIG. 53 is a plot of a set of points corresponding to results from a spike classifier.
Figure 54:
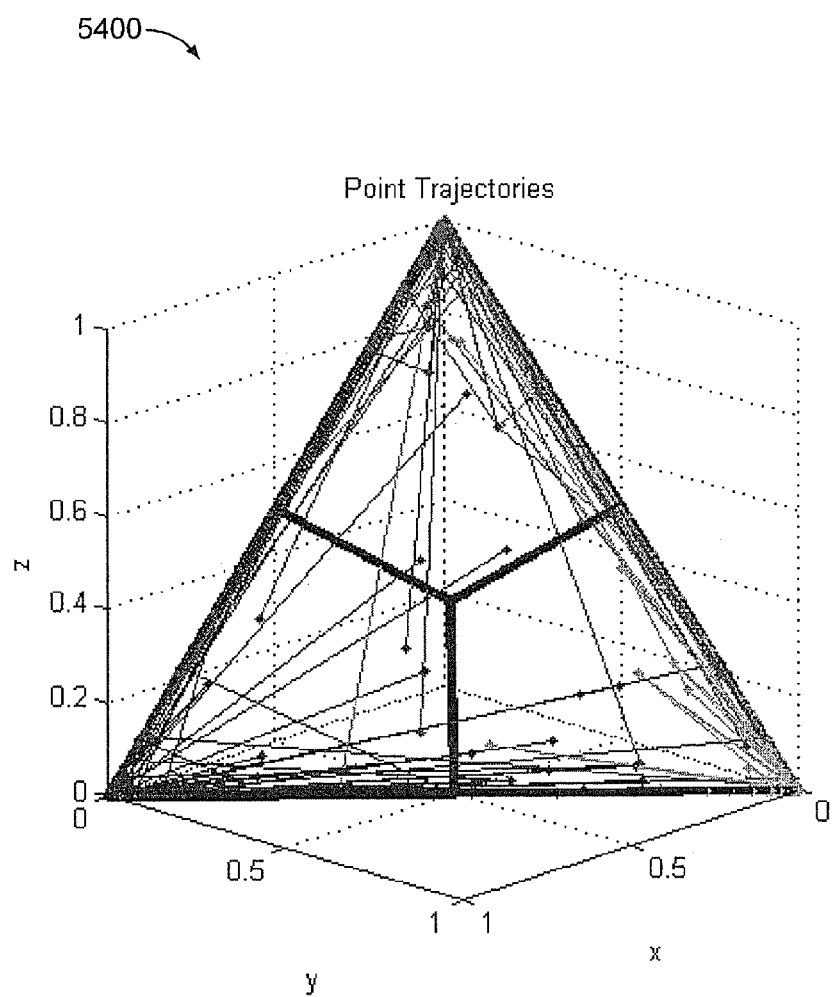
FIG. 54 is a graphic illustration to show how points move along linear trajectories between the two endpoints as the weights are changed.

Normalized decision vectors and corresponding parameterized linear trajectories are represented in FIGS. 52 through 54. FIG. 52 is a plot of a set of points 5200 corresponding to results from a LFP classifier. FIG. 53 is a plot of a set of points 5300 corresponding to results from a spike classifier. In FIGS. 52 and 53, the weight applied to the spike classifier, $\alpha$, is 0 and 1, respectively. It may be assumed that the weight applied to the LFP classifier is 1−$\alpha$.

FIG. 54 is a graphic illustration of points 5400 to show how points move along linear trajectories between the two endpoints as the weights are changed. Some of the trajectories cross decision boundaries, indicating that the individual classifiers disagree. Such a situation provides an opportunity for decision fusion to improve the overall classification.

When individual classifiers disagree, the confidence of the final decision may be lower than if both classifiers agreed. This is indicated when the point on the trajectory along a line that crosses the decision boundary is close to the decision boundary. A point on another trajectory along a line that doesn't cross a decision boundary may be relatively closer to a vertex.

Figure 55:
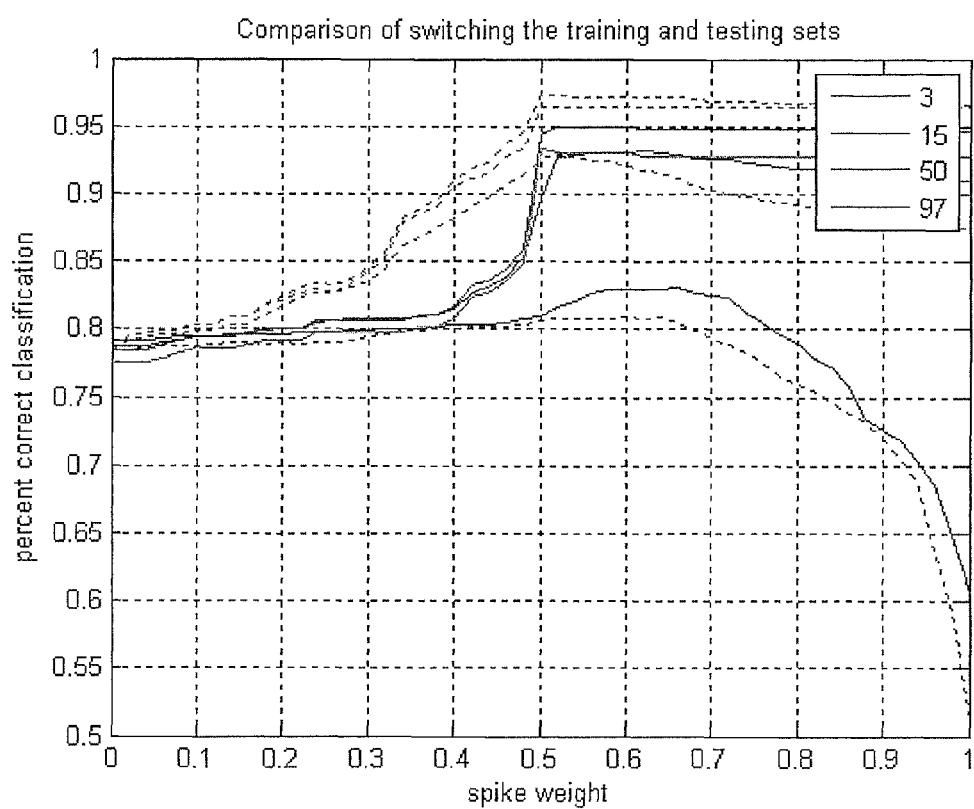
FIG. 55 is a plot of percent correct classification versus spike weight for a two-fold analysis.

A data set was divided into two folds for a two-fold analysis. FIG. 55 is a plot of percent correct classification versus spike weight for the two-fold analysis.

Initially, the first fold was used as a training set and the second fold was used as a testing set. In FIG. 55, a solid line represents correct classification versus spike weight.

The second fold was then used as the training set and the first fold was used as the testing set and the same analysis was applied and plotted in dotted lines of FIG. 55. A visual analysis shows that the weights should generalize.

There may be a tradeoff between the accuracy of two decoders and the amount of cross-correlation between them, in that, as the cross-correlation increases, the benefit that decision fusion provides may decrease. Whereas cross-correlation is likely to be high if both decoders are relatively accurate. Inaccuracies may also tend to lower the cross-correlation.

Figure 56:
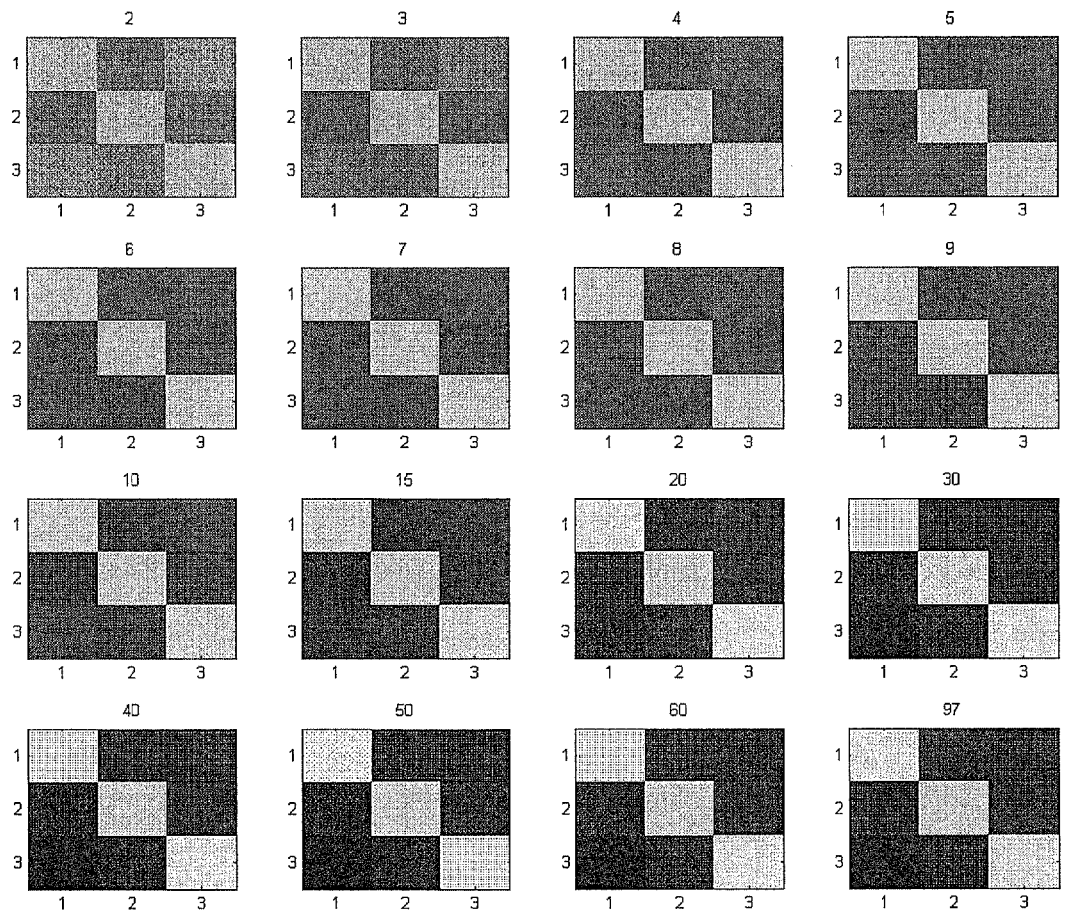
FIG. 56 is a graphic illustration of cross-correlation between classes for various numbers of spike units.

FIG. 56 is a graphic illustration 5600 of cross-correlation between classes for various numbers of spike units. In FIG. 56, the vertical axis represents the spike decoder and horizontal axis represents the LFP decoder. The color scale represents gray-scale values between 0 (black) and 1 (white). The lightest gray in the figure is approximately 0.86.

The results illustrated in FIG. 56 indicate that there may be potential for improvement from decision fusion, and there may be additional potential benefit with lower amounts of spike units. Accuracy of the spike decoder may, however, decrease as units are removed.

An exhaustive search of the weight space may be performed with one free parameter and plots of percent correct classification versus the spike weight generated for each of the two subsets of data.

Figure 57:
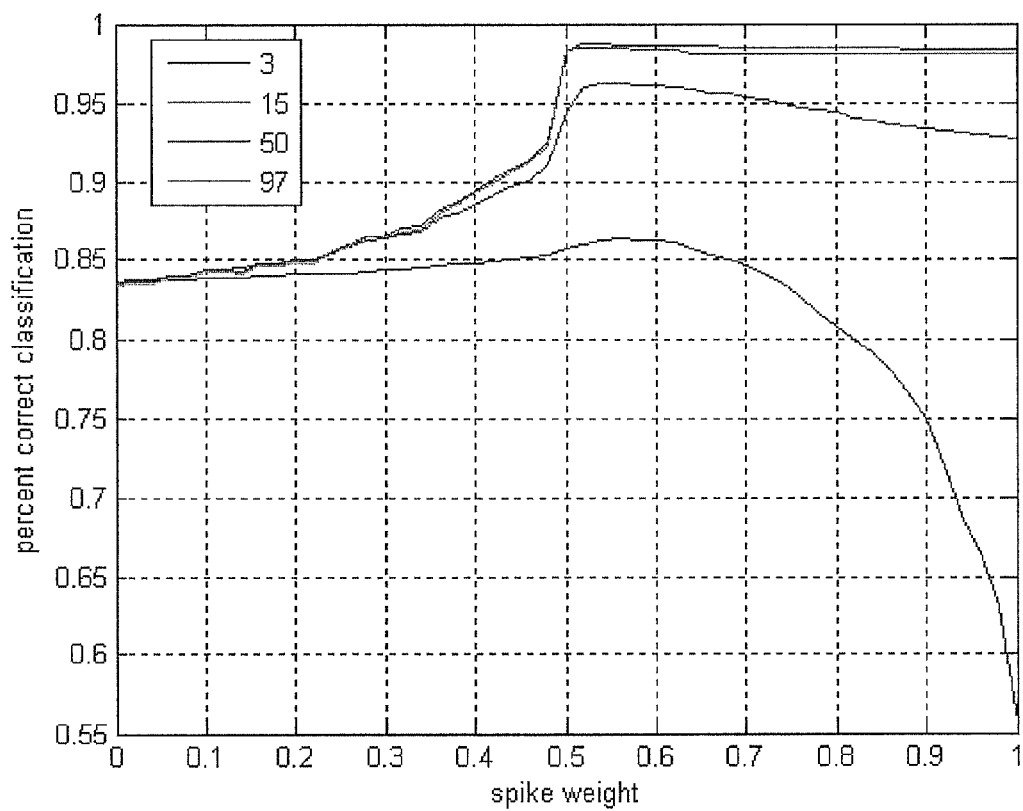
FIG. 57 is a plot of percent correct classification versus spike classifier weights.
Figure 58:
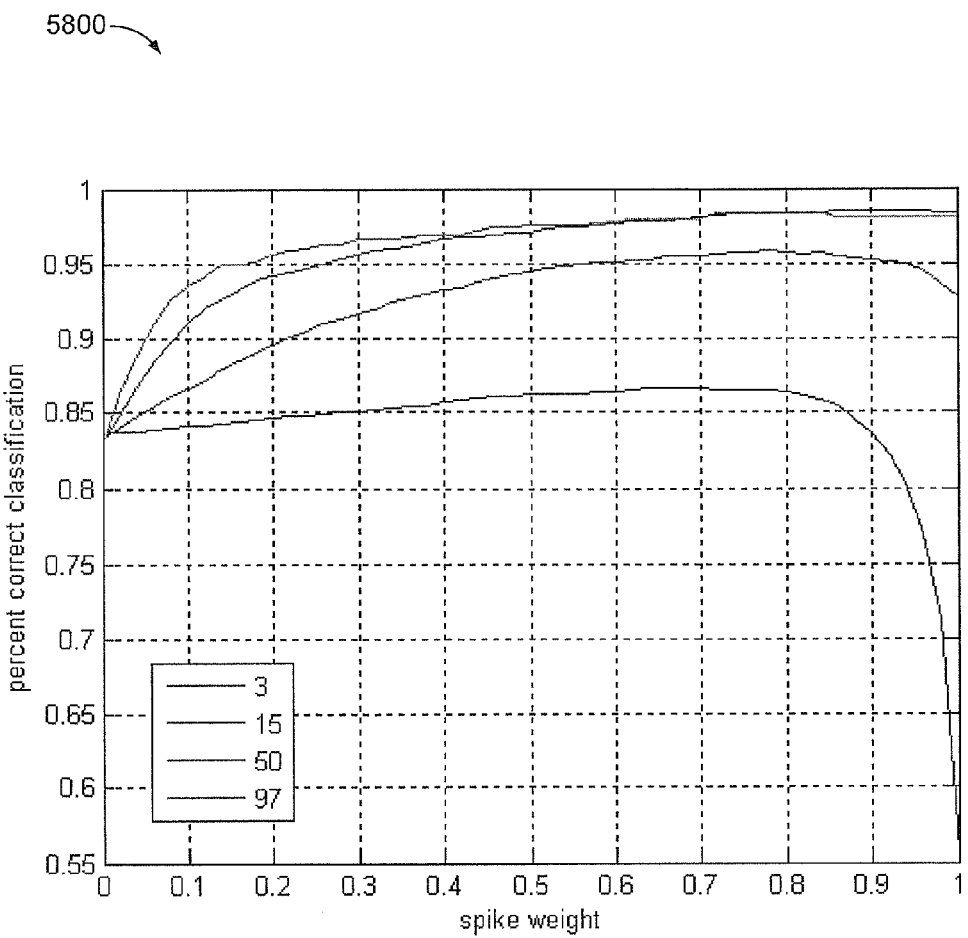
FIG. 58 is another plot of percent correct classification versus spike classifier weights.

FIGS. 57 and 58 are plots 5700 and 5800, respectively, of percent correct classification versus spike classifier weights.

FIG. 57 shows that the percent correct classification is maximized for a spike decoder weight of approximately 0.55 and an LFP decoder weight of approximately 0.45 for each of the two data sets. FIG. 57 also shows that for large numbers of spike units that there is relatively little, if any, benefit in performing decision fusion because the spike decoder is extremely accurate. The benefit to performing decision fusion is realized as spikes degrade over time.

FIG. 58 shows that the results in log space achieve about the same maximal performance, while the optimal weighting appears to be more variable with the number of spike units.

Another method of determining confidence is based on the distributions of weighted decision vectors for each class. This method disregards that the points can be interpreted as probabilities and the estimated density functions determine new decision boundaries for the classes. This method is more complicated and may not generalize as well, for reasons described below with respect to FIGS. 59, 60, and 61.

Figure 59:
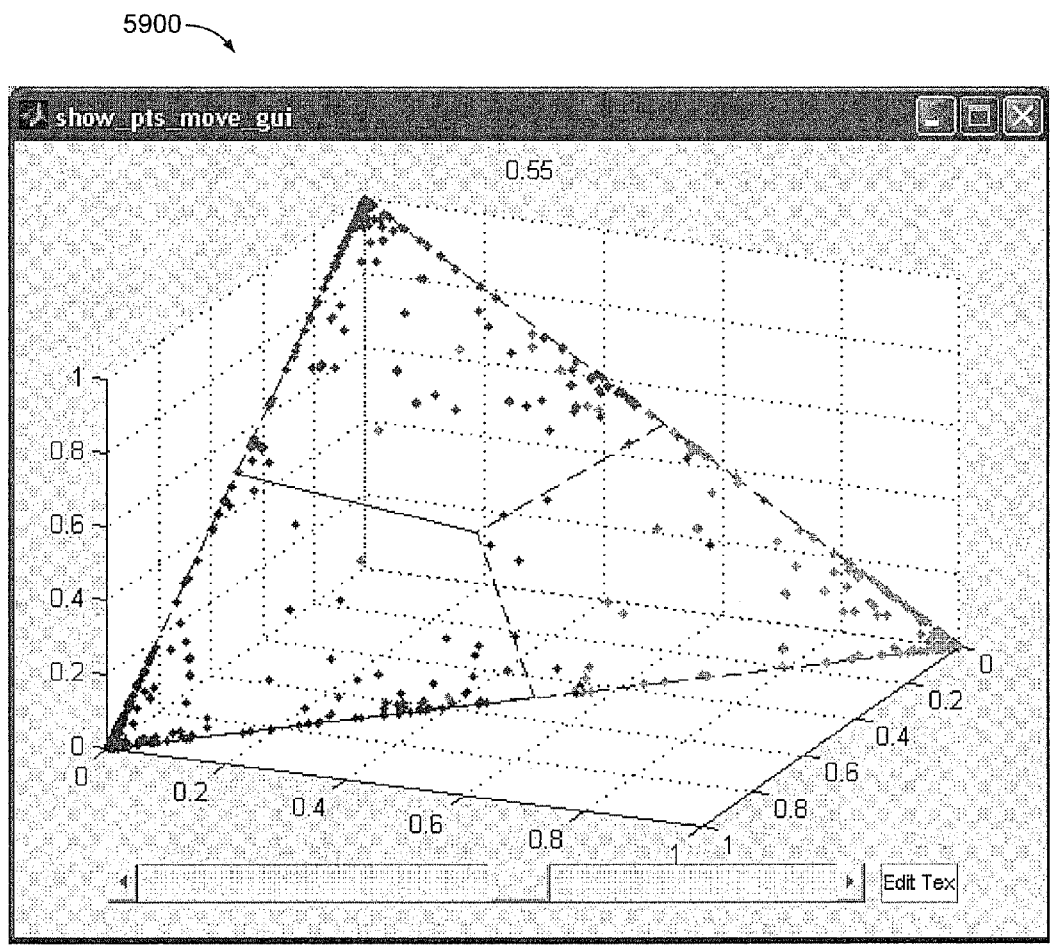
FIG. 59 is a plot of weighted normalized probabilities in a decision space.

FIG. 59 is a plot of weighted normalized probabilities in the decision space.

Figure 60:
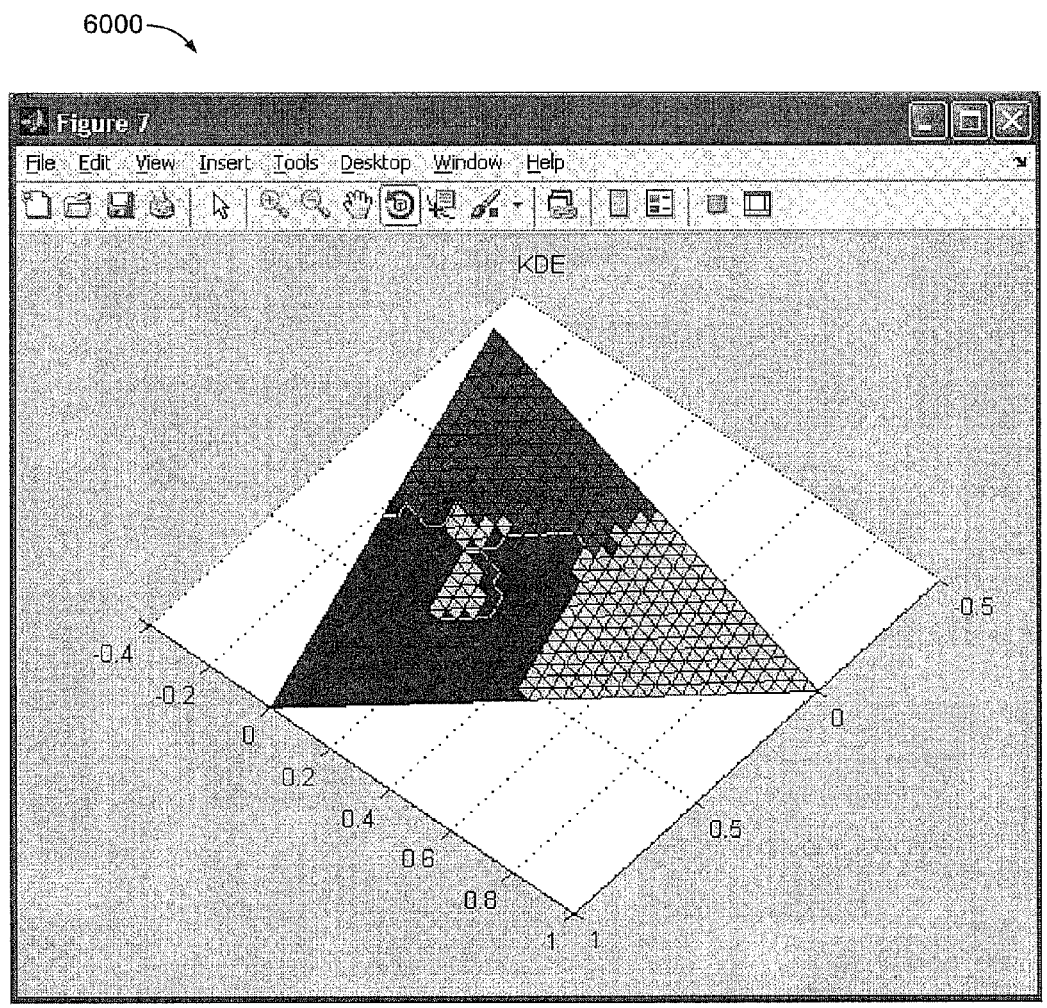
FIG. 60 is a plot of new decision boundaries of the decision space of FIG. 59 computed with kernel density estimation.

FIG. 60 is a plot of corresponding new decision boundaries computed with kernel density estimation.

Figure 61:
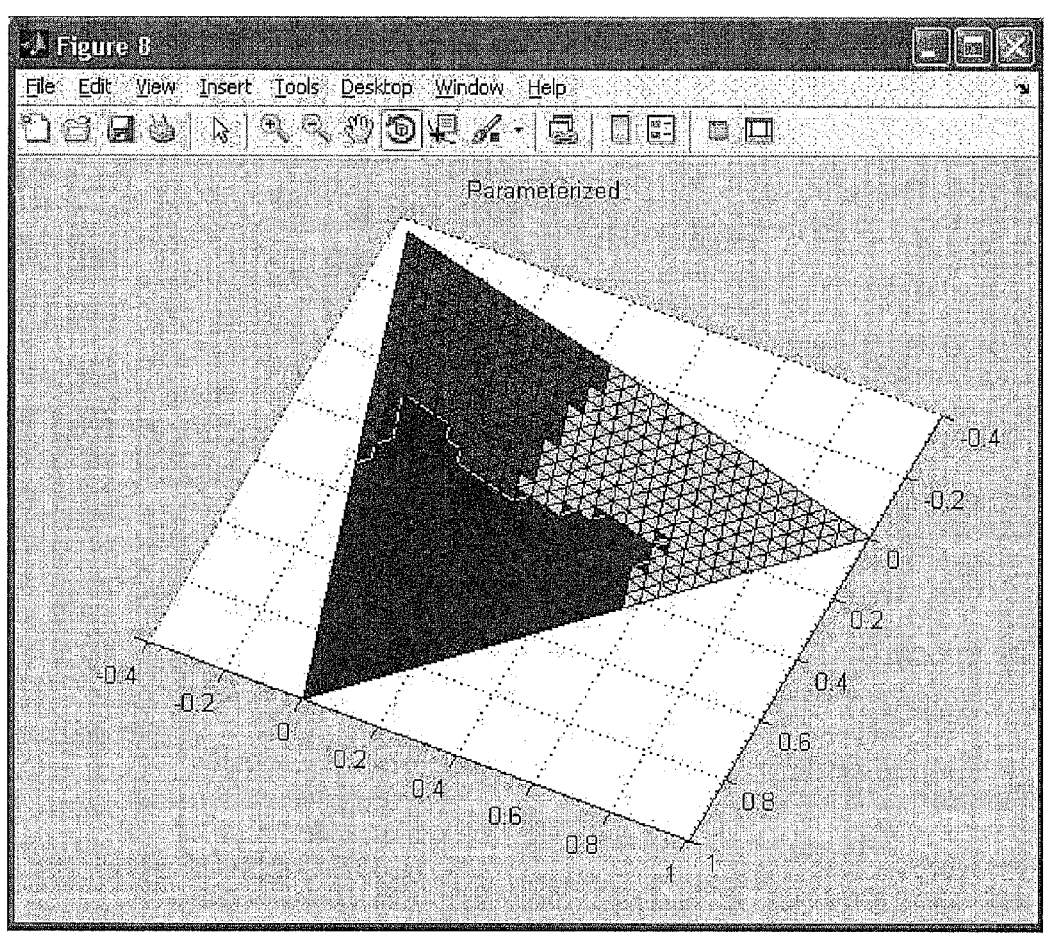
FIG. 61 is a plot of corresponding new decision boundaries of the decision space computed with parameterized curve fits to the kernel density estimation of FIG. 60.

FIG. 61 is a plot of corresponding new decision boundaries computed with parameterized curve fits to the kernel density estimation of FIG. 60.

In FIG. 60, there is a noncontiguous region where points are classified as class 2 (green) on the kernel density estimated decision boundaries, which can be explained by the two points which belong to class 2 in the sparse section of the decision space just left of center on the figure. This phenomenon is the why these results may not generalize well.

The parameterized density estimation of FIG. 61 is based on the kernel density estimation of FIG. 60. The kernel method of FIG. 60 should generalize in order to consider the parameterized estimate of the kernel density estimate of FIG. 61.

One or more features disclosed herein may be implemented in hardware, software, firmware, and combinations thereof, including discrete and integrated circuit logic, application specific integrated circuit (ASIC) logic, and microcontrollers, and may be implemented as part of a domain-specific integrated circuit package, or a combination of integrated circuit packages. The term software, as used herein, refers to a computer program product including a computer readable medium having computer program logic stored therein to cause a computer system to perform one or more features and/or combinations of features disclosed herein.

Figure 62:
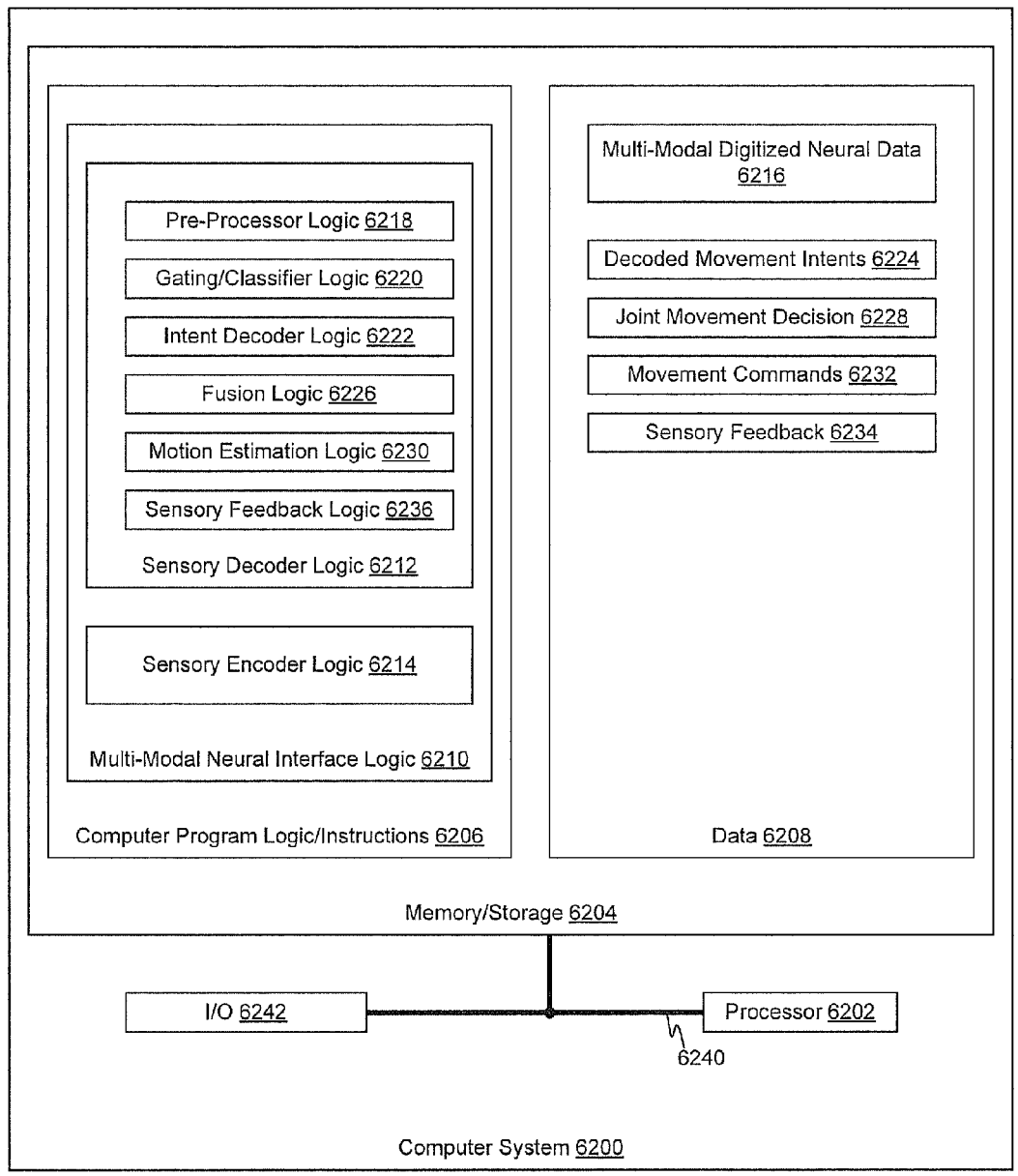
FIG. 62 is a block diagram of a computer system.

FIG. 62 is a block diagram of a computer system 6200, including one or more computer instruction processing units, illustrated here as a processor 6202, to execute computer program product logic, also known as instructions, code, and software.

One or more features of computer system 6200 may be distributed amongst multiple devices. For example, one or more of a NI, a NFU, a MCU, a cMCU, a pMCU, a multi-BID, and a multi-PID may include a corresponding processor 6202.

Computer system 6200 includes memory/storage 6204, including a computer readable medium having computer program product logic or instructions 6206 stored thereon, to cause processor 6202 to perform one or more functions in response thereto.

Memory/storage 6204 further includes data 6208 to be used by processor 6202 in executing instructions 6206, and/or generated by processor 6202 in response to execution of instructions 6206.

Logic 6206 includes multi-modal neural interface (NI) logic 6210 to cause processor 6202 to multi-modally interface between physiological devices and a prosthetic system, such as described in one or more examples above.

NI logic 6210 may include one or more of sensory decoder logic 6212 and sensory encoder logic 6214.

Sensory decoder logic 6212 may include logic to cause processor 6202 to decode user movement intents from digitized multi-modal neural data 6216, which may be received from a plurality of types of sensors 112 (FIG. 1), and/or as a plurality of types of signals 110 (FIG. 1), such as described in one or more examples above.

Sensory decoder logic 6212 may include pre-processor logic 6218 to cause processor 6202 to pre-process multi-modal data 6216, such as described in one or more examples above.

Sensory decoder logic 6212 may include gating/classifier logic 6220 to cause processor 6202 to gate and/or classify movement states from multi-modal data 6216, such as described in one or more examples above.

Sensory decoder logic 6212 may include intent decoder logic 6222 to cause processor 6202 to decode user movement intents 6224 from each of the plurality of types of multi-modal data 6216, such as described in one or more examples above. Sensory decoder logic 6212 may include fusion logic 6226 to cause processor 6202 to fuse multiple movement intents 6224 into a joint movement decision 6228, such as described in one or more examples above.

Sensory decoder logic 6212 may be configured with respect to a plurality of groups of control to generate a joint movement decision 6228 for each group of control, and may include motion estimation logic 6230 to output one of a plurality of movement commands 6232 based a combination of joint movement decisions 6228, such as described in one or more examples above.

Data 6208 may include sensory feedback data 6234 from a prosthetic device, which may correspond to one or more of sensory feedback 122 and 124 in FIG. 1.

Sensory decoder logic 6212 may include sensory feedback logic 6236 to cause processor 6202 to incorporate sensory feedback 6234, or a portion thereof, such as described in one or more examples above.

Sensory encoder logic 6214 may include logic to cause processor 6202 to map and encode sensory feedback 6234 from n sensors and/or sensor types, to m afferent pathways, such as described in one or more examples above.

Computer system 6200 may include a communications infrastructure 6240 to communicate amongst components of computer system 6200, such as described in one or more examples above.

Computer system 6200 may include an input/output controller 6242 to communicate with one or more other systems, such as described in one or more examples above.

Methods and systems are disclosed herein with the aid of functional building blocks illustrating the functions, features, and relationships thereof. At least some of the boundaries of these functional building blocks have been arbitrarily defined herein for the convenience of the description. Alternate boundaries may be defined so long as the specified functions and relationships thereof are appropriately performed.

One skilled in the art will recognize that these functional building blocks can be implemented by discrete components, application specific integrated circuits, processors executing appropriate software, and combinations thereof.

While various embodiments are disclosed herein, it should be understood that they have been presented by way of example only, and not limitation. It will be apparent to persons skilled in the relevant art that various changes in form and detail may be made therein without departing from the spirit and scope of the methods and systems disclosed herein. Thus, the breadth and scope of the claims should not be limited by any of the exemplary embodiments disclosed herein.

What is claimed is:

1. A neural interface system comprising:
   a prosthetic device;
   a plurality of types of sensors configured to receive a plurality of types of physiological activity signals from a prosthetic device user;
   a neural interface configured to decode a user movement intent from each of the plurality of signals types, and fuse the movement intents into a joint decision to control moveable elements of the prosthetic device, the neural interface comprising:
   a plurality of classifier modules, each classifier module associated with a corresponding one of the signal types and configured to determine a user movement state from signals of the signal type;
   a plurality of decoders, each associated with a corresponding one of the signal types and configured to decode a movement intent from signals of the signal type and from one or more of the user movement states; and
   a fusion module to fuse movement intents from a plurality of the decoders into the joint movement decision;
   wherein the plurality of signal types include a combination of two or more of,
   a local field potential (LFP) signal,
   a unit activity (spike) signal,
   an epidural electrocorticography grid (ECoG) signal,
   an electromyography (EMG) signal,
   an electroencephalography (EEG) signal, and
   an electronystagmography (ENG) signal.

2. The system of claim 1, further including:
   a plurality of groups of the classifier modules, each group associated with a corresponding group of control (GOC) of the prosthetic device;
   a plurality of groups of the decoders, each group associated with a corresponding one of the GOC;
   a plurality of fusion modules, each associated with a corresponding one of the GOCs to fuse the movement intents from decoders of the GOC into a joint decision of the GOC; and
   a motion estimator to generate a movement action from joint movement decisions of a plurality of the GOCs.

3. The system of claim 2, wherein:
   the prosthetic device includes a prosthetic arm and hand; and
   the groups of control include an upper arm group, a wrist group, a hand and finger group, and an endpoint group.

4. The system of claim 2, wherein the plurality of decoders comprise a decoder to process cortical signals, a decoder to process peripheral nerve signals, a decoder to EMG signals, and a decoder to process prosthetic control signals, the system further including:
   a cortical multimodal control unit (cMCU), including the decoder to process the cortical signals;
   a peripheral nerve multimodal control unit (pMCU), including the decoder to process the peripheral nerve signals; and
   a neural fusion unit (NFU), including the fusion module and the decoder to process the EMG and CPC signals.

5. The system of claim 1, wherein at least one of the classifier modules is configured to determine the movement state as one of motionless, pre-movement, and peri-movement.

6. The system of claim 1, wherein the fusion module is configured to perform one or more of decision fusion and data fusion.

7. The system of claim 1, wherein the fusion module is integrated within the decoder.

8. The system of claim 1, further including:
   a plurality of pre-processors, each associated with a corresponding one of the signal types to receive and pre-process signals of the signal type and to selectively direct subsets of the signals to one or more of the classifier modules.

9. The system of claim 8, wherein at least one of the pre-processors includes a multi-stage data validation module, each stage to identify signals as one of valid and invalid as a function of a corresponding metric, and wherein the validation module is configured to identify a validation stage at which a signal is identified as invalid.

10. The system of claim 1, wherein:
the neural interface system is configured to receive and incorporate sensory feedback from the prosthetic device into the joint movement decision; and
the sensory feedback includes one or more of velocity, speed, force, direction, position, and temperature information.

11. The system of claim 1, wherein the plurality of sensors comprises one or more relatively non-invasive physiological sensors or one or more relatively invasive physiological sensors, and
wherein the neural interface system includes a plurality of modular and configurable components, including a base configuration to process signals from the one or more relatively non-invasive physiological sensors, and one or more selectively enabled modules to process signals from the one or more relatively invasive physiological sensors.

12. The system of claim 1, wherein:
at least one of the decoders is configured to compute an unnormalized log posterior probability (ULPP) value for each of a plurality of classes of movement in accordance with Bayesian classifiers, determine the movement intent from the ULPP values, and output the movement intent and the ULPP values; and
the fusion module is configured to generate the joint movement decision based at least in part of the ULPP values.

* * * * *